US008901371B2

(12) United States Patent
Shen et al.

(10) Patent No.: US 8,901,371 B2
(45) Date of Patent: Dec. 2, 2014

(54) COMPOSITIONS AND METHODS FOR IMPROVED PLANT FEEDSTOCK

(75) Inventors: Hui Shen, Ardmore, OK (US); Fang Chen, Ardmore, OK (US); Richard A. Dixon, Sulphur, OK (US)

(73) Assignee: The Samuel Roberts Noble Foundation, Inc., Ardmore, OK (US)

( * ) Notice: Subject to any disclaimer, the term of this patent is extended or adjusted under 35 U.S.C. 154(b) by 297 days.

(21) Appl. No.: 13/462,583

(22) Filed: May 2, 2012

(65) Prior Publication Data

US 2012/0322122 A1 Dec. 20, 2012

Related U.S. Application Data

(60) Provisional application No. 61/483,460, filed on May 6, 2011.

(51) Int. Cl.
*C12N 15/82* (2006.01)
*C12N 15/00* (2006.01)
*A01H 5/00* (2006.01)
*C07K 14/415* (2006.01)

(52) U.S. Cl.
CPC .......... *C07K 14/415* (2013.01); *C12N 15/8243* (2013.01); *C12N 15/8255* (2013.01); *C07K 2319/21* (2013.01); *Y02E 50/343* (2013.01); *C12N 15/8261* (2013.01)
USPC ........ 800/278; 435/320.1; 435/419; 800/298; 800/320; 800/284

(58) Field of Classification Search
None
See application file for complete search history.

(56) References Cited

U.S. PATENT DOCUMENTS

| | | | |
|---|---|---|---|
| 3,990,944 | A | 11/1976 | Gauss et al. |
| 4,461,648 | A | 7/1984 | Foody |
| 4,535,060 | A | 8/1985 | Comai |
| 4,600,590 | A | 7/1986 | Dale |
| 5,000,000 | A | 3/1991 | Ingram et al. |
| 5,037,663 | A | 8/1991 | Dale |
| 5,302,523 | A | 4/1994 | Coffee et al. |
| 5,322,783 | A | 6/1994 | Tomes et al. |
| 5,384,253 | A | 1/1995 | Krzyzek et al. |
| 5,464,765 | A | 11/1995 | Coffee et al. |
| 5,538,877 | A | 7/1996 | Lundquist et al. |
| 5,538,880 | A | 7/1996 | Lundquist et al. |
| 5,545,818 | A | 8/1996 | McBride et al. |
| 5,550,318 | A | 8/1996 | Adams et al. |
| 5,563,055 | A | 10/1996 | Townsend et al. |
| 5,591,616 | A | 1/1997 | Hiei et al. |
| 5,610,042 | A | 3/1997 | Chang et al. |
| 5,972,118 | A | 10/1999 | Hester et al. |
| 8,299,318 | B2 * | 10/2012 | Brover et al. ................. 800/278 |

FOREIGN PATENT DOCUMENTS

WO WO 2005080580 A2 * 9/2005

OTHER PUBLICATIONS

Patzlaff et al, 2003, The Plant J., 36:743-754.*
Shen et al, 2012, New Phytologist, 193:121-136.*
Lucas et al, Gen Bank accession No. FE635325 published Mar. 10, 2008.*
Jin et al, 2000, Embo, 19:6150-6161.*
Besseau et al.,"Flavonoid accumulation in *Arabidopsis* repressed in lignin synthesis affects auxin transport and plant growth," *Plant Cell* 19:148-162, 2007.
Bomal et al., "Involvement of *Pinus taeda* MYB1 and MYB8 in phenylpropanoid metabolism and secondary cell wall biogenesis: a comparative *in planta* analysis," *J. Exp. Bot.* 59:3925-3939, 2008.
Bylesjo, et al., "Integrated analysis of transcript, protein and metabolite data to study lignin biosynthesis in hybrid aspen," *J. Proteome Res.* 8(1):199-210, 2008.
Deluc et al., "Characterization of a grapevine R2R3-MYB transcription factor that regulates the phenylpropanoid pathway," *Plant Physiol.* 140:499-511, 2006.
Dereeper et al.," Phylogeny. fr: robust phylogenetic analysis for the non-specialist," *Nucleic Acids Res.* (Web Server issue): W465-W469, Apr. 19, 2008.
Elkind et al., "Abnormal plant development and down regulation of phenylpropanoid biosynthesis in transgenic tobacco containing a heterologous phenylalanine ammonia-lyase gene," *Proc. Natl. Acad. Sci. USA* 87:9057-9061, 1990.
Fornalé et al., " ZmMYB31 directly represses maize lignin genes and redirects the phenylpropanoid metabolic flux," *Plant J.* 64(4):633-644, 2010.
Fornalé et al., "Down-regulation of the maize and *Arabidopsis thaliana* caffeic acid O- methyl-transferase genes by two new maize R2R3-MYB transcription factors," *Plant Mol. Biol.* 62: 809-823; 2006.
Gális et al., "A novel R2R3 MYB transcription factor NtMYBJS1 is a methyl jasmonate-dependent regulator of phenylpropanoid-conjugate biosynthesis in tobacco," Plant J. 46: 573-592; 2006.
GenBank Accession No. JF299185, "*Panicum virgatum* R2R3-MYB transcriptional factor PvMYB4a mRNA, complete cds," Dec. 12, 2011.
GenBank Accession No. JF299186, "*Panicum virgatum* R2R3-MYB transcriptional factor PvMYB4b mRNA, complete cds," Dec. 12, 2011.
GenBank Accession No. JF299187, "*Panicum virgatum* R2R3-MYB transcriptional factor PvMYB4c mRNA, complete cds," Dec. 12, 2011.
GenBank Accession No. JF299188, "*Panicum virgatum* R2R3-MYB transcriptional factor PvMYB4d mRNA, complete cds," Dec. 12, 2011.

(Continued)

*Primary Examiner* — Medina A Ibrahim
*Assistant Examiner* — Jason Deveau Rosen
(74) *Attorney, Agent, or Firm* — Dentons US LLP

(57) ABSTRACT

The invention provides methods for modifying lignin content and composition in plants and achieving associated benefits therefrom involving altered expression of newly discovered MYB4 transcription factors. Nucleic acid constructs for modifying MYB4 transcription factor expression are described. By over-expressing the identified MYB4 transcription factors, for example, an accompanying decrease in lignin content may be achieved. Plants are provided by the invention comprising such modifications, as are methods for their preparation and use.

20 Claims, 22 Drawing Sheets

(56) References Cited

OTHER PUBLICATIONS

GenBank Accession No. JF299189, "*Panicum virgatum* R2R3-MYB transcriptional factor PvMYB4e mRNA, partial cds," Dec. 12, 2011, Dec. 21, 2011.
GenBank Accession No. NM_119665, "*Arabidopsis thaliana* transcription factor MYB32 mRNA, complete cds," Jun. 5, 2013; accessed Jul. 29, 2013.
GenBank Accession No. CAE09058, "MYB transcription factor [*Eucalyptus gunnii*]," accessed Aug. 27, 2009.
GenBank Accession No. JQ0960, "myb-related protein 308—garden snapdragon," accessed Feb. 2006.
GenBank Accession No. AY519615, "*Arabidopsis thaliana* MYB transcription factor (At4g38620) mRNA, complete cds," accessed Feb. 7, 2004.
GenBank Accession No. JQ0957, "myb-related protein 330—garden snapdragon," accessed Feb. 2006.
GenBank Accession No. CAJ42204, "transcription factor MYB42 [*Zea mays*]," accessed Mar. 2, 2006.
GenBank Accession No. CAJ42202, "transcription factor MYB31 [*Zea mays*]," accessed Mar. 2, 2006.
GenBank Accession No. P81393, "RecName: Full=Myb-related protein 308," accessed Jan. 2009.
GenBank Accession No. P81395, "RecName: Full=Myb-related protein 330," accessed Jan. 2009
Goicoechea et al., " EgMYB2, a new transcriptional activator from *Eucalyptus* xylem, regulates secondary cell wall formation and lignin biosynthesis," *Plant J.* 43:553-567; 2005.
Jin et al., "Transcriptional repression by AtMYB4 controls production of UV-protecting sunscreens in *Arabidopsis*," *Embo J.* 19:6150-6161; 2000.
Karpinska at al.,"MYB transcription factors are differentially expressed and regulated during secondary vascular tissue development in hybrid aspen," *Plant Mol. Biol.* 56:255-270: 2004.
Legay et al., "Molecular characterization of *EgMYB1*, a putative transcriptional repressor of the lignin biosynthetic pathway," *Plant Sci.* 173: 542-549; 2007.
Mitsuda et al., "NAC transcription factors, NST1 and NST3, are key regulators of the formation of secondary walls in woody tissues of *Arabidopsis*," *Plant Cell* 19:270-280, 2007.
Patzlaff et al.,"Charactensation of a pine MYB that regulates lignification," *Plant J.* 36:743-754; 2003.

Preston at al.,"AtMYB32 is required for normal pollen development in *Arabidopsis thaliana*," *Plant J.* 40:979-995; 2004.
Romero at al., "More than 80 R2R3-MYB regulatory genes in the genome of *Arabidopsis thaliana*," *Plant J.* 14: 273-284;1998.
Shen at al., "Developmental control of lignification in stems of lowland switchgrass variety Alamo and the effects on saccharification efficiency," *BioEnerg. Res.* 2:233-245; 2009.
Shen et al., "Functional characterization of the switchgrass (*Panicum virgatum*) R283-MY8 transcription factor *PvMYB4* for improvement of lignocellulosic feedstocks," *New Phytologist*, 193:121-136: 2012.
Sonbol et al., "The maize *Zm*MYB42 represses the phenylpropanoid pathway and affects the cell wall structure, composition and degradability in *Arabidopsis thaliana*," *Plant Mol. Biol.*70: 283-296, Feb. 24, 2009.
Stracke et al., "The R2R3-MYB gene family in *Arabidopsis thaliana*," *Curr. Opin. Plant Biol.* 4:447-456, 2001.
Tamagnone et al., "The AmMYB308 and AmMYB330 transcription factors from Antirrhinum regulate phenylpropanoid and lignin biosynthesis in transgenic tobacco," *Plant Cell* 10:135-154; 1998.
Tobias et al.," Analysis of expressed sequence tags and the identification of associated short tandem repeats in switchgrass," *Theor. Appl. Genet.* 111:956-964; 2005.
Tobias et al., "Comparative genomics in switchgrass using 61,585 high-quality expressed sequence tags," *Plant Genome* 1:111-124; Nov. 2008.
Wang et al., "Mutation of WRKY transcription factors initiates pith secondary wall formation and increases stem biomass in dicotyledonous plants," *Proc. Natl. Acad. Sci. USA* early edition; pp. 1-6; 2010.
Zhao et al., "Over-expression of the *AtGA2ox8* gene decreases the biomass accumulation and lignification in rapeseed (*Brassica napus* L.)," J. Zhejiang Univ. Sci. B 11:471-481; 2010.
Zhao et al., "SAD2, an importin β-like protein, is required for UV-B response in *Arabidopsis* by mediating MYB4 nuclear trafficking," *Plant Cell* 19:3805-3818; 2007.
Zhao et al.,"Transcriptional networks for lignin biosynthesis: more complex than we thought?" *Trends Plant Sci.* 16(4):227-233, 2011.
Zhong et al.,"Evolutionary conservation of the transcriptional network regulating secondary cell wall biosynthesis," *Trends Plant Sci.* 15: 625-632; Nov. 2010.
Zhou et al., "Distinct cinnamoyl CoA reductases involved in parallel routes to lignin in *Medicago truncatula*." *Proc. Natl. Acad. Sci.* USA 107: 17803-17808; Oct. 12, 2010.

* cited by examiner

```
AtMYB4     MGRSPCCEKAHTNKGAWTKEEDERLVAYIKAHGEGCWRSLPKAAGLLRCGKSCRLRWINY   60
AtMYB32    MGRSPCCEKDHTNKGAWTKEEDDKLISYIKAHGEGCWRSLPRSAGLQRCGKSCRLRWINY   60
AmMYB308   MGRSPCCEKAHTNKGAWTKEEDDRLVAYIRAHGEGCWRSLPKAAGLLRCGKSCRLRWINY   60
EgMYB1     MGRSPCCEKAHTNKGAWTKEEDDKLIAYIRAHGEGCWRSLPKAAGLLRCGKSCRLRWINY   60
PvMYB4     MGRSPCCEKAHTNKGAWTKEEDDRLVAYIRAHGEGCWRSLPKAAGLLRCGKSCRLRWINY   60
ZmMYB42    MGRSPCCEKAHTNRGAWTKEEDERLVAYVRAHGEGCWRSLPRAAGLLRCGKSCRLRWINY   60
ZmMYB31    MGRSPCCEKAHTNKGAWTKEEDERLVAHIRAHGEGCWRSLPKAAGLLRCGKSCRLRWINY   60
           ********* *** *********  *   **********  *** ************

AtMYB4     LRPDLKRGNFTEEEDELIIKLHSLLGNKWSLIAGRLPGRTDNEIKNYWNTHIRRKLINRG  120
AtMYB32    LRPDLKRGNFTLEEDDLIIKLHSLLGNKWSLIATRLPGRTDNEIKNYWNTHVKRKLLRKG  120
AmMYB308   LRPDLKRGNFTEEEDELIIKLHSLLGNKWSLIAGRLPGRTDNEIKNYWNTHIRRKLLSRG  120
EgMYB1     LRPDLKRGNFTEEEDEIIIKLHSLLGNKWSLIAGRLPGRTDNEIKNYWNTHIRRKLLNRG  120
PvMYB4     LRPDLKRGNFTADEDDLIVKLHSLLGNKWSLIAARLPGRTDNEIKNYWNTHIKRKLLSRG  120
ZmMYB42    LRPDLKRGNFTADEDDLIVKLHSLLGNKWSLIAARLPGRTDNEIKNYWNTHIRRKLLGSG  120
ZmMYB31    LRPDLXRGNFTEEEDELIVKLHSVLGNKWSLIAGRLPGRTDNEIKNYWNTHIRRKLLSRG  120
           ********** **  *  **** ********* ****************** * *

AtMYB4     IDPTSHRPIQESSASQDSKPTQLEPVTSNTINIS-----FTSAPKVETFHESISFPGKSE  175
AtMYB32    IDPATHRPINETKTSQDSSDS----SKTEDPLVKI-----LSFGPQLEKIAN---FGDER- 175
AmMYB308   IDPTTHRSINDGTASQDQVTT-ISFSNANSKEED------TKHKVAVDIMIK---------  165
EgMYB1     IDPATHRLINEPAQDHHDEPT-ISFAANSKEIKE------MKNNAELNFMCN---------  165
PyMYB4     IDPVTHRPIAD-AARNVTISFQPDAPSQQQ---------LSDDAEAPP-----------  158
ZmMYB42    DPVTHRRVAG--GAA-TTISFQP-SPNSAA----------AAAAAETAA-----------  156
ZmMYB31    IDPVTHRPVTEHHASNITISFETEVAAAARDDKKGAVFRLEDEEEEERNKATMVVGRDRQ  180
           *** **

AtMYB4     KIS-MLTFKEEKD-ECPVQEKFPDLNLELRISLPDDVDRLQ----GNG---KSTTP---  222
AtMYB32    -------IQKRVE-YSVVEERCLDLNLELRISPP-WQDKLH----DERNLRFGRVKY---  212
AmMYB308   -------EEN-----SPVQERCPDLNLDLKISPPCQQQINY----HQENLKTGGRNGSS-  208
EgMYB1     -------LEESADVASSARERCPDLNLELGISPPS-HQLHQ----PEPLLRFTGRK--S  210
PvMYB4     ----PPPPPQQQQQLKPPPRCPDLNLDLCISPPCHKE----EEDQEL-IKPAAVKREML  209
ZmMYB42    ----QAPIKAEETAAVKAP-RCPDLNLDLCISPPCQHEDDGEEEDEELDKPAFVKREAL  211
ZmMYB31    SQSHSHSHPAGEWGQGKRPLKCPDLNLDLCISPPCQEEE--EMEEAAMRVRPA-VKREA-  236
                                **** * ** *
```

FIG. 1A

```
AtMYB4      ----------RCFKCSLGMIN-GMECRCGRMRCDVVGGSS---KGSDMSN--GFDFLGLAK   267
AtMYB32     ----------RCSACRFGFGN-GKECSCNNVKCQTEDSSSSSYSSTDISSSIGYDFLGLNN   262
AmMYB308    ---------TLCFVCRLGIQN-SKDCSCSDGVGN--------------------------   232
EgMYB1      --------DLCXECNLGLKN-SQNCRCSVGVIESETSV-------------GYDFLGLKA    248
PvMYB4      GHGT-LGLCFGCSLGLQKGAAGCTCSSN-----------------------SHFLGLRV    246
ZmMYB42     QAGHGHGHGLCLGCGLGGQKGAAGCSCSNG----------------------HHFLGLRT    249
ZmMYB31     ---------GLCFGCSLGLPR-TADCKCSS----------------------SSFLGLRT    264
                      *  *   *       * *
```

```
AtMYB4      KETTSLLGFRSLEMK    282
AtMYB32     ---TRVLDFSTLEMK    274
AmMY308     ---------------
EgMYB1      ----SVLDYRS----    255
PvMYB4      G---MLLDFRGLEMX    258
ZmMYB42     ----SVLDFRGLEMX    260
ZmMYB31     ----AMLDFRSLEMX    275
```

FIG. 1A continued

```
PvMYB4a  MGRSPCCEKAHTNKGAWTKEEDDRLVAYIRAHGEGCWRSLPKAAGLLRCGKSCRLRWINY  60
PvMYB4c  MGRSPFCEKAHTNKGAWTKEEDDRLVAYIRAHGEGCWRSLPKAAGLLRCGKSCRLRWINY  60
PvMYB4e  MGRSPCCEKAHTNKGAWTKEEDDRLVAYIRAHGEGCWRSLPKAAGLLRCGKSCRLRWINY  60
PvMYB4d  MGRSPCCEKAHTNKGAWTKEEDDRLVAYIRAHGEGCWRSLPKAAGLLRCGKSCRLRWINY  60
PvMYB4b  MGRSPCCEKAHTNKCAWTKEEDDRLVAYIRAHGEGCWRSLPKAAGLLRCGKSCRLRWINY  60
         ***** ******* **********************************************

PvMYB4a  LRPDLKRGNFTADEDDLIVKLHSLLGNKWSLIAARLPGRTDNEIKNYWNTHIKRKLLSRG  120
PvMYB4c  LRPDLKRGNFTADEDDLIVKLHSLLGNKWSLIAARLPGRTDNEIKNYWNTHIKRKLLSRG  120
PvMYB4e  LRPDLKRGNFTADEDDLIVKLHSLLGNKWSLIAARLPGRTDNEIKNYWNTHIKRKLLSRG  120
PvMYB4d  LRPDLKRGNFTADEDDLIVKLHSLLGNKWSLIAARLPGRTDNEIKNYWNTHIKRKLLSRG  120
PvMYB4b  LRPDLKRGNFTADEDDLIVKLHSLLGNKWSLIAARLPGRTDNEIKNYWNTHIKRKLLSRG  120
         ************************************************************

PvMYB4a  IDPVTHRPIADAARNVTISFQPDAPSQQQLSDDAEAPPPPPPPQQQQQQLKPPPRCPDLN  180
PvMYB4c  IDPVTHRPIADAARNVTISFQPDAPSQQQLSDDAEAPPPPPPPQQQQQQLKPPPRCPDLN  180
PvMYB4e  IDPVTHRPIADAARNVTISFQPDAPSQQQLSDDAEAPPPPPP--QQQQQQLKPPPRCPDLN  178
PvMYB4d  IDPVTHRPIADAARNVTISFQPDAPSQQQLSDDAEAPPPPPP--QQQQQQLKPPPRCPDLN  178
PvMYB4b  IDPVTHRPIADAARNVTISFQPDAPSQQQLSDDAEAPPPPPP--QQQQQQLKPPPRCPDLN  178
         ********************************************  **************

PvMYB4a  LDLCISPPCHKEEEDQELIKPAAVKREMLQAGHGTLGLCFGCSLGLQKGAAGCTCSSNSH  240
PvMYB4c  LDLCISPPCHKEEEDQELIKPAAVKREMLQAGHGTLGLCFGCSLGLQKGAAGCTCSSNSH  240
PvMYB4e  LDLCISPPCHKEEEDQELVKPAAVKREMLQAGHGTLGLCFGCSLGLQKGAAGCTCSSNSH  238
PvMYB4d  LDLCISPPCHKEEEDQELVKPAAVKREMLQAGHGTLGLCFGCSLGLQKGAAGCTCSSNSH  238
PvMYB4b  LDLCISPPCHKEEEDQELVKPAAVKREMLQAGHGTLGLCFGCSLGLQKGAAGCTCGSNSH  238
         ****************** ************************************ ****

PvMYB4a  FLGLRVGMLLDFRGLEMK  258
PvMYB4c  FLGLRVGMLLDFRGLEMK  258
PvMYB4e  FLGLRVGMLLDFRGLEMK  256
PvMYB4d  FLGLRVGMLLDFRGLEMK  256
PvMYB4b  FLGLRVGMLLDFRGLEMK  256
         ******************
```

FIG. 2A

| Gene Name | Accession # | Different ESTs (Variants) |
|---|---|---|
| PvMYB4a | JF299185 | >7L-8-17<br>>7L-11<br>>7L-16-19<br>>7L-37-26<br>>7L-6<br>>7S-31<br>>7S-39<br>>MYB_6497_S3 |
| PvMYB4b | JF299186 | >7L-14 |
| PvMYB4c | JF299187 | >7L-20-22 |
| PvMYB4d | JF299188 | >7L-25<br>>7S-41<br>>7S-46<br>>7L-21-2<br>>MYB_6497_S11<br>>MYB_6497_S8 |
| PvMYB4e | JF299189 | >7L-32 |

FIG. 2B

Sense Probe        Anti-Sense Probe

GFP        Bright Field        Merged

```
AC-I
AGTCCACCTACCGCCACCTACCGCCACCTACCGCTGTTCTCGA
AC-II
AGTCCACCAACCGCCACCAACCGCCACCAACCGCTGTTCTCGA
AC-III
AGTCCACCTAACTCTACCTAACTCTACCTAACGCTGTTCTCGA
AC-IV
AGTCCACCAAACTCTACCAAACTCTACCAAACGCTGTTCTCGA
```
FIG. 4A
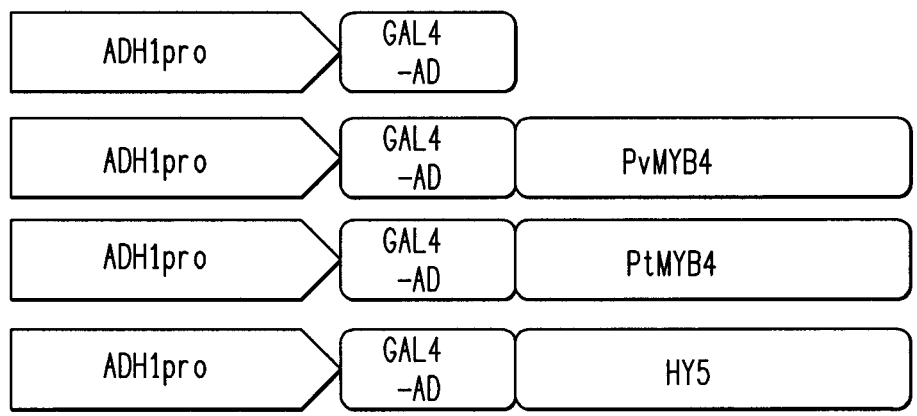
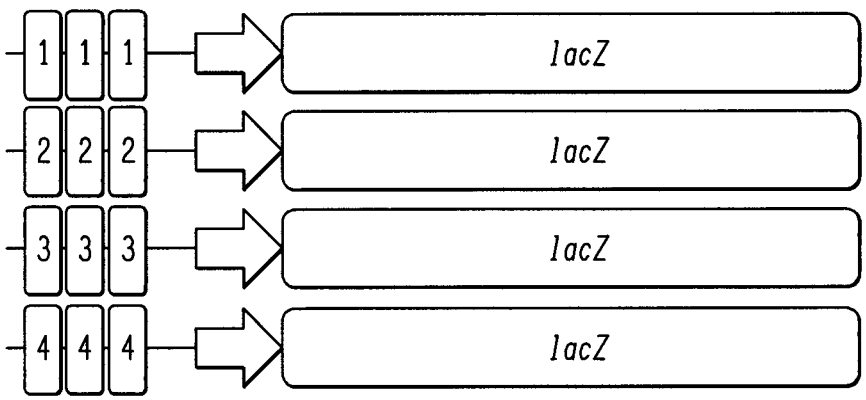
FIG. 4B

SEQUENCE LISTING

<160> NUMBER OF SEQ ID NOS: 192

<210> SEQ ID NO 1
<211> LENGTH: 777
<212> TYPE: DNA
<213> ORGANISM: Panicum virgatum

<400> SEQUENCE: 1

```
atggggcggt cgccgtgctg cgagaaggcg cacacgaaca agggcgcctg gaccaaggag      60
gaggacgacc gcctcgtcgc ctacatccgg gcgcacggcg aggggtgctg gcgctccctc     120
cccaaggccg cgggcctcct gcgctgcggc aagagctgcc gccttcgctg gatcaactac     180
ctccgccggg acctcaagcg cggcaacttc accgccgacg aggacgacct catcgtcaag     240
ctccacagcc tcctcggcaa caagtggtcg ctcatcgccg cgcgcctccc cggccgcacc     300
gacaacgaga tcaagaacta ctggaacacg cacatcaagc gcaagctcct cagccgcggc     360
atcgaccccg tcacacaccg ccccatcgcc gacgcagcca gaaacgtcac catctccttc     420
cagcccgacg cgccgtcgca gcagcagctc agcgacgacg ccgaggcgcc gccgccgccg     480
ccgccgccgc agcagcagca gcagcagctc aagccgccgc caggtgccc  cgacctcaat     540 ctcgacctct gcatcagccc gccctgccac aaggaagaag aggaccagga gctcatcaag     600
cccgccgccg tcaagcgcga gatgctgcag gccggccacg gcactctagg actctgcttc     660
ggctgcagcc tgggcctcca gaaggggcgcc gccgggtgca cctgcagcag caacagccac     720
ttcctggggc tcagggtcgg catgctcctc gacttcagag gcctcgagat gaagtga        777
```

<210> SEQ ID NO 2
<211> LENGTH: 258
<212> TYPE: PRT
<213> ORGANISM: Panicum virgatum

<400> SEQUENCE: 2

```
Met Gly Arg Ser Pro Cys Cys Glu Lys Ala His Thr Asn Lys Gly Ala
1               5                   10                  15

Trp Thr Lys Glu Glu Asp Asp Arg Leu Val Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Ala Asp Glu Asp Asp Leu Ile Val Lys
65                  70                  75                  80

Leu His Ser Leu Leu Gly Asn Lys Trp Ser Leu Ile Ala Ala Arg Leu
                85                  90                  95
```

```
Pro Gly Arg Thr Asp Asn Glu Ile Lys Asn Tyr Trp Asn Thr His Ile
            100                 105                 110
Lys Arg Lys Leu Leu Ser Arg Gly Ile Asp Pro Val Thr His Arg Pro
        115                 120                 125
Ile Ala Asp Ala Ala Arg Asn Val Thr Ile Ser Phe Gln Pro Asp Ala
    130                 135                 140
Pro Ser Gln Gln Gln Leu Ser Asp Asp Ala Glu Ala Pro Pro Pro Pro
145                 150                 155                 160
Pro Pro Pro Gln Gln Gln Gln Gln Leu Lys Pro Pro Pro Arg Cys
                165                 170                 175
Pro Asp Leu Asn Leu Asp Leu Cys Ile Ser Pro Pro Cys His Lys Glu
        180                 185                 190
Glu Glu Asp Gln Glu Leu Ile Lys Pro Ala Ala Val Lys Arg Glu Met
    195                 200                 205
Leu Gln Ala Gly His Gly Thr Leu Gly Leu Cys Phe Gly Cys Ser Leu
    210                 215                 220
Gly Leu Gln Lys Gly Ala Ala Gly Cys Thr Cys Ser Ser Asn Ser His
225                 230                 235                 240
Phe Leu Gly Leu Arg Val Gly Met Leu Leu Asp Phe Arg Gly Leu Glu
                245                 250                 255
Met Lys

<210> SEQ ID NO 3
<211> LENGTH: 7
<212> TYPE: DNA
<213> ORGANISM: Artificial sequence
<220> FEATURE:
<223> OTHER INFORMATION: Synthetic sequence

<400> SEQUENCE: 3 acctacc                                                              7

<210> SEQ ID NO 4
<211> LENGTH: 7
<212> TYPE: DNA
<213> ORGANISM: Artificial sequence
<220> FEATURE:
<223> OTHER INFORMATION: Synthetic sequence

<400> SEQUENCE: 4 accaacc                                                              7

<210> SEQ ID NO 5
<211> LENGTH: 7
<212> TYPE: DNA
<213> ORGANISM: Artificial sequence
<220> FEATURE:
<223> OTHER INFORMATION: Synthetic sequence

<400> SEQUENCE: 5 acctaac                                                              7

<210> SEQ ID NO 6
<211> LENGTH: 7
<212> TYPE: DNA
<213> ORGANISM: Artificial sequence
<220> FEATURE:
<223> OTHER INFORMATION: Synthetic sequence

<400> SEQUENCE: 6 accaaac                                                              7
```

-continued

<210> SEQ ID NO 7
<211> LENGTH: 771
<212> TYPE: DNA
<213> ORGANISM: Panicum virgatum

<400> SEQUENCE: 7

```
atggggcggt cgccgtgctg cgagaaggcg cacacgaaca agtgcgcctg gaccaaggag      60
gaggacgacc gcctcgttgc ctacatccgg gcgcacggcg aggggtgctg gcgctccctc     120
cccaaggccg cgggcctgct cgctgcggc aagagctgcc gcctgcgctg gatcaactac     180
ctccgcccgg acctcaagcg cggcaacttc accgccgacg aggacgacct catcgtcaag     240
ctccacagcc tcctcggcaa caagtggtcg ctcatcgccg cgcgcctccc cggccgcacc     300
gacaacgaga tcaagaacta ctggaacacg cacatcaagc gcaagctcct cagccgcggc     360
atcgaccccg tcacacaccg ccccatcgcc gacgcagcca gaaacgtcac catctccttc     420
cagcccgacg cgccgtcgca gcagcagctc agcgacgacg ccgaggcgcc gccgccgccg     480
ccgccgcagc agcagcagca gctcaagccg ccgcccaggt gccccgacct caatctcgac     540
ctctgcatca gcccgccctg ccacaaggaa gaagaggacc aggagctcgt caagcccgcc     600
gccgtcaagc gcgagatgct gcaggccggc cacggcactc taggactctg cttcggctgc     660
agcctgggcc tccagaaggg cgccgccggg tgcacctgcg gcagcaacag ccacttcctg     720
gggctcaggg tcggcatgct cctcgacttc agaggcctcg agatgaagtg a              771
```

<210> SEQ ID NO 8
<211> LENGTH: 256
<212> TYPE: PRT
<213> ORGANISM: Panicum virgatum

<400> SEQUENCE: 8

```
Met Gly Arg Ser Pro Cys Cys Glu Lys Ala His Thr Asn Lys Cys Ala
1               5                   10                  15

Trp Thr Lys Glu Glu Asp Asp Arg Leu Val Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Ala Asp Glu Asp Asp Leu Ile Val Lys
65                  70                  75                  80

Leu His Ser Leu Leu Gly Asn Lys Trp Ser Leu Ile Ala Ala Arg Leu
                85                  90                  95

Pro Gly Arg Thr Asp Asn Glu Ile Lys Asn Tyr Trp Asn Thr His Ile
            100                 105                 110

Lys Arg Lys Leu Leu Ser Arg Gly Ile Asp Pro Val Thr His Arg Pro
        115                 120                 125

Ile Ala Asp Ala Ala Arg Asn Val Thr Ile Ser Phe Gln Pro Asp Ala
    130                 135                 140

Pro Ser Gln Gln Gln Leu Ser Asp Asp Ala Glu Ala Pro Pro Pro
145                 150                 155                 160

Pro Pro Gln Gln Gln Gln Leu Lys Pro Pro Arg Cys Pro Asp
                165                 170                 175

Leu Asn Leu Asp Leu Cys Ile Ser Pro Pro Cys His Lys Glu Glu Glu
            180                 185                 190
```

```
Asp Gln Glu Leu Val Lys Pro Ala Val Lys Arg Glu Met Leu Gln
            195                 200                 205

Ala Gly His Gly Thr Leu Gly Leu Cys Phe Gly Cys Ser Leu Gly Leu
    210                 215                 220

Gln Lys Gly Ala Ala Gly Cys Thr Cys Gly Ser Asn Ser His Phe Leu
225                 230                 235                 240

Gly Leu Arg Val Gly Met Leu Leu Asp Phe Arg Gly Leu Glu Met Lys
                245                 250                 255

<210> SEQ ID NO 9
<211> LENGTH: 777
<212> TYPE: DNA
<213> ORGANISM: Panicum virgatum

<400> SEQUENCE: 9
atggggcggt cgccgttctg cgagaaggcg cacacgaaca agggcgcctg gaccaaggag    60
gaggacgacc gcctcgtcgc ctacatccgg gcgcacggcg aggggtgctg gcgctccctc   120
cccaaggccg cgggcctcct gcgctgcggc aagagctgcc gccttcgctg gatcaactac   180
ctccgcccgg acctcaagcg cggcaacttc accgccgacg aggacgacct catcgtcaag   240
ctccacagcc tcctcggcaa caagtggtcg ctcatcgccg cgcgcctccc cggccgcacc   300
gacaacgaga tcaagaacta ctggaacacg cacatcaagc gcaagctcct cagccgcggc   360
atcgaccccg tcacacaccg ccccatcgcc gacgcagcca gaaacgtcac catctccttc   420
cagcccgacg cgccgtcgca gcagcagctc agcgacgacg ccgaggcgcc gccgccgccg   480
ccgccgccgc agcagcagca gcagcagctc aagccgccgc ccaggtgccc cgacctcaat   540
ctcgacctct gcatcagccc gccctgccac aaggaagaag aggaccagga gctcatcaag   600
cccgccgccg tcaagcgcga gatgctgcag gccggccacg gcactctagg actctgcttc   660
ggctgcagcc tgggcctcca aagggcgcc gccgggtgca cctgcagcag caacagccac   720
ttcctggggc tcagggtcgg catgctcctc gacttcagag gcctcgagat gaagtga      777

<210> SEQ ID NO 10
<211> LENGTH: 258
<212> TYPE: PRT
<213> ORGANISM: Panicum virgatum

<400> SEQUENCE: 10

Met Gly Arg Ser Pro Phe Cys Glu Lys Ala His Thr Asn Lys Gly Ala
1               5                   10                  15

Trp Thr Lys Glu Glu Asp Asp Arg Leu Val Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
 50                  55                  60

Leu Lys Arg Gly Asn Phe Thr Ala Asp Glu Asp Leu Ile Val Lys
65                  70                  75                  80

Leu His Ser Leu Leu Gly Asn Lys Trp Ser Leu Ile Ala Ala Arg Leu
                85                  90                  95

Pro Gly Arg Thr Asp Asn Glu Ile Lys Asn Tyr Trp Asn Thr His Ile
            100                 105                 110

Lys Arg Lys Leu Leu Ser Arg Gly Ile Asp Pro Val Thr His Arg Pro
        115                 120                 125

Ile Ala Asp Ala Ala Arg Asn Val Thr Ile Ser Phe Gln Pro Asp Ala
```

```
                    130                 135                 140
Pro Ser Gln Gln Gln Leu Ser Asp Asp Ala Glu Ala Pro Pro Pro
145                 150                 155                 160

Pro Pro Pro Gln Gln Gln Gln Gln Leu Lys Pro Pro Pro Arg Cys
                165                 170                 175

Pro Asp Leu Asn Leu Asp Leu Cys Ile Ser Pro Pro Cys His Lys Glu
                180                 185                 190

Glu Glu Asp Gln Glu Leu Ile Lys Pro Ala Ala Val Lys Arg Glu Met
            195                 200                 205

Leu Gln Ala Gly His Gly Thr Leu Gly Leu Cys Phe Gly Cys Ser Leu
        210                 215                 220

Gly Leu Gln Lys Gly Ala Ala Gly Cys Thr Cys Ser Ser Asn Ser His
225                 230                 235                 240

Phe Leu Gly Leu Arg Val Gly Met Leu Leu Asp Phe Arg Gly Leu Glu
                245                 250                 255

Met Lys

<210> SEQ ID NO 11
<211> LENGTH: 771
<212> TYPE: DNA
<213> ORGANISM: Panicum virgatum

<400> SEQUENCE: 11
atggggcggt cgccgtgctg cgagaaggcg cacacgaaca agggcgcctg gaccaaggag     60
gaggacgacc gcctcgttgc ctacatccgg gcgcacggcg aggggtgctg gcgctccctc    120
cccaaggccg cgggcctgct gcgctgcggc aagagctgcc gcctgcgctg gatcaactac    180
ctccgcccgg acctcaagcg cggcaacttc accgccgacg aggacgacct catcgtcaag    240
ctccacagcc tcctcggcaa caagtggtcg ctcatcgccg cgcgcctccc cggccgcacc    300
gacaacgaga tcaagaacta ctggaacacg cacatcaagc gcaagctcct cagccgcggc    360
atcgaccccg tcacacaccg ccccatcgcc gacgcagcca gaaacgtcac catctccttc    420
cagcccgacg cgccgtcgca gcagcagctc agcgacgacg ccgaggcgcc gccgccgccg    480
ccgccgcagc agcagcagca gctcaagccg ccgcccaggt gccccgacct caatctcgac    540
ctctgcatca gcccgccctg ccacaaggaa gaagaggacc aggagctcgt caagcccgcc    600
gccgtcaagc gcgagatgct gcaggccggc cacggcactc taggactctg cttcggctgc    660
agcctgggcc tccagaaggg cgccgccggg tgcacctgca gcagcaacag ccacttcctg    720
gggctcaggg tcggcatgct cctcgacttc agaggcctcg agatgaagtg a             771

<210> SEQ ID NO 12
<211> LENGTH: 256
<212> TYPE: PRT
<213> ORGANISM: Panicum virgatum

<400> SEQUENCE: 12

Met Gly Arg Ser Pro Cys Cys Glu Lys Ala His Thr Asn Lys Gly Ala
1               5                   10                  15

Trp Thr Lys Glu Glu Asp Asp Arg Leu Val Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60
```

Leu Lys Arg Gly Asn Phe Thr Ala Asp Glu Asp Leu Ile Val Lys
 65                  70                  75                  80

Leu His Ser Leu Leu Gly Asn Lys Trp Ser Leu Ile Ala Ala Arg Leu
                 85                  90                  95

Pro Gly Arg Thr Asp Asn Glu Ile Lys Asn Tyr Trp Asn Thr His Ile
            100                 105                 110

Lys Arg Lys Leu Leu Ser Arg Gly Ile Asp Pro Val Thr His Arg Pro
        115                 120                 125

Ile Ala Asp Ala Ala Arg Asn Val Thr Ile Ser Phe Gln Pro Asp Ala
    130                 135                 140

Pro Ser Gln Gln Gln Leu Ser Asp Asp Ala Glu Ala Pro Pro Pro
145                 150                 155                 160

Pro Pro Gln Gln Gln Gln Leu Lys Pro Pro Arg Cys Pro Asp
                165                 170                 175

Leu Asn Leu Asp Leu Cys Ile Ser Pro Pro Cys His Lys Glu Glu Glu
                180                 185                 190

Asp Gln Glu Leu Val Lys Pro Ala Val Lys Arg Glu Met Leu Gln
            195                 200                 205

Ala Gly His Gly Thr Leu Gly Leu Cys Phe Gly Cys Ser Leu Gly Leu
    210                 215                 220

Gln Lys Gly Ala Ala Gly Cys Thr Cys Ser Ser Asn Ser His Phe Leu
225                 230                 235                 240

Gly Leu Arg Val Gly Met Leu Leu Asp Phe Arg Gly Leu Glu Met Lys
                245                 250                 255

<210> SEQ ID NO 13
<211> LENGTH: 766
<212> TYPE: DNA
<213> ORGANISM: Panicum virgatum

<400> SEQUENCE: 13
atggggcggt cgccgtgctg cgagaaggcg cacacgaaca agggcgcctg gaccaaggag      60
gaggacgacc gcctcgttgc ctacatccgg gcgcacggcg aggggtgctg gcgctccctc     120
cccaaggccg cgggcctgct cgcgtgcggc aagagctgcc gcctgcgctg gatcaactac     180
ctccgcccgg acctcaagcg cggcaacttc accgccgacg aggacgacct catcgtcaag     240
ctccacagcc tcctcggcaa caagtggtcg ctcatcgccg cgcgcctccc cggccgcacc     300
gacaacgaga tcaagaacta ctggaacacg cacatcaagc gcaagctcct cagccgcggc     360
atcgaccccg tcacacaccg ccccatcgcc gacgcagcca gaaacgtcac catctccttc     420
cagcccgacg cgccgtcgca gcagcagctc agcgacgacg ccgaggcgcc gccgccgccg     480
ccgcagcagc agcagcagca gctcaagccg ccgcccaggt gccccgacct caatctcgac     540
ctctgcatca gcccgccctg ccacaaggaa gaagaggacc aggagctcgt caagcccgcc     600
gccgtcaagc gcgagatgct gcaggccggc cacggcactc taggactctg cttcggctgc     660
agcctgggcc tccagaaggg cgccgccggg tgcacctgca gcagcaacag ccacttcctg     720
gggctcaggg tcggcatgct cctcgacttc agaggcctcg agatga                    766

<210> SEQ ID NO 14
<211> LENGTH: 255
<212> TYPE: PRT
<213> ORGANISM: Panicum virgatum

<400> SEQUENCE: 14

Met Gly Arg Ser Pro Cys Cys Glu Lys Ala His Thr Asn Lys Gly Ala

```
  1               5                  10                 15
Trp Thr Lys Glu Glu Asp Asp Arg Leu Val Ala Tyr Ile Arg Ala His
            20                  25                 30
Gly Glu Gly Cys Trp Arg Ser Leu Pro Lys Ala Ala Gly Leu Leu Arg
            35                  40                 45
Cys Gly Lys Ser Cys Arg Leu Arg Trp Ile Asn Tyr Leu Arg Pro Asp
 50                  55                 60
Leu Lys Arg Gly Asn Phe Thr Ala Asp Glu Asp Leu Ile Val Lys
 65                  70                 75                 80
Leu His Ser Leu Leu Gly Asn Lys Trp Ser Leu Ile Ala Ala Arg Leu
                85                  90                 95
Pro Gly Arg Thr Asp Asn Glu Ile Lys Asn Tyr Trp Asn Thr His Ile
                100                 105                110
Lys Arg Lys Leu Leu Ser Arg Gly Ile Asp Pro Val Thr His Arg Pro
                115                 120                125
Ile Ala Asp Ala Ala Arg Asn Val Thr Ile Ser Phe Gln Pro Asp Ala
                130                 135                140
Pro Ser Gln Gln Gln Leu Ser Asp Asp Ala Glu Ala Pro Pro Pro
145                 150                 155                160
Pro Gln Gln Gln Gln Gln Leu Lys Pro Pro Arg Cys Pro Asp
                165                 170                175
Leu Asn Leu Asp Leu Cys Ile Ser Pro Pro Cys His Lys Glu Glu
                180                 185                190
Asp Gln Glu Leu Val Lys Pro Ala Ala Val Lys Arg Glu Met Leu Gln
                195                 200                205
Ala Gly His Gly Thr Leu Gly Leu Cys Phe Gly Cys Ser Leu Gly Leu
                210                 215                220
Gln Lys Gly Ala Ala Gly Cys Thr Cys Ser Ser Asn Ser His Phe Leu
225                 230                 235                240
Gly Leu Arg Val Gly Met Leu Leu Asp Phe Arg Gly Leu Glu Met
                245                 250                255
```

<210> SEQ ID NO 15
<211> LENGTH: 837
<212> TYPE: DNA
<213> ORGANISM: Arabidopsis lyrata

<400> SEQUENCE: 15

```
atggggaggt ctccttgctg cgagaaagac cacacgaaca aaggagcttg gactaaggaa    60
gaagacgata agcttatctc ttacatcaag tctcacggcg aaggttgttg gcgttctctt   120
cctagatccg ccggtcttca acgttgcggt aaaagctgtc gtctccgttg gattaactat   180
ctccggcctg atctcaagag aggaaatttc accctcgaag aagatgatct catcatcaaa   240
ctccatagcc ttctcggcaa caagtggtct cttatcgcga cgagattacc gggaagaaca   300
gataacgaga ttaagaatta ctggaataca catgttaaga ggaagctatt aagaagaggg   360
attgatcccg cgactcatcg accgatcaac aaaactcctc aagattcgtc tgattctagt   420
aaaacagagg actctcttgt caagattctc tctttcggtc ctcagttgga gaaaatagca   480
aattttgggg acgagagaaa tgaaaaggaa gtcatgtgcc aaaagagag agttgagtac   540
tctgttgtcg aagaaagatg tctagacttg aatcttgagc ttagaatcag tccaccatgg   600
caagaccagc tccatgatga agaaccctg aggtttggga gagtgaagcg tatgtgcact   660
gcgtgccgtt ttggatttgg aacggcaag gagtgtagct gtgataatac gaaatctcaa   720
```

-continued

```
acagaggaca gtagtagcag cagttattct tcaaccgact ttagcagtag cattggttat    780
gacttcttgg gtctaaacaa tagggttttg gattttagca ctttggaaat gaaatga      837
```

<210> SEQ ID NO 16
<211> LENGTH: 278
<212> TYPE: PRT
<213> ORGANISM: Arabidopsis lyrata

<400> SEQUENCE: 16

```
Met Gly Arg Ser Pro Cys Cys Glu Lys Asp His Thr Asn Lys Gly Ala
1               5                   10                  15

Trp Thr Lys Glu Glu Asp Asp Lys Leu Ile Ser Tyr Ile Lys Ser His
            20                  25                  30

Gly Glu Gly Cys Trp Arg Ser Leu Pro Arg Ser Ala Gly Leu Gln Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Leu Glu Glu Asp Leu Ile Ile Lys
65                  70                  75                  80

Leu His Ser Leu Leu Gly Asn Lys Trp Ser Leu Ile Ala Thr Arg Leu
                85                  90                  95

Pro Gly Arg Thr Asp Asn Glu Ile Lys Asn Tyr Trp Asn Thr His Val
            100                 105                 110

Lys Arg Lys Leu Leu Arg Arg Gly Ile Asp Pro Ala Thr His Arg Pro
        115                 120                 125

Ile Asn Lys Thr Pro Gln Asp Ser Ser Asp Ser Ser Lys Thr Glu Asp
    130                 135                 140

Ser Leu Val Lys Ile Leu Ser Phe Gly Pro Gln Leu Glu Lys Ile Ala
145                 150                 155                 160

Asn Phe Gly Asp Glu Arg Asn Glu Lys Glu Val Met Cys Gln Lys Glu
                165                 170                 175

Arg Val Glu Tyr Ser Val Val Glu Arg Cys Leu Asp Leu Asn Leu
            180                 185                 190

Glu Leu Arg Ile Ser Pro Pro Trp Gln Asp Gln Leu His Asp Glu Lys
        195                 200                 205

Asn Leu Arg Phe Gly Arg Val Lys Arg Met Cys Thr Ala Cys Arg Phe
    210                 215                 220

Gly Phe Gly Asn Gly Lys Glu Cys Ser Cys Asp Asn Thr Lys Ser Gln
225                 230                 235                 240

Thr Glu Asp Ser Ser Ser Ser Tyr Ser Thr Asp Phe Ser Ser
                245                 250                 255

Ser Ile Gly Tyr Asp Phe Leu Gly Leu Asn Asn Arg Val Leu Asp Phe
            260                 265                 270

Ser Thr Leu Glu Met Lys
        275
```

<210> SEQ ID NO 17
<211> LENGTH: 768
<212> TYPE: DNA
<213> ORGANISM: Eucalyptus gunnii
<220> FEATURE:
<221> NAME/KEY: misc_feature
<222> LOCATION: (640)..(640)
<223> OTHER INFORMATION: n is a, c, g, or t

<400> SEQUENCE: 17

```
atgggaaggt ctccttgctg cgagaaggct cacacaaaca agggcgcatg gaccaaggag    60
```

```
gaggacgaca agctcattgc ctacataaga gcgcacggcg agggttgctg gcggtcgctc    120
ccgaaggccg cgggcctcct ccgctgtggc aagagctgcc gcctccggtg atcaattac    180 ctgcggccgg acctcaagcg gggcaacttc accgaagaag aggatgagat catcatcaaa    240
ctgcacagcc ttcttggtaa caaatggtcg ctcattgctg gcgtttgcc agggagaacg    300 gacaacgaga tcaagaacta ctggaacacg cacataagga ggaagctttt gaaccgaggc    360
atcgatccgg ccactcacag gctgatcaat gagcccgcac aagatcacca tgacgagccc    420
accatttctt ttgctgctaa ttctaaggag atcaaagaga tgaagaacaa cgcagagctc    480
aatttcatgt gcaacttaga agagtcggca gacgtggcat cgtcggctcg agaaaggtgt    540
cctgacctga atctcgagct cggaatcagc cctccttctc atcaactgca tcagcctgag    600
ccactcttga gattcactgg taggaaaagt gatttgtgtn tggagtgtaa tttgggggttg    660 aaaaatagcc aaaattgcag atgcagtgtt ggggtgatcg agagtgaaac tagtgttggg    720
tatgacttct ggggcttgaa ggcaagtgtt ttggattata ggagctga                 768

<210> SEQ ID NO 18
<211> LENGTH: 255
<212> TYPE: PRT
<213> ORGANISM: Eucalyptus gunnii
<220> FEATURE:
<221> NAME/KEY: misc_feature
<222> LOCATION: (214)..(214)
<223> OTHER INFORMATION: Xaa can be any naturally occurring amino acid

<400> SEQUENCE: 18

Met Gly Arg Ser Pro Cys Cys Glu Lys Ala His Thr Asn Lys Gly Ala
1               5                   10                  15

Trp Thr Lys Glu Glu Asp Asp Lys Leu Ile Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Asp Glu Ile Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Asn Arg Gly Ile Asp Pro Ala Thr His Arg Leu
        115                 120                 125

Ile Asn Glu Pro Ala Gln Asp His His Asp Pro Thr Ile Ser Phe
    130                 135                 140

Ala Ala Asn Ser Lys Glu Ile Lys Glu Met Lys Asn Asn Ala Glu Leu
145                 150                 155                 160

Asn Phe Met Cys Asn Leu Glu Glu Ser Ala Asp Val Ala Ser Ser Ala
                165                 170                 175

Arg Glu Arg Cys Pro Asp Leu Asn Leu Glu Leu Gly Ile Ser Pro Pro
            180                 185                 190

Ser His Gln Leu His Gln Pro Glu Pro Leu Leu Arg Phe Thr Gly Arg
        195                 200                 205

Lys Ser Asp Leu Cys Xaa Glu Cys Asn Leu Gly Leu Lys Asn Ser Gln
    210                 215                 220
```

```
Asn Cys Arg Cys Ser Val Gly Val Ile Glu Ser Glu Thr Ser Val Gly
225                 230                 235                 240

Tyr Asp Phe Leu Gly Leu Lys Ala Ser Val Leu Asp Tyr Arg Ser
                245                 250                 255

<210> SEQ ID NO 19
<211> LENGTH: 47
<212> TYPE: DNA
<213> ORGANISM: Artificial sequence
<220> FEATURE:
<223> OTHER INFORMATION: Primer

<400> SEQUENCE: 19
attataagaa agattaaaaa accaaacaaa tgtacactaa catgact                    47

<210> SEQ ID NO 20
<211> LENGTH: 232
<212> TYPE: PRT
<213> ORGANISM: Antirrhinum majus

<400> SEQUENCE: 20

Met Gly Arg Ser Pro Cys Cys Glu Lys Ala His Thr Asn Lys Gly Ala
1               5                   10                  15

Trp Thr Lys Glu Glu Asp Asp Arg Leu Val Ala Tyr Ile Arg Ala His
                20                  25                  30

Gly Glu Gly Cys Trp Arg Ser Leu Pro Lys Ala Ala Gly Leu Leu Arg
            35                  40                  45

Cys Gly Lys Ser Cys Arg Leu Arg Trp Ile Asn Tyr Leu Arg Pro Asp
        50                  55                  60

Leu Lys Arg Gly Asn Phe Thr Glu Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
                100                 105                 110

Arg Arg Lys Leu Leu Ser Arg Gly Ile Asp Pro Thr Thr His Arg Ser
            115                 120                 125

Ile Asn Asp Gly Thr Ala Ser Gln Asp Gln Val Thr Thr Ile Ser Phe
        130                 135                 140

Ser Asn Ala Asn Ser Lys Glu Glu Asp Thr Lys His Lys Val Ala Val
145                 150                 155                 160

Asp Ile Met Ile Lys Glu Glu Asn Ser Pro Val Gln Glu Arg Cys Pro
                165                 170                 175

Asp Leu Asn Leu Asp Leu Lys Ile Ser Pro Pro Cys Gln Gln Gln Ile
                180                 185                 190

Asn Tyr His Gln Glu Asn Leu Lys Thr Gly Gly Arg Asn Gly Ser Ser
            195                 200                 205

Thr Leu Cys Phe Val Cys Arg Leu Gly Ile Gln Asn Ser Lys Asp Cys
        210                 215                 220

Ser Cys Ser Asp Gly Val Gly Asn
225                 230

<210> SEQ ID NO 21
<211> LENGTH: 849
<212> TYPE: DNA
<213> ORGANISM: Arabidopsis thaliana

<400> SEQUENCE: 21
```

```
atgggaaggt caccgtgctg tgagaaagct cacacaaaca aaggagcatg gacgaaagaa      60
gaggacgaga ggctcgtcgc ctacattaaa gctcatggag aaggctgctg gagatctctc     120
cccaaagccg ccggacttct cgctgtggc aagagctgcc gtctccggtg gatcaactat      180
ctccggcctg accttaagcg tggaaacttc accgaggaag aagacgaact catcatcaag     240
ctccatagcc ttcttggcaa caaatggtcg cttattgccg ggagattacc gggaagaaca     300
gataacgaga taagaactata ttggaacacg catatacgaa gaaagcttat aaacagaggg    360
attgatccaa cgagtcatag accaatccaa gaatcatcag cttctcaaga ttctaaacct    420
acacaactag aaccagttac gagtaatacc attaatatct cattcacttc tgctccaaag    480
gtcgaaacgt tccatgaaag tataagcttt ccgggaaaat cagagaaaat ctcaatgctt    540
acgttcaaag aagaaaaaga tgagtgccca gttcaagaaa agttcccaga tttgaatctt    600
gagctcagaa tcagtcttcc tgatgatgtt gatcgtcttc aagggcatgg aaagtcaaca    660
acgccacgtt gtttcaagtg cagcttaggg atgataaacg gcatggagtg cagatgcgga    720
agaatgagat gcgatgtagt cggaggtagc agcaagggga gtgacatgag caatggattt    780
gatttttttag ggttggcaaa gaaagagacc acttctcttt tgggcttcg aagcttggag    840
atgaaataa                                                            849

<210> SEQ ID NO 22
<211> LENGTH: 282
<212> TYPE: PRT
<213> ORGANISM: Arabidopsis thaliana

<400> SEQUENCE: 22

Met Gly Arg Ser Pro Cys Cys Glu Lys Ala His Thr Asn Lys Gly Ala
1               5                  10                  15

Trp Thr Lys Glu Glu Asp Glu Arg Leu Val Ala Tyr Ile Lys Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Ile Asn Arg Gly Ile Asp Pro Thr Ser His Arg Pro
        115                 120                 125

Ile Gln Glu Ser Ser Ala Ser Gln Asp Ser Lys Pro Ile Gln Leu Glu
    130                 135                 140

Pro Val Thr Ser Asn Thr Ile Asn Ile Ser Phe Thr Ser Ala Pro Lys
145                 150                 155                 160

Val Glu Thr Phe His Glu Ser Ile Ser Phe Pro Gly Lys Ser Glu Lys
                165                 170                 175

Ile Ser Met Leu Thr Phe Lys Glu Glu Lys Asp Glu Cys Pro Val Gln
            180                 185                 190

Glu Lys Phe Pro Asp Leu Asn Leu Glu Leu Arg Ile Ser Leu Pro Asp
        195                 200                 205

Asp Val Asp Arg Leu Gln Gly His Gly Lys Ser Thr Thr Pro Arg Cys
    210                 215                 220
```

```
Phe Lys Cys Ser Leu Gly Met Ile Asn Gly Met Glu Cys Arg Cys Gly
225                 230                 235                 240

Arg Met Arg Cys Asp Val Val Gly Gly Ser Lys Gly Ser Asp Met
            245                 250                 255

Ser Asn Gly Phe Asp Phe Leu Gly Leu Ala Lys Lys Glu Thr Thr Ser
            260                 265                 270

Leu Leu Gly Phe Arg Ser Leu Glu Met Lys
        275                 280
```

<210> SEQ ID NO 23
<211> LENGTH: 47
<212> TYPE: DNA
<213> ORGANISM: Artificial sequence
<220> FEATURE:
<223> OTHER INFORMATION: Primer

<400> SEQUENCE: 23
agtcatgtta gtgtacattt gtttggtttt ttaatctttc ttataat        47

<210> SEQ ID NO 24
<211> LENGTH: 274
<212> TYPE: PRT
<213> ORGANISM: Antirrhinum majus

<400> SEQUENCE: 24

```
Met Gly Arg Ser Pro Cys Cys Glu Lys Ala His Thr Asn Lys Gly Ala
1               5                   10                  15

Trp Thr Lys Glu Glu Asp Gln Arg Leu Ile Asn Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
50                  55                  60

Leu Lys Arg Gly Asn Phe Thr Glu Glu Asp Glu Ile Ile Ile Lys
65                  70                  75                  80

Leu His Ser Leu Leu Gly Asn Lys Trp Ser Leu Ile Ala Gly Ala Leu
                85                  90                  95

Pro Gly Arg Thr Asp Asn Glu Ile Lys Asn Tyr Trp Asn Thr His Ile
            100                 105                 110

Lys Arg Lys Leu Val Ser Arg Gly Ile Asp Pro Gln Thr His Arg Ser
        115                 120                 125

Leu Asn Ser Ala Thr Thr Thr Ala Thr Pro Thr Val Asn Asn
130                 135                 140

Ser Cys Leu Asp Phe Arg Thr Ser Pro Ser Asn Ser Lys Asn Ile Cys
145                 150                 155                 160

Met Pro Thr Thr Asp Asn Asn Asn Ser Ser Ser Thr Asp Asp
                165                 170                 175

Thr Lys Cys Asn Ser Ser Thr Thr Glu Glu Ser Gln Ser Leu Ile Thr
            180                 185                 190

Pro Pro Pro Lys Glu Glu Glu Lys Ser Val Pro Leu Val Asp Leu Glu
        195                 200                 205

Leu Ser Leu Gly Leu Pro Ser Gln Ser Gln Cys Asn Lys Ser Val Ser
    210                 215                 220

Leu Asn Ser Ser Ser Ser Gly Phe Tyr Asp Leu Phe Arg Pro Pro Ala
225                 230                 235                 240

Lys Val Ala Gln Arg Met Cys Val Cys Lys Trp Thr Leu Gly Leu Gln
```

245                 250                 255
Lys Gly Glu Gln Phe Cys Asn Cys Gln Ser Phe Asn Gly Phe Tyr Arg
            260                 265                 270
Tyr Cys

<210> SEQ ID NO 25
<211> LENGTH: 783
<212> TYPE: DNA
<213> ORGANISM: Zea mays

<400> SEQUENCE: 25

| | | | | | |
|---|---|---|---|---|---|
| atgggcggt | cgccgtgctg | cgagaaggcg | cacaccaaca | ggggcgcgtg | gaccaaggag | 60 |
| gaggacgagc | ggctggtggc | ctacgtccgc | gcgcacggcg | aagggtgctg | gcgctcgctg | 120 |
| cccaggcgg | cgggcctgct | cgctgcgcgg | aagagctgcc | gcctgcgctg | gatcaactac | 180 |
| ctccgcccgg | acctcaagcg | aggcaacttc | accgccgacg | aggacgacct | catcgtcaag | 240 |
| ctgcacagcc | tcctcgggaa | caagtggtcg | ctcatcgccg | cgcggctccc | ggggcggacg | 300 |
| gacaacgaga | tcaagaacta | ctggaacacg | cacatccggc | gcaagctgct | gggcagcggc | 360 |
| atcgacccg | tcacgcaccg | ccgcgtcgcg | ggggcgccg | cgaccaccat | ctcgttccag | 420 |
| cccagcccca | actccgccgc | cgccgccgcc | gccgcagaaa | cagcagcgca | ggcgccgatc | 480 |
| aaggccgagg | agacggcggc | cgtcaaggcg | cccaggtgcc | ccgacctcaa | cctggacctc | 540 |
| tgcatcagcc | cgccgtgcca | gcatgaggac | gacggcgagg | aggaggacga | ggagctggac | 600 |
| ctcaagcccg | ccttcgtcaa | gcgggaggcg | ctgcaggccg | gccacggcca | cggccacggc | 660 |
| ctctgcctcg | gctgcggcct | gggcggacag | aagggagcgg | ccgggtgcag | ctgcagcaac | 720 |
| ggccaccact | cctgggggct | caggaccagc | gtgctcgact | tcagaggcct | ggagatgaag | 780 |
| tga | | | | | | 783 |

<210> SEQ ID NO 26
<211> LENGTH: 260
<212> TYPE: PRT
<213> ORGANISM: Zea mays

<400> SEQUENCE: 26

Met Gly Arg Ser Pro Cys Cys Glu Lys Ala His Thr Asn Arg Gly Ala
1               5                   10                  15

Trp Thr Lys Glu Glu Asp Glu Arg Leu Val Ala Tyr Val Arg Ala His
                20                  25                  30

Gly Glu Gly Cys Trp Arg Ser Leu Pro Arg Ala Ala Gly Leu Leu Arg
            35                  40                  45

Cys Gly Lys Ser Cys Arg Leu Arg Trp Ile Asn Tyr Leu Arg Pro Asp
        50                  55                  60

Leu Lys Arg Gly Asn Phe Thr Ala Asp Glu Asp Leu Ile Val Lys
65                  70                  75                  80

Leu His Ser Leu Leu Gly Asn Lys Trp Ser Leu Ile Ala Ala Arg Leu
                85                  90                  95

Pro Gly Arg Thr Asp Asn Glu Ile Lys Asn Tyr Trp Asn Thr His Ile
            100                 105                 110

Arg Arg Lys Leu Leu Gly Ser Gly Ile Asp Pro Val Thr His Arg Arg
        115                 120                 125

Val Ala Gly Gly Ala Ala Thr Thr Ile Ser Phe Gln Pro Ser Pro Asn
    130                 135                 140

Ser Ala Ala Ala Ala Ala Ala Glu Thr Ala Ala Gln Ala Pro Ile

```
                145                 150                 155                 160
Lys Ala Glu Glu Thr Ala Ala Val Lys Ala Pro Arg Cys Pro Asp Leu
                    165                 170                 175

Asn Leu Asp Leu Cys Ile Ser Pro Pro Cys Gln His Glu Asp Asp Gly
                180                 185                 190

Glu Glu Glu Asp Glu Leu Asp Leu Lys Pro Ala Phe Val Lys Arg
            195                 200                 205

Glu Ala Leu Gln Ala Gly His Gly His Gly Leu Cys Leu Gly
        210                 215                 220

Cys Gly Leu Gly Gly Gln Lys Gly Ala Ala Gly Cys Ser Cys Ser Asn
225                 230                 235                 240

Gly His His Phe Leu Gly Leu Arg Thr Ser Val Leu Asp Phe Arg Gly
                    245                 250                 255

Leu Glu Met Lys
            260

<210> SEQ ID NO 27
<211> LENGTH: 828
<212> TYPE: DNA
<213> ORGANISM: Zea mays

<400> SEQUENCE: 27
atggggaggt cgccgtgctg cgagaaggcg cacaccaaca agggcgcgtg gaccaaggag      60
gaggacgagc gcctggtcgc gcacatcagg gcgcacggcg aggggtgctg gcgctcgctg     120
cccaaggccg ccggcctcct cgcgtgcggc aagagctgcc gcctccgctg gatcaactac     180
ctccgccccg acctcaagcg cggcaacttc acggaggaag aggacgagct catcgtcaag     240
ctgcacagcg tcctcggcaa caagtggtcc ctgatcgccg aaggctgccc ggcaggacg      300
gacaacgaga tcaagaacta ctggaacacg cacatccgga ggaagctgct gagcagggg     360
atcgacccgg tgacgcaccg cccggtcacg gagcaccacg cgtccaacat caccatatcg     420
ttcgagacgg aagtggccgc cgctgcccgt gatgataaga agggcgccgt cttccggttg     480
gaggacgagg aggaggagga gcgcaacaag gcgacgatgg tcgtcggccg cgaccggcag     540
agccagagcc acagccacag ccaccccgcc ggcgagtggg gccaggggaa gaggccgctc     600
aagtgccccg acctcaacct ggacctctgc atcagcccgc cgtgccagga ggaggaggag     660
atggaggagg ctgcgatgag agtgagaccg cggtgaagc gggaggccgg gctctgcttc     720
ggctgcagcc tggggctccc caggaccgcg gactgcaagt gcagcagcag cagcttcctc     780
gggctcagga ccgccatgct cgacttcaga agcctcgaga tgaaatga                  828

<210> SEQ ID NO 28
<211> LENGTH: 275
<212> TYPE: PRT
<213> ORGANISM: Zea mays

<400> SEQUENCE: 28

Met Gly Arg Ser Pro Cys Cys Glu Lys Ala His Thr Asn Lys Gly Ala
1               5                   10                  15

Trp Thr Lys Glu Glu Asp Glu Arg Leu Val Ala His Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60
```

Leu Lys Arg Gly Asn Phe Thr Glu Glu Asp Glu Leu Ile Val Lys
 65                  70                  75                  80

Leu His Ser Val Leu Gly Asn Lys Trp Ser Leu Ile Ala Gly Arg Leu
             85                  90                  95

Pro Gly Arg Thr Asp Asn Glu Ile Lys Asn Tyr Trp Asn Thr His Ile
            100                 105                 110

Arg Arg Lys Leu Leu Ser Arg Gly Ile Asp Pro Val Thr His Arg Pro
        115                 120                 125

Val Thr Glu His His Ala Ser Asn Ile Thr Ile Ser Phe Glu Thr Glu
    130                 135                 140

Val Ala Ala Ala Arg Asp Asp Lys Lys Gly Ala Val Phe Arg Leu
145                 150                 155                 160

Glu Asp Glu Glu Glu Glu Arg Asn Lys Ala Thr Met Val Val Gly
                165                 170                 175

Arg Asp Arg Gln Ser Gln Ser His Ser His Ser His Pro Ala Gly Glu
            180                 185                 190

Trp Gly Gln Gly Lys Arg Pro Leu Lys Cys Pro Asp Leu Asn Leu Asp
        195                 200                 205

Leu Cys Ile Ser Pro Pro Cys Gln Glu Glu Glu Met Glu Ala
    210                 215                 220

Ala Met Arg Val Arg Pro Ala Val Lys Arg Glu Ala Gly Leu Cys Phe
225                 230                 235                 240

Gly Cys Ser Leu Gly Leu Pro Arg Thr Ala Asp Cys Lys Cys Ser Ser
                245                 250                 255

Ser Ser Phe Leu Gly Leu Arg Thr Ala Met Leu Asp Phe Arg Ser Leu
            260                 265                 270

Glu Met Lys
    275

<210> SEQ ID NO 29
<211> LENGTH: 798
<212> TYPE: DNA
<213> ORGANISM: Triticum aestivum

<400> SEQUENCE: 29
atggggaggt cgccgtgctg cgagaaggcg cacaccaaca agggcgcctg gaccaaggag      60
gaggacgacc ggctcaccgc ctacatcaag gcgcacggcg agggctgctg gcgctccctg     120
cccaaggccg cggggttgct ccgctgcggc aagagctgcc gcctccgctg atcaactac      180 ctccgccccg acctcaagcg cggcaacttc agcgatgagg aggacgagct catcatcaag     240
ctccacagcc tcctgggcaa caaatggtct ctgatagccg ggagactccc agggaggacg     300
gacaacgaga tcaagaacta ctggaacacg cacatcagga ggaagctcac gagccggggg     360
atcgacccgg tgacccaccg cgcgatcaac agcgaccacg ccgcgtccaa catcaccata     420
tccttcgaga cggcgcagag ggacgacaag ggcgccgtgt tccggcgaga cgccgagccc     480
accaaggtag cggcagcggc agcggcgatc acccacgtgg accaccatca ccatcaccgt     540
agcaaccccc tccaccagat ggagtggggc aggggaagc cgctcaagtg cccggacctg     600
aacctggacc tctgcatcag cccccgtcc cacgaggacc ccatggtgga caccaagccc     660
gtggtgaaga gggaggccgt cgtgggcctc tgcttcagct gcagcatggg gctccccagg     720
agcgcggact gcaagtgcag cagcttcatg gggctccgga ccgccatgct cgacttcaga     780
agcatcgaga tgaaatga                                                  798

<210> SEQ ID NO 30
<211> LENGTH: 265
<212> TYPE: PRT
<213> ORGANISM: Triticum aestivum

<400> SEQUENCE: 30

Met Gly Arg Ser Pro Cys Cys Glu Lys Ala His Thr Asn Lys Gly Ala
1               5                   10                  15

Trp Thr Lys Glu Glu Asp Asp Arg Leu Thr Ala Tyr Ile Lys Ala His
                20                  25                  30

Gly Glu Gly Cys Trp Arg Ser Leu Pro Lys Ala Ala Gly Leu Leu Arg
            35                  40                  45

Cys Gly Lys Ser Cys Arg Leu Arg Trp Ile Asn Tyr Leu Arg Pro Asp
        50                  55                  60

Leu Lys Arg Gly Asn Phe Ser Asp Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Thr Ser Arg Gly Ile Asp Pro Val Thr His Arg Ala
        115                 120                 125

Ile Asn Ser Asp His Ala Ala Ser Asn Ile Thr Ile Ser Phe Glu Thr
130                 135                 140

Ala Gln Arg Asp Asp Lys Gly Ala Val Phe Arg Arg Asp Ala Glu Pro
145                 150                 155                 160

Thr Lys Val Ala Ala Ala Ala Ile Thr His Val Asp His His
                165                 170                 175

His His His Arg Ser Asn Pro Leu His Gln Met Glu Trp Gly Gln Gly
                180                 185                 190

Lys Pro Leu Lys Cys Pro Asp Leu Asn Leu Asp Leu Cys Ile Ser Pro
            195                 200                 205

Pro Ser His Glu Asp Pro Met Val Asp Thr Lys Pro Val Val Lys Arg
210                 215                 220

Glu Ala Val Val Gly Leu Cys Phe Ser Cys Ser Met Gly Leu Pro Arg
225                 230                 235                 240

Ser Ala Asp Cys Lys Cys Ser Ser Phe Met Gly Leu Arg Thr Ala Met
                245                 250                 255

Leu Asp Phe Arg Ser Ile Glu Met Lys
            260                 265

<210> SEQ ID NO 31
<211> LENGTH: 1210
<212> TYPE: DNA
<213> ORGANISM: Saccharum officinarum

<400> SEQUENCE: 31
cgtggctcac acctcgatcg cagcagcaac aacctccact gccgcccgca acgcaaccca      60
cccgagaggc gaggagggga agaaagcggc ggcggcaaaa ggaccaggaa agcagccaag     120
caagcatcgg tggtgcggtg ccgcccgta gcacctccat catggggagg tcgccgtgct     180
gcgagaaggc gcacaccaac aagggcgcgt ggaccaagga ggaggacgac cgcctcgtgg     240
cgtacatcaa ggcgcacggc gagggtgct ggcgctcgct gcccaaggcc gccggccttc     300
tgcgctgcgg caagagctgc cgcctccggt ggatcaacta cctccggccc gacctcaagc     360
gcggcaactt cacggaagag gaggacgagc tcatcatcaa gctccacagc ctcctcggca     420

-continued

```
acaaatggtc cctgatcgct gggaggctgc cgggcaggac ggacaacgag atcaagaact    480
actggaacac gcacatccgg aggaagctgc tgagcagggg gatcgacccg gtgacccacc    540
gccccatcaa cgagcacacg tccaacataa ccatatcgtt cgaggcggcg gcggcggctg    600
cccgtgaccg tgaggagacg aagggcgccg tcttccggct ggaggagcac aacaaggcgg    660
cggcgatcgg ccgcgatcat cagaaccacc accccgccgc cgagtggggc caggggaagc    720
cgctcaagtg ccccgacctc aacctggacc tctgcatcag cccgccggcg ccgtgccagg    780
aggagaccat ggccatggtg atgaagccgg tgaagcggga ggccgggctc tgcttcagct    840
gcagcctggg gctccccaag agcgccgact gcaagtgcag caacttcctc gggctcagga    900
ccgccatgct cgacttcaga agcctcgaga tgaaatgaac gcttctctct ctctccctct    960
gtaacttccc cctcttcgtt ttgttttgtc accgcacctg gtggatggat gatatttggt   1020
tagtttcgta ggtgaaaata cgtagtagtg agtgagtgaa agagagagaa ggaaaaaaaa   1080
gcgaggattt tgtgccctgg gtcttacctgc tgctctctct tgttgctcca ttccattttg   1140
tctcctcttt ctttctctgt aatgaccatc accaactgat catgggcaat aatacttgct   1200
gcttactaaa                                                          1210

<210> SEQ ID NO 32
<211> LENGTH: 256
<212> TYPE: PRT
<213> ORGANISM: Saccharum officinarum

<400> SEQUENCE: 32

Met Gly Arg Ser Pro Cys Cys Glu Lys Ala His Thr Asn Lys Gly Ala
1               5                   10                  15

Trp Thr Lys Glu Glu Asp Asp Arg Leu Val Ala Tyr Ile Lys Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Ser Arg Gly Ile Asp Pro Val Thr His Arg Pro
        115                 120                 125

Ile Asn Glu His Thr Ser Asn Ile Thr Ile Ser Phe Glu Ala Ala Ala
    130                 135                 140

Ala Ala Ala Arg Asp Arg Glu Glu Thr Lys Gly Ala Val Phe Arg Leu
145                 150                 155                 160

Glu Glu His Asn Lys Ala Ala Ala Ile Gly Arg Asp His Gln Asn His
                165                 170                 175

His Pro Ala Ala Glu Trp Gly Gln Gly Lys Pro Leu Lys Cys Pro Asp
            180                 185                 190

Leu Asn Leu Asp Leu Cys Ile Ser Pro Pro Ala Pro Cys Gln Glu Glu
        195                 200                 205

Thr Met Ala Met Val Met Lys Pro Val Lys Arg Glu Ala Gly Leu Cys
    210                 215                 220
```

Phe Ser Cys Ser Leu Gly Leu Pro Lys Ser Ala Asp Cys Lys Cys Ser
225                 230                 235                 240

Asn Phe Leu Gly Leu Arg Thr Ala Met Leu Asp Phe Arg Ser Leu Glu
            245                 250                 255

<210> SEQ ID NO 33
<211> LENGTH: 777
<212> TYPE: DNA
<213> ORGANISM: Sorghum bicolor

<400> SEQUENCE: 33

```
atgggggcggt cgccgtgctg cgagaaggcg cacacgaaca agggcgcgtg gaccaaggag      60
gaggacgacc gcctggtggc gtacatccgc gcgcacggcg aagggtgctg gcggtcgctg     120
cccaaggcgg ccggactgat gcgctgcggc aagagctgcc gcctccgctg gatcaactac     180
ctccgccccg acctcaagcg cggcaacttc accgccgacg aggacgacct catcatcaag     240
ctgcacagcc tcctcggcaa caagtggtcg ctcatcgccg cgcggctccc ggggcggacg     300
gacaacgaga tcaagaacta ctggaacacg cacatccggc ggaagctgct tggcaggggc     360
atcgaccccg tcacgcaccg ccccatcgcc gacgccggcg ccggcaccgt caccaccatc     420
tcgttccagc ccaacaaacc caacgccgcc gtcgcagcgc aggcgccaca acatcagccg     480
atcaaggcgg tggcgacggc cgtcgttaag gtgcccaggt gccccgacct caacctcgat     540
ctctgcatca gcccgccgtg ccaacagaag gaagacgagg agctggacct caagcccgcc     600
gtcgtcgtca gcggggaggt gctgcaggcc ggccatggcg gcagcctctg cttcggctgc     660
agcctgggca tccaaaaagg agcccccggg tgcagctgca gcagcagcaa cagccaccac     720
cgcttcttgg ggctccggtc cggcatgctc gacttcagag gcctcgagat gaagtga       777
```

<210> SEQ ID NO 34
<211> LENGTH: 258
<212> TYPE: PRT
<213> ORGANISM: Sorghum bicolor

<400> SEQUENCE: 34

Met Gly Arg Ser Pro Cys Cys Glu Lys Ala His Thr Asn Lys Gly Ala
1               5                   10                  15

Trp Thr Lys Glu Glu Asp Asp Arg Leu Val Ala Tyr Ile Arg Ala His
            20                  25                  30

Gly Glu Gly Cys Trp Arg Ser Leu Pro Lys Ala Ala Gly Leu Met Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Ala Asp Glu Asp Asp Leu Ile Ile Lys
65                  70                  75                  80

Leu His Ser Leu Leu Gly Asn Lys Trp Ser Leu Ile Ala Ala Arg Leu
                85                  90                  95

Pro Gly Arg Thr Asp Asn Glu Ile Lys Asn Tyr Trp Asn Thr His Ile
            100                 105                 110

Arg Arg Lys Leu Leu Gly Arg Gly Ile Asp Pro Val Thr His Arg Pro
        115                 120                 125

Ile Ala Asp Ala Gly Ala Gly Thr Val Thr Thr Ile Ser Phe Gln Pro
    130                 135                 140

Asn Lys Pro Asn Ala Ala Val Ala Ala Gln Ala Pro Gln His Gln Pro
145                 150                 155                 160

Ile Lys Ala Val Ala Thr Ala Val Val Lys Val Pro Arg Cys Pro Asp

```
                   165                 170                 175
Leu Asn Leu Asp Leu Cys Ile Ser Pro Pro Cys Gln Gln Lys Glu Asp
            180                 185                 190

Glu Glu Leu Asp Leu Lys Pro Ala Val Val Lys Arg Glu Val Leu
        195                 200                 205

Gln Ala Gly His Gly Gly Ser Leu Cys Phe Gly Cys Ser Leu Gly Ile
        210                 215                 220

Gln Lys Gly Ala Pro Gly Cys Ser Cys Ser Ser Asn Ser His His
225                 230                 235                 240

Arg Phe Leu Gly Leu Arg Ser Gly Met Leu Asp Phe Arg Gly Leu Glu
                245                 250                 255

Met Lys

<210> SEQ ID NO 35
<211> LENGTH: 822
<212> TYPE: DNA
<213> ORGANISM: Zea mays

<400> SEQUENCE: 35
atggggaggt cgccgtgctg cgagaaggcg cacaccaaca agggcgcgtg gaccaaggag      60
gaggacgagc gcctggtcgc gcacatcagg gcgcacggcg aggggtgctg gcgctcgctg     120
cccaaggccg ccggcctcct cgcgtgcggc aagagctgcc gcctccgctg gatcaactac     180
ctccgccccg acctcaagcg cggcaacttc acggaggagg aggacgagct catcgtcaag     240
ctgcacagcg tcctcggcaa caagtggtcc ctgatcgccg gaaggctgcc cggcaggacg     300
gacaacgaga tcaagaacta ctggaacacg cacatccgga ggaagctgct gagcagggggg    360 atcgacccgg tgacgcaccg cccggtcacg gagcaccacg cgtccaacat caccatatcg     420
ttcgagacgg aggtggccgc cgctgcccgt gatgataaga agggcgccgt cttccggctg     480
gaggaggagg aggagcgcaa caaggcgacg atggtcgtcg ccgcgaccg gcagagccag      540 agccagagcc acagccaccc cgccggcgag tggggccagg ggaagaggcc gctcaagtgc     600
cccgacctca acctggacct ctgcatcagc ccgccgtgcc aggaggagga ggagatggag     660
gaggctgcga tgagagtgag accggcggtg aagcggggagg ccgggctctg cttcggctgc    720
agcctggggc tccccaggac cgcggactgc aagtgcagca gcagcagctt cctcgggctc     780
aggaccgcca tgctcgactt cagaagcctc gagatgaaat ga                        822

<210> SEQ ID NO 36
<211> LENGTH: 273
<212> TYPE: PRT
<213> ORGANISM: Zea mays

<400> SEQUENCE: 36

Met Gly Arg Ser Pro Cys Cys Glu Lys Ala His Thr Asn Lys Gly Ala
1                 5                  10                  15

Trp Thr Lys Glu Glu Asp Glu Arg Leu Val Ala His Ile Arg Ala His
                20                  25                  30

Gly Glu Gly Cys Trp Arg Ser Leu Pro Lys Ala Ala Gly Leu Leu Arg
            35                  40                  45

Cys Gly Lys Ser Cys Arg Leu Arg Trp Ile Asn Tyr Leu Arg Pro Asp
        50                  55                  60

Leu Lys Arg Gly Asn Phe Thr Glu Glu Glu Asp Glu Leu Ile Val Lys
65                  70                  75                  80

Leu His Ser Val Leu Gly Asn Lys Trp Ser Leu Ile Ala Gly Arg Leu
```

```
                85                  90                  95
Pro Gly Arg Thr Asp Asn Glu Ile Lys Asn Tyr Trp Asn Thr His Ile
            100                 105                 110
Arg Arg Lys Leu Leu Ser Arg Gly Ile Asp Pro Val Thr His Arg Pro
        115                 120                 125
Val Thr Glu His His Ala Ser Asn Ile Thr Ile Ser Phe Glu Thr Glu
    130                 135                 140
Val Ala Ala Ala Arg Asp Asp Lys Lys Gly Ala Val Phe Arg Leu
145                 150                 155                 160
Glu Glu Glu Glu Glu Arg Asn Lys Ala Thr Met Val Val Gly Arg Asp
                165                 170                 175
Arg Gln Ser Gln Ser Gln Ser His Ser His Pro Ala Gly Glu Trp Gly
            180                 185                 190
Gln Gly Lys Arg Pro Leu Lys Cys Pro Asp Leu Asn Leu Asp Leu Cys
        195                 200                 205
Ile Ser Pro Pro Cys Gln Glu Glu Glu Met Glu Glu Ala Ala Met
    210                 215                 220
Arg Val Arg Pro Ala Val Lys Arg Glu Ala Gly Leu Cys Phe Gly Cys
225                 230                 235                 240
Ser Leu Gly Leu Pro Arg Thr Ala Asp Cys Lys Cys Ser Ser Ser Ser
                245                 250                 255
Phe Leu Gly Leu Arg Thr Ala Met Leu Asp Phe Arg Ser Leu Glu Met
            260                 265                 270
Lys

<210> SEQ ID NO 37
<211> LENGTH: 732
<212> TYPE: DNA
<213> ORGANISM: Oryza sativa

<400> SEQUENCE: 37
atggggaggt caccgtgctg cgagaaggag cacaccaaca agggcgcgtg gaccaaggag     60
gaggacgagc gcctcgtcgc ctacatccgc gcccacggcg agggctgctg gcgctcgctc    120
cccaaggccg ccggcctcct ccgctgcggc aagagctgcc gcctccgctg gatcaactac    180
ctccgccccg acctcaagcg cggcaacttc accgccgacg aggacgacct catcatcaag    240
ctccacagcc tcctcggcaa caagtggtct ctgatcgcgg cgaggctgcc ggggaggacg    300
gacaacgaga tcaagaacta ctggaacacg cacatccgcc ggaagcttct cggcaggggg    360
atcgaccccg tcacgcaccg ccccgtcaac gccgccgccg ccaccatctc cttccatccc    420
cagccgccgc aacgacgaa ggaggagcag ctcatactca gcaagccgcc caagtgcccc    480
gacctcaacc tggacctctg catcagcccg ccgtcgtgcc aggaagaaga cgatgactat    540
gaggcgaagc cggcgatgat cgtgagggcg acggagctgc agcgccgccg cggcggcctc    600
tgcttcggct gcagcctcgg cctccagaag gagtgcaagt gcagcggcgg cggcggcggc    660
gccggcgccg gcaacaactt cctcggcctc agggctggca tgctcgactt cagaagcctc    720
cccatgaaat ga                                                        732

<210> SEQ ID NO 38
<211> LENGTH: 243
<212> TYPE: PRT
<213> ORGANISM: Oryza sativa

<400> SEQUENCE: 38
```

Met Gly Arg Ser Pro Cys Cys Glu Lys Glu His Thr Asn Lys Gly Ala
1               5                   10                  15

Trp Thr Lys Glu Glu Asp Glu Arg Leu Val Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Ala Asp Glu Asp Leu Ile Ile Lys
65                  70                  75                  80

Leu His Ser Leu Leu Gly Asn Lys Trp Ser Leu Ile Ala Ala Arg Leu
                85                  90                  95

Pro Gly Arg Thr Asp Asn Glu Ile Lys Asn Tyr Trp Asn Thr His Ile
            100                 105                 110

Arg Arg Lys Leu Leu Gly Arg Gly Ile Asp Pro Val Thr His Arg Pro
            115                 120                 125

Val Asn Ala Ala Ala Ala Thr Ile Ser Phe His Pro Gln Pro Pro Pro
    130                 135                 140

Thr Thr Lys Glu Glu Gln Leu Ile Leu Ser Lys Pro Lys Cys Pro
145                 150                 155                 160

Asp Leu Asn Leu Asp Leu Cys Ile Ser Pro Ser Cys Gln Glu Glu
                165                 170                 175

Asp Asp Asp Tyr Glu Ala Lys Pro Ala Met Ile Val Arg Ala Thr Glu
            180                 185                 190

Leu Gln Arg Arg Arg Gly Gly Leu Cys Phe Gly Cys Ser Leu Gly Leu
    195                 200                 205

Gln Lys Glu Cys Lys Cys Ser Gly Gly Gly Gly Ala Gly Ala Gly
    210                 215                 220

Asn Asn Phe Leu Gly Leu Arg Ala Gly Met Leu Asp Phe Arg Ser Leu
225                 230                 235                 240

Pro Met Lys

<210> SEQ ID NO 39
<211> LENGTH: 732
<212> TYPE: DNA
<213> ORGANISM: Oryza sativa

<400> SEQUENCE: 39
atggggaggt cgccgtgctg cgagaaggag cacactaaca agggcgcgtg gaccaaggag      60
gaggacgagc gcctcgtcgc ctacatccgc gcccacggcg agggctgctg gcgctcgctc     120
cccaaggccg ccggcctcct ccgctgcggc aagagctgcc gcctccgctg gatcaactac     180
ctccgccccg acctcaagcg cggcaacttc accgccgacg aggacgacct catcatcaag     240
ctccacagcc tcctcggcaa caagtggtct ctgatcgcgg cgaggctgcc ggggaggacg     300
gacaacgaga tcaagaacta ctggaacacg cacatccgcc ggaagcttct cggcagggg     360 atcgaccccg tcacgcaccg ccccgtcaac gccgccgccg ccaccatctc cttccatccc     420
cagccgccgc caacgacgaa ggaggagcag ctcatactca gcaagccgcc caagtgcccc     480
gacctcaacc tggacctctg catcagcccg ccgtcgtgcc aggaagaaga cgatgactat     540
gaggcgaagc cggcgatgat cgtgagggcg ccggagctgc agcgccgccg cggcggcctc     600
tgcttcggct gcagcctcgg cctccagaag gagtgcaagt gcagcggcgg cggcgccggc     660
gccggcgccg gcaacaactt cctcggcctc agggctggca tgctcgactt cagaagcctc     720
cccatgaaat ga                                                    732

<210> SEQ ID NO 40
<211> LENGTH: 243
<212> TYPE: PRT
<213> ORGANISM: Oryza sativa

<400> SEQUENCE: 40

Met Gly Arg Ser Pro Cys Cys Glu Lys Glu His Thr Asn Lys Gly Ala
1               5                   10                  15

Trp Thr Lys Glu Glu Asp Glu Arg Leu Val Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Ala Asp Glu Asp Leu Ile Ile Lys
65                  70                  75                  80

Leu His Ser Leu Leu Gly Asn Lys Trp Ser Leu Ile Ala Ala Arg Leu
                85                  90                  95

Pro Gly Arg Thr Asp Asn Glu Ile Lys Asn Tyr Trp Asn Thr His Ile
            100                 105                 110

Arg Arg Lys Leu Leu Gly Arg Gly Ile Asp Pro Val Thr His Arg Pro
        115                 120                 125

Val Asn Ala Ala Ala Ala Thr Ile Ser Phe His Pro Gln Pro Pro Pro
    130                 135                 140

Thr Thr Lys Glu Glu Gln Leu Ile Leu Ser Lys Pro Pro Lys Cys Pro
145                 150                 155                 160

Asp Leu Asn Leu Asp Leu Cys Ile Ser Pro Pro Ser Cys Gln Glu Glu
                165                 170                 175

Asp Asp Asp Tyr Glu Ala Lys Pro Ala Met Ile Val Arg Ala Pro Glu
            180                 185                 190

Leu Gln Arg Arg Arg Gly Gly Leu Cys Phe Gly Cys Ser Leu Gly Leu
        195                 200                 205

Gln Lys Glu Cys Lys Cys Ser Gly Gly Ala Gly Ala Gly Ala Gly
    210                 215                 220

Asn Asn Phe Leu Gly Leu Arg Ala Gly Met Leu Asp Phe Arg Ser Leu
225                 230                 235                 240

Pro Met Lys

<210> SEQ ID NO 41
<211> LENGTH: 756
<212> TYPE: DNA
<213> ORGANISM: Oryza sativa

<400> SEQUENCE: 41
atggggaggt caccgtgctg cgagaaggca cacaccaaca agggagcatg gaccaaggag      60
gaagatgacc ggctcattgc ctacatcaag gcgcacggcg aaggttgctg gcgatcgctg     120
cccaaggccg ccggcctcct ccgctgtggc aagagctgcc gcctccggtg gatcaactac     180
ctccggcctg acctcaagcg cggcaacttc accgaggagg aggatgagct gatcatcaag     240
cttcacagcc ttttaggcaa caaatggtct ctgatagccg ggaggttgcc aggaagaacg     300
gacaacgaga tcaagaacta ctggaacacg cacatcagga ggaagctgct gagccgtggc     360
atcgacccgg tgacacaccg gccgatcaac gacagcgcgt ccaacatcac catatcattc     420

```
gaggcggccg cggcggcggc gagggacgac aaggccgccg tgttccggcg agaggaccat    480
cctcatcagc cgaaggcggt gacagtggca caggagcagc aggcagccgc cgattgggc     540 catgggaagc cactcaagtg ccctgacctc aatctggacc tctgcatcag cctcccttcc    600
caagaagagc ccatgatgat gaagccggtg aagagggaga ccggcgtctg cttcagctgc    660
agcctggggc tccccaagag cacagactgc aagtgcagca gcttcctggg actcaggaca    720
gccatgctcg acttcagaag cttggaaatg aaatga                              756
```

<210> SEQ ID NO 42
<211> LENGTH: 251
<212> TYPE: PRT
<213> ORGANISM: Oryza sativa

<400> SEQUENCE: 42

```
Met Gly Arg Ser Pro Cys Cys Glu Lys Ala His Thr Asn Lys Gly Ala
1               5                   10                  15

Trp Thr Lys Glu Glu Asp Asp Arg Leu Ile Ala Tyr Ile Lys Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Ser Arg Gly Ile Asp Pro Val Thr His Arg Pro
        115                 120                 125

Ile Asn Asp Ser Ala Ser Asn Ile Thr Ile Ser Phe Glu Ala Ala Ala
    130                 135                 140

Ala Ala Ala Arg Asp Asp Lys Ala Ala Val Phe Arg Arg Glu Asp His
145                 150                 155                 160

Pro His Gln Pro Lys Ala Val Thr Val Ala Gln Glu Gln Gln Ala Ala
                165                 170                 175

Ala Asp Trp Gly His Gly Lys Pro Leu Lys Cys Pro Asp Leu Asn Leu
            180                 185                 190

Asp Leu Cys Ile Ser Leu Pro Ser Gln Glu Glu Pro Met Met Met Lys
        195                 200                 205

Pro Val Lys Arg Glu Thr Gly Val Cys Phe Ser Cys Ser Leu Gly Leu
    210                 215                 220

Pro Lys Ser Thr Asp Cys Lys Cys Ser Ser Phe Leu Gly Leu Arg Thr
225                 230                 235                 240

Ala Met Leu Asp Phe Arg Ser Leu Glu Met Lys
                245                 250
```

<210> SEQ ID NO 43
<211> LENGTH: 786
<212> TYPE: DNA
<213> ORGANISM: Eremochloa ophiuroides

<400> SEQUENCE: 43

```
atggggagag cgccgtgctg cgagaaggcg cacacgaaca agggcgcgtg gaccaaggag    60
gaggacgacc gcctcgtcgc gtacatcaag gcgcacgggg agggctgctg gcgctcgctg    120
```

```
cccaaggccg ccggcctcct gcgctgcggc aagagctgcc gcctccgctg atcaactac       180 ctccgccccg acctcaagcg cggcaacttc acggaggagg aggacgagct catcatcaag       240
ctccacagcc tcctcggcaa caaatggtcc ctgatcgctg gacggctgcc gggcaggacg       300
gacaacgaga tcaagaacta ctggaacacg cacatccgga ggaagctgct gagcaggggg       360
atcgacccgg tgacgcaccg ccccatcaac gagcacgcct cctccaacat aaccatatcg       420
ttcgaggcgg cggcgcccg tgaccgtgac gacaagggcg ccgtcttccg gctggaggag        480
cacaaggcga cggcgatcgg cgcgatcac catcatcatc agaaccacaa ccacagccac         540
cccgccgcca gtggggcca ggggaagccg ctcaagtgcc ccgacctcaa cctggacctc         600
tgcatcagcc cgccgtgcca ggaggaggcg gcggcggcgg ccatggtgat gaagccggtg       660
aagcgggagg ccggcctctg cttcagctgc agcctgggcc tccccaagag cgccgactgc       720
aagtgcagca acttcatcgg cctccggacc gccatgctcg acttcagaag cctcgagatg       780
aaatga                                                                   786
```

```
<210> SEQ ID NO 44
<211> LENGTH: 261
<212> TYPE: PRT
<213> ORGANISM: Eremochloa ophiuroides

<400> SEQUENCE: 44
```

```
Met Gly Arg Ala Pro Cys Cys Glu Lys Ala His Thr Asn Lys Gly Ala
1               5                   10                  15

Trp Thr Lys Glu Glu Asp Asp Arg Leu Val Ala Tyr Ile Lys Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Ser Arg Gly Ile Asp Pro Val Thr His Arg Pro
        115                 120                 125

Ile Asn Glu His Ala Ser Ser Asn Ile Thr Ile Ser Phe Glu Ala Ala
    130                 135                 140

Ala Ala Arg Asp Arg Asp Asp Lys Gly Ala Val Phe Arg Leu Glu Glu
145                 150                 155                 160

His Lys Ala Thr Ala Ile Gly Arg Asp His His His Gln Asn His
            165                 170                 175

Asn His Ser His Pro Ala Ala Glu Trp Gly Gln Gly Lys Pro Leu Lys
        180                 185                 190

Cys Pro Asp Leu Asn Leu Asp Leu Cys Ile Ser Pro Pro Cys Gln Glu
    195                 200                 205

Glu Ala Ala Ala Ala Met Val Met Lys Pro Val Lys Arg Glu Ala
210                 215                 220

Gly Leu Cys Phe Ser Cys Ser Leu Gly Leu Pro Lys Ser Ala Asp Cys
225                 230                 235                 240

Lys Cys Ser Asn Phe Ile Gly Leu Arg Thr Ala Met Leu Asp Phe Arg
```

```
                       245                 250                 255

Ser Leu Glu Met Lys
                260

<210> SEQ ID NO 45
<211> LENGTH: 795
<212> TYPE: DNA
<213> ORGANISM: Gossypium hirsutum

<400> SEQUENCE: 45
atgggaaggt ctccttgttg tgagaaagct catacgaaca aggtgcgtg gactaaagaa      60 gaagatgatc gcctcatagc ttacatccga gcccatggtg aaggttgctg gcgttcactc     120
cctaaagctg ctggccttct ccgctgtggc aaaagttgta gacttcgttg gatcaattac     180
ttaagacctg atcttaaacg tggcaatttc actgaagaag aagatgagct cattatcaag     240
ctgcacagcc ttcttggtaa caagtggtct cttatagcgg ggagattacc aggaagaaca     300
gataatgaga ttaagaatta ctggaacacg catataagaa ggaagctatt gagcagaggt     360
attgatccag caactcacag gccactcaat gaggcttctc aggatgtaac aacaatatct     420
ttcagtggtg ccaaagaaga aaagagaag attaatacta acagtaataa taaccctatt      480
ggatttatca ccaaagatga aagaaaatc ccagttcaag aaaggtgtcc agacttgaat       540
ttggacctca gaattagccc tcctattac cagcaaaccc aaccagagtc attcaaaact       600
ggaggaagaa ctctttgttt tatttgcagc ttgggagtta aaaacagcaa agattgcact     660
tgcagcacca tcactactgc tgcaggtagc agcagcagca gcagtagcca cagcaacagc     720
aacaacagca gtggttatga tttcttaggc ttgaaatctg gtatcttgga atatagaagt     780
ttggaaatga aataa                                                      795

<210> SEQ ID NO 46
<211> LENGTH: 264
<212> TYPE: PRT
<213> ORGANISM: Gossypium hirsutum

<400> SEQUENCE: 46

Met Gly Arg Ser Pro Cys Cys Glu Lys Ala His Thr Asn Lys Gly Ala
1               5                  10                  15

Trp Thr Lys Glu Glu Asp Asp Arg Leu Ile Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Ser Arg Gly Ile Asp Pro Ala Thr His Arg Pro
        115                 120                 125

Leu Asn Glu Ala Ser Gln Asp Val Thr Thr Ile Ser Phe Ser Gly Ala
    130                 135                 140

Lys Glu Glu Lys Glu Lys Ile Asn Thr Asn Ser Asn Asn Asn Pro Ile
145                 150                 155                 160
```

```
Gly Phe Ile Thr Lys Asp Glu Lys Lys Ile Pro Val Gln Glu Arg Cys
                165                 170                 175

Pro Asp Leu Asn Leu Asp Leu Arg Ile Ser Pro Tyr Tyr Gln Gln
        180                 185                 190

Thr Gln Pro Glu Ser Phe Lys Thr Gly Gly Arg Thr Leu Cys Phe Ile
        195                 200                 205

Cys Ser Leu Gly Val Lys Asn Ser Lys Asp Cys Thr Cys Ser Thr Ile
        210                 215                 220

Thr Thr Ala Ala Gly Ser Ser Ser Ser Ser His Ser Asn Ser
225                 230                 235                 240

Asn Asn Ser Ser Gly Tyr Asp Phe Leu Gly Leu Lys Ser Gly Ile Leu
                245                 250                 255

Glu Tyr Arg Ser Leu Glu Met Lys
                260
```

<210> SEQ ID NO 47
<211> LENGTH: 693
<212> TYPE: DNA
<213> ORGANISM: Salvia miltiorrhiza

<400> SEQUENCE: 47

```
atgggaaggg ctccatgctg tgagaaagct cacacaaaca aggggcgtg gactaaggaa        60
gaagacgatc ggctggtggc ctacatccgc gcccacggcg agggatgctg gcgctcgctc      120
cctaaggccg ccgggctcct ccgctgcggc aagagctgcc gcctccgctg gatcaactac      180
ctccgccccg atctcaagag aggcaacttc accgaagaag aagacgaact catcatcaaa      240
ctccatagcc ttctgggcaa caatggtct cttattgctg ggagattgcc ggggcggacg       300
gacaacgaga tcaagaacta ctggaacacg cacatcagaa gaaagctggt gagccgaggc      360
attgatccca ctacgcatcg ccccatcaat gaggctgagg ctcagcctgc cacaaccatt      420
tcttttaatt catcaaacaa attattaggg aaggaagaga ggtgcagccc taagtgcccc      480
gatttgaatc ttgacctcag aatcagccct ccccatcaac aagaacccctt caaaacaggt    540
actagtagtc gtagtagtac cttgtgcttc gcttgtagtc tcggcatcca aaacagcaaa     600
gattgcagct gtacaaatac cactaattct ggattcgatt ttctgggatt gaaatctggc    660
gttttggatt acagaagatt ggagatgaaa tga                                    693
```

<210> SEQ ID NO 48
<211> LENGTH: 230
<212> TYPE: PRT
<213> ORGANISM: Salvia miltiorrhiza

<400> SEQUENCE: 48

```
Met Gly Arg Ala Pro Cys Cys Glu Lys Ala His Thr Asn Lys Gly Ala
1               5                   10                  15

Trp Thr Lys Glu Glu Asp Asp Arg Leu Val Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95
```

Pro Gly Arg Thr Asp Asn Glu Ile Lys Asn Tyr Trp Asn Thr His Ile
            100                 105                 110

Arg Arg Lys Leu Val Ser Arg Gly Ile Asp Pro Thr Thr His Arg Pro
        115                 120                 125

Ile Asn Glu Ala Glu Ala Gln Pro Ala Thr Thr Ile Ser Phe Asn Ser
    130                 135                 140

Ser Asn Lys Leu Leu Gly Lys Glu Glu Arg Cys Ser Pro Lys Cys Pro
145                 150                 155                 160

Asp Leu Asn Leu Asp Leu Arg Ile Ser Pro Pro His Gln Gln Glu Pro
                165                 170                 175

Phe Lys Thr Gly Thr Ser Ser Arg Ser Ser Thr Leu Cys Phe Ala Cys
        180                 185                 190

Ser Leu Gly Ile Gln Asn Ser Lys Asp Cys Ser Cys Thr Asn Thr Thr
        195                 200                 205

Asn Ser Gly Phe Asp Phe Leu Gly Leu Lys Ser Gly Val Leu Asp Tyr
    210                 215                 220

Arg Arg Leu Glu Met Lys
225                 230

<210> SEQ ID NO 49
<211> LENGTH: 768
<212> TYPE: DNA
<213> ORGANISM: Malus domestica

<400> SEQUENCE: 49
atgggaagat ctccttgctg tgagaaggct cacaccaaca aaggagcttg gaccaaggaa      60
gaagacgacc gcctcattgc ctacatcaga gctcacggcg agggttgctg gcggtcactg     120
cccaaggcgg cgggcctcct ccgatgcggg aagagctgca ggctgcggtg atcaactac     180 cttagacctg atctcaagcg tggcaatttc actgaagaag aagatgagct catcatcaaa     240
ctccatagcc tcctcggaaa caatggtct tgatagctg aaggctgcc tggaagaaca        300 gacaatgaga taagaacta ctggaacacc acataagaa ggaagctttt gaccagaggg       360
attgacccca caactcacag gccactcaac gagacacctc aggaatctgc aaccacaatt     420
tcttttgctg ccgcttctgc aaatatcaaa gaagaagata aaaaaatctc cataaccaat     480
gggcttgttt gcaaagattc aaaaaaccca gttcaggaaa ggtgccctga cttgaatctt     540
gaccttcaaa tcagccctcc ctgccagcct cagcaaccca gtgacggttt gaagagtgga     600
gggcggggac tctgctttc ttgcagtttg gggcttcaag atgcaaagaa ctgcagctgt      660
gggagggatg ctattggtgg cgccaccagt ggcaccacca atattggtta tgatttcttg     720
gggttgaaaa atgggtctt ggattacaga agcttggaga tgaaatga                   768

<210> SEQ ID NO 50
<211> LENGTH: 255
<212> TYPE: PRT
<213> ORGANISM: Malus domestica

<400> SEQUENCE: 50

Met Gly Arg Ser Pro Cys Cys Glu Lys Ala His Thr Asn Lys Gly Ala
1               5                   10                  15

Trp Thr Lys Glu Glu Asp Asp Arg Leu Ile Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp

```
            50                  55                  60
Leu Lys Arg Gly Asn Phe Thr Glu Glu Asp Glu Leu Ile Ile Lys
 65                  70                  75                  80

Leu His Ser Leu Leu Gly Asn Lys Trp Ser Leu Ile Ala Gly Arg Leu
                 85                  90                  95

Pro Gly Arg Thr Asp Asn Glu Ile Lys Asn Tyr Trp Asn Thr His Ile
             100                 105                 110

Arg Arg Lys Leu Leu Thr Arg Gly Ile Asp Pro Thr Thr His Arg Pro
         115                 120                 125

Leu Asn Glu Thr Pro Gln Glu Ser Ala Thr Thr Ile Ser Phe Ala Ala
     130                 135                 140

Ala Ser Ala Asn Ile Lys Glu Glu Asp Lys Lys Ile Ser Ile Thr Asn
145                 150                 155                 160

Gly Leu Val Cys Lys Asp Ser Lys Asn Pro Val Gln Glu Arg Cys Pro
                165                 170                 175

Asp Leu Asn Leu Asp Leu Gln Ile Ser Pro Pro Cys Gln Pro Gln Gln
            180                 185                 190

Pro Ser Asp Gly Leu Lys Ser Gly Arg Gly Leu Cys Phe Ser Cys
        195                 200                 205

Ser Leu Gly Leu Gln Asp Ala Lys Asn Cys Ser Cys Gly Arg Asp Ala
    210                 215                 220

Ile Gly Gly Ala Thr Ser Gly Thr Thr Asn Ile Gly Tyr Asp Phe Leu
225                 230                 235                 240

Gly Leu Lys Asn Gly Val Leu Asp Tyr Arg Ser Leu Glu Met Lys
                245                 250                 255

<210> SEQ ID NO 51
<211> LENGTH: 807
<212> TYPE: DNA
<213> ORGANISM: Populus trichocarpa

<400> SEQUENCE: 51
atgggaaggt ctccttgctg tgaaaaagct catacaaaca aaggcgcatg gactaaggaa      60
gaagatgatc gccttattgc ttacattaga acccacggtg aaggttgctg gcgttcactt     120
cctaaagctg ctggccttct aagatgcggc aagagctgca gacttcgttg gatcaactat     180
ttaagacctg accttaaacg tggcaattt actgaagaag aagatgagct cattatcaaa     240
ctccatagtc tcctcggcaa caaatggtca cttatagccg gaaggttacc agggagaaca     300
gataatgaga taagaattat tggaacacac atataagaa ggaagctctt gaatagaggc     360
atagatcctg cgactcatag gccactcaat gaaccagccc aagaagcttc aacaacaata     420
tctttcagca ctactacctc agttaaagaa gagtcgttga gttctgttaa agaggaaagt     480
aataaggaga agataattag cgcagctgct tttatatgca aagaagagaa aaccccagtt     540
caagaaaggt gtccagactt gaatcttgaa cttagaatta gccttccttg ccaaaaccag     600
cctgatcgtc accaggcatt caaaactgga ggaagtacaa gtctttgttt tgcttgcagc     660
ttggggctac aaaacagcaa ggattgcagt tgcagtgtca ttgtgggtac tattggaagc     720
agcagtagtg ctggctccaa aactggctat gacttcttag ggatgaaaag tggtgtgttg     780
gattatagag gtttggagat gaaatga                                        807

<210> SEQ ID NO 52
<211> LENGTH: 268
<212> TYPE: PRT
<213> ORGANISM: Populus trichocarpa
```

<400> SEQUENCE: 52

Met Gly Arg Ser Pro Cys Cys Glu Lys Ala His Thr Asn Lys Gly Ala
1               5                   10                  15

Trp Thr Lys Glu Glu Asp Asp Arg Leu Ile Ala Tyr Ile Arg Thr His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
50                  55                  60

Leu Lys Arg Gly Asn Phe Thr Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Asn Arg Gly Ile Asp Pro Ala Thr His Arg Pro
        115                 120                 125

Leu Asn Glu Pro Ala Gln Glu Ala Ser Thr Thr Ile Ser Phe Ser Thr
130                 135                 140

Thr Thr Ser Val Lys Glu Glu Ser Leu Ser Ser Val Lys Glu Glu Ser
145                 150                 155                 160

Asn Lys Glu Lys Ile Ile Ser Ala Ala Ala Phe Ile Cys Lys Glu Glu
                165                 170                 175

Lys Thr Pro Val Gln Glu Arg Cys Pro Asp Leu Asn Leu Glu Leu Arg
            180                 185                 190

Ile Ser Leu Pro Cys Gln Asn Gln Pro Asp Arg His Gln Ala Phe Lys
        195                 200                 205

Thr Gly Gly Ser Thr Ser Leu Cys Phe Ala Cys Ser Leu Gly Leu Gln
210                 215                 220

Asn Ser Lys Asp Cys Ser Cys Ser Val Ile Val Gly Thr Ile Gly Ser
225                 230                 235                 240

Ser Ser Ser Ala Gly Ser Lys Thr Gly Tyr Asp Phe Leu Gly Met Lys
                245                 250                 255

Ser Gly Val Leu Asp Tyr Arg Gly Leu Glu Met Lys
            260                 265

<210> SEQ ID NO 53
<211> LENGTH: 816
<212> TYPE: DNA
<213> ORGANISM: Populus trichocarpa

<400> SEQUENCE: 53
atgggaaggt ctccttgctg tgaaaaagcc catacaaaca agggtgcgtg gaccaaggag      60
gaagacgatc gccttgttgc ttacattaga gctcacggtg aaggttgctg gcgctcactt     120
cctaaagccg ctggccttct tagatgtggc aagagttgca gacttcgttg gatcaactat     180
ttaagacctg accttaaacg tggcaatttc accgaagcag aagatgagct cattatcaaa     240
ctccatagcc tccttggaaa caatggtca ctcatagctg gaagattacc agggagaaca     300
gataatgaga taagaattat tggaacaca catataagaa ggaagctttt gaacagaggc     360
atagatcccg caactcatag gccactcaac gaaccagcag tacaagaagc cacaacaaca     420
atatctttca ccacgactac tacttcagta cttgaagaag agtctctggg ttctataatt     480
aaagaggaaa ataaagagaa gataattagc gcaactgctt tcgtatgcaa agaagagaaa     540

```
acccaagttc aagaaaggtg tccagacttg aatctcgagc ttggaattag ccttccttcc      600
caaaaccagc ctgatcatca ccagccattc aaaactggag gaagtagaag tctttgtttt     660
gcttgcagtt tggggctaca aaacagcaag gattgcagct gcaatgttat tgtgagcact     720
gttgggagca gtggcagcac tagcacaaag actggttatg acttcttggg catgaaaagt     780
ggtgttttgg attatagaag tttagagatg aaataa                               816
```

<210> SEQ ID NO 54
<211> LENGTH: 271
<212> TYPE: PRT
<213> ORGANISM: Populus trichocarpa

<400> SEQUENCE: 54

```
Met Gly Arg Ser Pro Cys Cys Glu Lys Ala His Thr Asn Lys Gly Ala
1               5                   10                  15

Trp Thr Lys Glu Glu Asp Asp Arg Leu Val Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Ala Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Asn Arg Gly Ile Asp Pro Ala Thr His Arg Pro
        115                 120                 125

Leu Asn Glu Pro Ala Val Gln Glu Ala Thr Thr Thr Ile Ser Phe Thr
    130                 135                 140

Thr Thr Thr Thr Ser Val Leu Glu Glu Glu Ser Leu Gly Ser Ile Ile
145                 150                 155                 160

Lys Glu Glu Asn Lys Glu Lys Ile Ile Ser Ala Thr Ala Phe Val Cys
                165                 170                 175

Lys Glu Glu Lys Thr Gln Val Gln Glu Arg Cys Pro Asp Leu Asn Leu
            180                 185                 190

Glu Leu Gly Ile Ser Leu Pro Ser Gln Asn Gln Pro Asp His His Gln
        195                 200                 205

Pro Phe Lys Thr Gly Gly Ser Arg Ser Leu Cys Phe Ala Cys Ser Leu
    210                 215                 220

Gly Leu Gln Asn Ser Lys Asp Cys Ser Cys Asn Val Ile Val Ser Thr
225                 230                 235                 240

Val Gly Ser Ser Gly Ser Thr Ser Thr Lys Thr Gly Tyr Asp Phe Leu
                245                 250                 255

Gly Met Lys Ser Gly Val Leu Asp Tyr Arg Ser Leu Glu Met Lys
            260                 265                 270
```

<210> SEQ ID NO 55
<211> LENGTH: 813
<212> TYPE: DNA
<213> ORGANISM: Populus tremula x Populus tremuloides

<400> SEQUENCE: 55

```
atgggaaggt ctccttgctg tgaaaaagcc catacaaaca agggtgcgtg gaccaaggag      60
```

```
gaagacgatc gccttgttgc ttacattaga gctcatggtg aaggttgctg gcgttcactt    120
cctaaagccg ctggccttct tagatgtggc aagagttgca gacttcgctg atcaactac    180 ttacgacctg accttaaacg tggcaatttc accgaagcag aagatgagct cattatcaaa    240
ctccatagcc tccttggaaa cagtagatgg tcactcatag ctggaagatt accagggaga    300
acagataatg agataaagaa ttattggaac acacatataa gaaggaagct tttgaacaga    360
ggcatagatc ccgcaactca taggccactc aacgaaccgg tacaggaagc acaacgaca    420 atatctttca ccacaaccac tacttcagtt gaagaagagt ctcggggttc tataattaaa    480
gaggaaatta aagagaagtt aattagcgca actgctttcg tatgcacaga agcgaaaacc    540
caagttcaag aaaggtgtcc agacttgaat ctcgaacttg aattagcct tcttcccaa    600 aaccagcctg atcatcacca gccattcaag accggaggaa gtagaagtct ttgttttgct    660
tgcagtttgg ggctacaaaa cagcaaggat tgcagctgca atgttattgt gagcactgtt    720
gggagcagtg gcagcactag cacaaagaat ggctatgact tcttgggcat gaaaagtggt    780
gttttggatt atagaagttt agagatgaaa taa                                  813
```

<210> SEQ ID NO 56
<211> LENGTH: 270
<212> TYPE: PRT
<213> ORGANISM: Populus tremula x Populus tremuloides

<400> SEQUENCE: 56

```
Met Gly Arg Ser Pro Cys Cys Glu Lys Ala His Thr Asn Lys Gly Ala
1               5                   10                  15

Trp Thr Lys Glu Glu Asp Asp Arg Leu Val Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Ala Glu Asp Glu Leu Ile Ile Lys
65                  70                  75                  80

Leu His Ser Leu Leu Gly Asn Ser Arg Trp Ser Leu Ile Ala Gly Arg
                85                  90                  95

Leu Pro Gly Arg Thr Asp Asn Glu Ile Lys Asn Tyr Trp Asn Thr His
            100                 105                 110

Ile Arg Arg Lys Leu Leu Asn Arg Gly Ile Asp Pro Ala Thr His Arg
        115                 120                 125

Pro Leu Asn Glu Pro Val Gln Glu Ala Thr Thr Ile Ser Phe Thr
    130                 135                 140

Thr Thr Thr Thr Ser Val Glu Glu Glu Ser Arg Gly Ser Ile Ile Lys
145                 150                 155                 160

Glu Glu Ile Lys Glu Lys Leu Ile Ser Ala Thr Ala Phe Val Cys Thr
                165                 170                 175

Glu Ala Lys Thr Gln Val Gln Glu Arg Cys Pro Asp Leu Asn Leu Glu
            180                 185                 190

Leu Gly Ile Ser Leu Pro Ser Gln Asn Gln Pro Asp His His Gln Pro
        195                 200                 205

Phe Lys Thr Gly Gly Ser Arg Ser Leu Cys Phe Ala Cys Ser Leu Gly
    210                 215                 220

Leu Gln Asn Ser Lys Asp Cys Ser Cys Asn Val Ile Val Ser Thr Val
225                 230                 235                 240
```

Gly Ser Ser Gly Ser Thr Ser Thr Lys Asn Gly Tyr Asp Phe Leu Gly
                245                 250                 255

Met Lys Ser Gly Val Leu Asp Tyr Arg Ser Leu Glu Met Lys
        260                 265                 270

<210> SEQ ID NO 57
<211> LENGTH: 735
<212> TYPE: DNA
<213> ORGANISM: Solenostemon scutellarioides

<400> SEQUENCE: 57

```
atgatgggaa ggtctccgtg ctgtgagaaa gctcacacaa acaaggggc atggactaaa      60
gaagaagacg atcggctcat ctcctacatc cgcgctcacg gcgagggatg ctggcggtct     120
cttcctaagg cagctggcct cctccgctgc ggcaagagct gccgcctgcg ctggatcaac     180
tacttgcgcc cggatctcaa gagaggcaac ttcacagaag acgaagacga actcatcatc     240
aaactccaca gccttctagg caacaaatgg tctcttatag ccggaaggct gccgggggcga    300
accgacaacg agatcaagaa ctactggaac actcacatca aagaaaaact ggtgagccaa     360
ggaatcgatc caacgacgca tcgccccatc aatgagcctg ctgcagctgc agctgcacca     420
caggaggaag cagtatcgaa aaccatttcc ttctcccaat cggagagaat cgacaagtgc     480
ccggatttga atcttgatct cagaatcagc cccccatcat catcccagca gcaaaatcaa     540
gaaccgttga aaacaggtac gagtagtggt agtagtagta ccttgtgctt cgcatgtagc     600
atcggcatcc aaaacagcaa ggattgcagc tgcagagacg gaatcatgat cagtgtgagt     660
gggagcagct ctggatatga ttttctgggg ttgaaagcgg gagttttgga ttacagaagc     720
ttggagatga aatga                                                      735
```

<210> SEQ ID NO 58
<211> LENGTH: 244
<212> TYPE: PRT
<213> ORGANISM: Solenostemon scutellarioides

<400> SEQUENCE: 58

Met Met Gly Arg Ser Pro Cys Cys Glu Lys Ala His Thr Asn Lys Gly
1               5                  10                  15

Ala Trp Thr Lys Glu Glu Asp Asp Arg Leu Ile Ser Tyr Ile Arg Ala
            20                  25                  30

His Gly Glu Gly Cys Trp Arg Ser Leu Pro Lys Ala Ala Gly Leu Leu
        35                  40                  45

Arg Cys Gly Lys Ser Cys Arg Leu Arg Trp Ile Asn Tyr Leu Arg Pro
    50                  55                  60

Asp Leu Lys Arg Gly Asn Phe Thr Glu Asp Glu Asp Glu Leu Ile Ile
65                  70                  75                  80

Lys Leu His Ser Leu Leu Gly Asn Lys Trp Ser Leu Ile Ala Gly Arg
                85                  90                  95

Leu Pro Gly Arg Thr Asp Asn Glu Ile Lys Asn Tyr Trp Asn Thr His
            100                 105                 110

Ile Arg Arg Lys Leu Val Ser Gln Gly Ile Asp Pro Thr Thr His Arg
        115                 120                 125

Pro Ile Asn Glu Pro Ala Ala Ala Ala Ala Pro Gln Glu Glu Ala
    130                 135                 140

Val Ser Lys Thr Ile Ser Phe Ser Gln Ser Glu Arg Ile Asp Lys Cys
145                 150                 155                 160

```
Pro Asp Leu Asn Leu Asp Leu Arg Ile Ser Pro Ser Ser Ser Gln
            165                 170                 175
Gln Gln Asn Gln Glu Pro Leu Lys Thr Gly Thr Ser Ser Gly Ser Ser
        180                 185                 190
Ser Thr Leu Cys Phe Ala Cys Ser Ile Gly Ile Gln Asn Ser Lys Asp
        195                 200                 205
Cys Ser Cys Arg Asp Gly Ile Met Ile Ser Val Ser Gly Ser Ser Ser
    210                 215                 220
Gly Tyr Asp Phe Leu Gly Leu Lys Ala Gly Val Leu Asp Tyr Arg Ser
225                 230                 235                 240
Leu Glu Met Lys
```

<210> SEQ ID NO 59
<211> LENGTH: 858
<212> TYPE: DNA
<213> ORGANISM: Medicago truncatula

<400> SEQUENCE: 59

```
tcatttcatt tctaagcctt tgtaatccca aacaccacct ttcaaaccca agaaatcata      60
agcaggtgca gtggaaccat ttccactgct agaatttcca acaatttcat cacaggtaca     120
atccttacta ttctgcaaac ccaaactaca aacaaaacag agattgttcc tttctctgtt     180
tctgaattgt tcatcatgtt cttgaacacg tggtggacta attgttaact caagattcaa     240
atcaggacaa cgttctaaca ccaacccttt aaccatgttt gtgttcattt cttgatgatg     300
atgatgatga tgatattgtt cttgtttaat ggatgatgca aaagatatag ttgttggtag     360
ggttttgta gctgtaggag ttgatgtaga tgctgctaca gctatagtaa cagcttcttg     420
attttgaaga tgaagagttc gagattgtga ttgagaatga gaaacttcgt ttaaaggcct     480
atgagtagca gggtcaattc ctctattcaa aagctttctt cttatatgag tgttccaata     540
attctttatc tcattatctg ttcttcctgg taatcttcca gctatcaaag accatttgtt     600
accaagaaga ctatggagtt tgatgatgag ttcatcttct tcttctgtaa agttaccacg     660
tttaaggtct ggcctgagat agttaatcca ccggagacga caacttttac cacatcggag     720
taagccagct gctttaggga gagatctcca acaaccttca ccatgtgccc taatatatga     780
tataagtcta tcatcttctt cttttgtcca agctcctttg tttgtatgag cttttcaca     840
acaaggtgat cttcccat                                                  858
```

<210> SEQ ID NO 60
<211> LENGTH: 285
<212> TYPE: PRT
<213> ORGANISM: Medicago truncatula

<400> SEQUENCE: 60

```
Met Gly Arg Ser Pro Cys Cys Glu Lys Ala His Thr Asn Lys Gly Ala
1               5                   10                  15
Trp Thr Lys Glu Glu Asp Asp Arg Leu Ile Ser Tyr Ile Arg Ala His
            20                  25                  30
Gly Glu Gly Cys Trp Arg Ser Leu Pro Lys Ala Ala Gly Leu Leu Arg
        35                  40                  45
Cys Gly Lys Ser Cys Arg Leu Arg Trp Ile Asn Tyr Leu Arg Pro Asp
    50                  55                  60
Leu Lys Arg Gly Asn Phe Thr Glu Glu Glu Asp Glu Leu Ile Ile Lys
65                  70                  75                  80
Leu His Ser Leu Leu Gly Asn Lys Trp Ser Leu Ile Ala Gly Arg Leu
```

```
                    85                  90                  95
Pro Gly Arg Thr Asp Asn Glu Ile Lys Asn Tyr Trp Asn Thr His Ile
                100                 105                 110
Arg Arg Lys Leu Leu Asn Arg Gly Ile Asp Pro Ala Thr His Arg Pro
            115                 120                 125
Leu Asn Glu Val Ser His Ser Gln Ser Gln Ser Arg Thr Leu His Leu
        130                 135                 140
Gln Asn Gln Glu Ala Val Thr Ile Ala Val Ala Ser Thr Ser Thr
145                 150                 155                 160
Pro Thr Ala Thr Lys Thr Leu Pro Thr Thr Ile Ser Phe Ala Ser Ser
                165                 170                 175
Ile Lys Gln Glu Gln Tyr His His His His His Gln Glu Met Asn
            180                 185                 190
Thr Asn Met Val Lys Gly Leu Val Leu Glu Arg Cys Pro Asp Leu Asn
        195                 200                 205
Leu Glu Leu Thr Ile Ser Pro Pro Arg Val Gln Glu His Asp Glu Gln
        210                 215                 220
Phe Arg Asn Arg Glu Arg Asn Asn Leu Cys Phe Val Cys Ser Leu Gly
225                 230                 235                 240
Leu Gln Asn Ser Lys Asp Cys Thr Cys Asp Glu Ile Val Gly Asn Ser
                245                 250                 255
Ser Ser Gly Asn Gly Ser Thr Ala Pro Ala Tyr Asp Phe Leu Gly Leu
            260                 265                 270
Lys Gly Gly Val Trp Asp Tyr Lys Gly Leu Glu Met Lys
            275                 280                 285

<210> SEQ ID NO 61
<211> LENGTH: 858
<212> TYPE: DNA
<213> ORGANISM: Medicago truncatula

<400> SEQUENCE: 61
atgggaagat caccttgttg tgaaaaagct catacaaaca aaggagcttg acaaaagaa      60 gaagatgata gacttatatc atatattagg gcacatggtg aaggttgttg gagatctctc    120
cctaaagcag ctggcttact ccgatgtggt aaaagttgtc gtctccggtg gattaactat    180
ctcaggccag accttaaacg tggtaacttt acagaagaag aagatgaact catcatcaaa    240
ctccatagtc ttcttggtaa caaatggtct ttgatagctg gaagattacc aggaagaaca    300
gataatgaga taagaattaa ttggaacact catataagaa gaaagctttt gaatagagga    360
attgaccctg ctactcatag gcctttaaac gaagtttctc attctcaatc acaatctcaa    420
actcttcatc ttcaaaatca gaagctgtt actatagctg tagcagcatc tacatcaact    480
cctacagcta caaaaaccct accaacaact atatcttttg catcatccat taaacaagaa    540
caatatcatc atcatcatca tcatcaagaa atgaacacaa acatggttaa agggttggtg    600
ttagaacgtt gtcctgattt gaatcttgag ttaacaatta gtccaccacg tgttcaagaa    660
catgatgaac aattcagaaa cagagaaagg aacaatctct gttttgtttg tagtttgggt    720
ttgcagaata gtaaggattg tacctgtgat gaaattgttg gaaattctag cagtggaaat    780
ggttccactg cacctgctta tgatttcttg ggtttgaaag gtggtgtttg ggattacaaa    840
ggcttagaaa tgaaatga                                                   858

<210> SEQ ID NO 62
<211> LENGTH: 285
```

<212> TYPE: PRT
<213> ORGANISM: Medicago truncatula

<400> SEQUENCE: 62

Met Gly Arg Ser Pro Cys Cys Glu Lys Ala His Thr Asn Lys Gly Ala
1               5                   10                  15

Trp Thr Lys Glu Glu Asp Asp Arg Leu Ile Ser Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Asn Arg Gly Ile Asp Pro Ala Thr His Arg Pro
        115                 120                 125

Leu Asn Glu Val Ser His Ser Gln Ser Gln Ser Gln Thr Leu His Leu
    130                 135                 140

Gln Asn Gln Glu Ala Val Thr Ile Ala Val Ala Ala Ser Thr Ser Thr
145                 150                 155                 160

Pro Thr Ala Thr Lys Thr Leu Pro Thr Thr Ile Ser Phe Ala Ser Ser
                165                 170                 175

Ile Lys Gln Glu Gln Tyr His His His His His Gln Glu Met Asn
            180                 185                 190

Thr Asn Met Val Lys Gly Leu Val Leu Glu Arg Cys Pro Asp Leu Asn
        195                 200                 205

Leu Glu Leu Thr Ile Ser Pro Pro Arg Val Gln Glu His Asp Glu Gln
    210                 215                 220

Phe Arg Asn Arg Glu Arg Asn Asn Leu Cys Phe Val Cys Ser Leu Gly
225                 230                 235                 240

Leu Gln Asn Ser Lys Asp Cys Thr Cys Asp Glu Ile Val Gly Asn Ser
                245                 250                 255

Ser Ser Gly Asn Gly Ser Thr Ala Pro Ala Tyr Asp Phe Leu Gly Leu
            260                 265                 270

Lys Gly Gly Val Trp Asp Tyr Lys Gly Leu Glu Met Lys
        275                 280                 285

<210> SEQ ID NO 63
<211> LENGTH: 756
<212> TYPE: DNA
<213> ORGANISM: Vitis vinifera

<400> SEQUENCE: 63
atggggaggt ctccttgctg tgagaaagct catacaaaca aaggggcatg gaccaaggag      60
gaagatgatc gcctcatcgc ttatatccgg gcacacggcg agggctgctg gaggtctctc    120
cccaaggccg caggccttct ccgatgtggg aaaagttgcc gctccgatg gataaactac     180 ctgaggcctg acctcaagcg gggaaacttc accgaggaag aagatgaact catcatcaaa    240
ctgcatagtc tccttggcaa caatggtct cttatagctg ggagattacc aggaagaaca     300
gataatgaaa taagaatta ctggaacacc cacatacgga gaaagcttct gaaccgaggc     360

-continued

```
atcgatccgt ctactcatcg ccccatcaac gagccctcac cggacgttac aaccatatct    420
ttcgcagccg cagttaagga agaggagaag atcaatatca gcagtactgg tggatttggg    480
tgcaaaactg agaaaaaccc agttacggaa aagtgtccag acctcaacct tgagctcaga    540
atcagcccac cataccaacc ccaagctgag acgccattga agactggtgg gaggagtagc    600
agcactactc tttgctttgc atgcagtttg gaataccaa atagtgagga gtgcagttgc    660
agtattggta ctagtagtgg aagcagcagc tctgggtatg acttcttagg gttgacatct    720
ggggttttgg attacagagg tttggagatg aaataa                              756
```

<210> SEQ ID NO 64
<211> LENGTH: 251
<212> TYPE: PRT
<213> ORGANISM: Vitis vinifera

<400> SEQUENCE: 64

```
Met Gly Arg Ser Pro Cys Cys Glu Lys Ala His Thr Asn Lys Gly Ala
1               5                   10                  15

Trp Thr Lys Glu Glu Asp Asp Arg Leu Ile Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Asn Arg Gly Ile Asp Pro Ser Thr His Arg Pro
        115                 120                 125

Ile Asn Glu Pro Ser Pro Asp Val Thr Thr Ile Ser Phe Ala Ala Ala
    130                 135                 140

Val Lys Glu Glu Lys Ile Asn Ile Ser Ser Thr Gly Gly Phe Gly
145                 150                 155                 160

Cys Lys Thr Glu Lys Asn Pro Val Thr Glu Lys Cys Pro Asp Leu Asn
                165                 170                 175

Leu Glu Leu Arg Ile Ser Pro Pro Tyr Gln Pro Gln Ala Glu Thr Pro
            180                 185                 190

Leu Lys Thr Gly Gly Arg Ser Ser Thr Thr Leu Cys Phe Ala Cys
        195                 200                 205

Ser Leu Gly Ile Pro Asn Ser Glu Glu Cys Ser Cys Ser Ile Gly Thr
    210                 215                 220

Ser Ser Gly Ser Ser Ser Gly Tyr Asp Phe Leu Gly Leu Thr Ser
225                 230                 235                 240

Gly Val Leu Asp Tyr Arg Gly Leu Glu Met Lys
                245                 250
```

<210> SEQ ID NO 65
<211> LENGTH: 648
<212> TYPE: DNA
<213> ORGANISM: Vitis vinifera

<400> SEQUENCE: 65

```
atggggaggt ctccttgctg tgagaaagct catacaaaca aaggggcatg gaccaaggag    60
```

```
gaagatgatc gcctcatcgc ttatatccgg gcacacggcg agggctgctg gaggtctctc    120
cccaaggccg caggccttct ccgatgtggg aaaagttgcc gcctccgatg gataaactac    180
ctgaggcctg acctcaagcg gggaaacttc accgaggaag aagatgaact catcatcaaa    240
ctgcatagtc tccttggcaa caaatggtct cttatagctg ggagattacc aggaagaaca    300
gataatgaaa taagaatta ctggaacacc cacatacgga gaaagcttct gaaccgaggc    360
atcgatccgt ctactcatcg ccccatcaac gagccctcac cggactgtcc agacctcaac    420
cttgagctca gaatcagccc accataccaa ccccaagctg agacgccatt gaagactggt    480
gggaggagta gcagcactac tctttgcttt gcatgcagtt tgggaatacc aaatagtgag    540
gagtgcagtt gcagtattgg tactagtagt ggaagcagca gctctgggta tgacttctta    600
gggttgacat ctggggtttt ggattacaga ggtttggaga tgaaataa                 648
```

<210> SEQ ID NO 66
<211> LENGTH: 215
<212> TYPE: PRT
<213> ORGANISM: Vitis vinifera

<400> SEQUENCE: 66

```
Met Gly Arg Ser Pro Cys Cys Glu Lys Ala His Thr Asn Lys Gly Ala
1               5                   10                  15

Trp Thr Lys Glu Glu Asp Asp Arg Leu Ile Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Asn Arg Gly Ile Asp Pro Ser Thr His Arg Pro
        115                 120                 125

Ile Asn Glu Pro Ser Pro Asp Cys Pro Asp Leu Asn Leu Glu Leu Arg
    130                 135                 140

Ile Ser Pro Pro Tyr Gln Pro Gln Ala Glu Thr Pro Leu Lys Thr Gly
145                 150                 155                 160

Gly Arg Ser Ser Ser Thr Thr Leu Cys Phe Ala Cys Ser Leu Gly Ile
                165                 170                 175

Pro Asn Ser Glu Glu Cys Ser Cys Ser Ile Gly Thr Ser Ser Gly Ser
            180                 185                 190

Ser Ser Ser Gly Tyr Asp Phe Leu Gly Leu Thr Ser Gly Val Leu Asp
        195                 200                 205

Tyr Arg Gly Leu Glu Met Lys
    210                 215
```

<210> SEQ ID NO 67
<211> LENGTH: 801
<212> TYPE: DNA
<213> ORGANISM: Ricinus communis

<400> SEQUENCE: 67

```
atgggaaggt ctccttgttg tgaaaaagcg catacaaata aggtgcatg gactaaagaa      60
gaagatgatc gccttattgc ttacattaga gctcatggtg aaggctgttg gcgttcactt     120
cctaaagctg ctggtcttct tcgttgtggt aaaagctgta gacttcgttg gatcaactat     180
ttaagacctg accttaaacg tggtaatttt actgaggaag aagatgaact cattatcaaa     240
ctccatagtc ttcttggtaa caatggtct cttattgctg gtagattacc aggaagaaca     300
gataatgaga taagaactta ttggaacaca cataagaa gaaagctttt gaatagagga      360
atagatcctg ctacacatag gccacttaat gagccaactc aagaaactgc aacaacagct     420
acaacaacag caacaacaaa cacaataact ttttctacta ttaaagaaga aaagaaaga      480
attagcacac caactacccc cagtacgttt atatgcaaag aggagcaaaa cccagttcat     540
gaaaggtgtc cagacttgaa tcttgagcta agaattagcc tcccatacca agccaacag      600
cagcacgttg ttgagccatt aaaaactgga ggaagaattc tttgtttgc ttgcaggctg      660
ggtctacaaa atagcaagga ttgtagttgt agtattatgg gttctggtat tggaagcagc     720
agtggcaaca gtaattctgg ctatgatttc ttaggcatga aagtggtgt tttggattat     780
agaagcctgg aaatgaaata a                                               801
```

<210> SEQ ID NO 68
<211> LENGTH: 266
<212> TYPE: PRT
<213> ORGANISM: Ricinus communis
<400> SEQUENCE: 68

```
Met Gly Arg Ser Pro Cys Cys Glu Lys Ala His Thr Asn Lys Gly Ala
1               5                   10                  15

Trp Thr Lys Glu Glu Asp Asp Arg Leu Ile Ala Tyr Ile Arg Ala His
            20                  25                  30

Gly Glu Gly Cys Trp Arg Ser Leu Pro Lys Ala Ala Gly Leu

```
                225                 230                 235                 240

Ser Gly Asn Ser Asn Ser Gly Tyr Asp Phe Leu Gly Met Lys Ser Gly
                245                 250                 255

Val Leu Asp Tyr Arg Ser Leu Glu Met Lys
            260                 265

<210> SEQ ID NO 69
<211> LENGTH: 798
<212> TYPE: DNA
<213> ORGANISM: Humulus lupulus

<400> SEQUENCE: 69
atgggaaggt ctccttgttg tgagaaagct cacacaaaca aaggagcgtg gaccaaagaa    60
gaagatgatc gacttattgc atacataagg gctcacggcg agggttgctg gcgctcacta   120
cctaaagccg ccggtctcct aaggtgtggc aagagttgta ggctgcgttg gattaactac   180
ctcagacctg acctcaaacg tggaaacttt acagaagaag aagacgagct tatcatcaag   240
ctccatagtc tccttggaaa caatggtct ttaatagctg gaagactacc aggaagaaca   300
gacaatgaga taagaactα ctggaacacc cataagaa gaaagcttct gaacagagga   360
attgaccctg caactcaccg gccactcaac gagtcaggtc aagaaacgac aaacacttcc   420
accactacaa ccgccacaac aaccaccacc accaccgcct ccaacacgac caccacaatc   480
tcgtttgctg cttccactgt taagaagaa gagaaaacga caagtgtttt gttaaaccca   540
attcaagaac agtgtcctga cttgaacctt gagctcagaa ttagccctcc ttatccgcac   600
cagcaacgcc agccagacca attgaagagc ggtggtgctt ctctctgctt tgcttgtagt   660
ttgggtttgc agaacagtaa agagtgttgc tgtacaattt caagtatgga tagcaataac   720
ccaagcacca gtgttggtta tgatttcttg ggcttgaaat ctggtgtttt ggattacaga   780
agcttggaaa tgaaatag                                                 798

<210> SEQ ID NO 70
<211> LENGTH: 265
<212> TYPE: PRT
<213> ORGANISM: Humulus lupulus

<400> SEQUENCE: 70

Met Gly Arg Ser Pro Cys Cys Glu Lys Ala His Thr Asn Lys Gly Ala
1               5                   10                  15

Trp Thr Lys Glu Glu Asp Asp Arg Leu Ile Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Asn Arg Gly Ile Asp Pro Ala Thr His Arg Pro
        115                 120                 125

Leu Asn Glu Ser Gly Gln Glu Thr Thr Asn Thr Ser Thr Thr Thr
    130                 135                 140
```

| | | | | | | | | | | | | | | | |
|---|---|---|---|---|---|---|---|---|---|---|---|---|---|---|---|
|Ala|Thr|Thr|Thr|Thr|Thr|Thr|Ala|Ser|Asn|Thr|Thr|Thr|Thr|Ile| |
|145| | | |150| | | |155| | | |160| | | |

Ser Phe Ala Ala Ser Thr Val Lys Glu Glu Lys Thr Thr Ser Val
            165                 170                 175

Leu Leu Asn Pro Ile Gln Glu Gln Cys Pro Asp Leu Asn Leu Glu Leu
            180                 185                 190

Arg Ile Ser Pro Pro Tyr Pro His Gln Gln Arg Gln Pro Asp Gln Leu
            195                 200                 205

Lys Ser Gly Gly Ala Ser Leu Cys Phe Ala Cys Ser Leu Gly Leu Gln
            210                 215                 220

Asn Ser Lys Glu Cys Cys Cys Thr Ile Ser Ser Met Asp Ser Asn Asn
225                 230                 235                 240

Pro Ser Thr Ser Val Gly Tyr Asp Phe Leu Gly Leu Lys Ser Gly Val
            245                 250                 255

Leu Asp Tyr Arg Ser Leu Glu Met Lys
            260                 265

<210> SEQ ID NO 71
<211> LENGTH: 708
<212> TYPE: DNA
<213> ORGANISM: Glycine max

<400> SEQUENCE: 71
atgggaaggt cccccttgctg tgagaaagca cacacaaaca aaggtgcatg gaccaaagaa      60
gaagatcatc gcctcatttc ttacattaga gctcacggtg aaggctgctg cgctctctc      120
cccaaagccg ccggccttct ccgttgcggc aagagctgtc gtctccgctg atcaactat      180
ctccgccctg acctcaagcg cggcaatttc tccctcgaag aagaccaact catcatcaaa      240
ctccacagcc tccttggcaa caagtggtct ctaattgctg gtagattgcc cggtagaact      300
gacaatgaga tcaagaatta ctggaatact cacatacgca ggaagcttct gagcagaggt      360
attgaccctg ccactcacag gcctctcaac gattcttctc atcaagaacc tgctgctgtc      420
tctgccccct ctaaacatca agagtccttt caccatgaac gctgccctga cttgaacctt      480
gagctaacca ttagtcctcc ccatcatcct caacctgatc atccgcactt gaagacccct      540
gtgacaaaact caaacctttg ctttccctgc agtctgggtt tgcataatag caaagattgt      600
agctgtgccc tccacactag tactgccaac gctactgcta ctggctatga tttcttggcc      660
ttgaaaacca ccgtcgtttt ggattacaga accttgcaca tgaaatga                   708

<210> SEQ ID NO 72
<211> LENGTH: 235
<212> TYPE: PRT
<213> ORGANISM: Glycine max

<400> SEQUENCE: 72

Met Gly Arg Ser Pro Cys Cys Glu Lys Ala His Thr Asn Lys Gly Ala
1               5                   10                  15

Trp Thr Lys Glu Glu Asp His Arg Leu Ile Ser Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Ser Leu Glu Glu Asp Gln Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Ser Arg Gly Ile Asp Pro Ala Thr His Arg Pro
        115                 120                 125

Leu Asn Asp Ser Ser His Gln Glu Pro Ala Ala Val Ser Ala Pro Pro
    130                 135                 140

Lys His Gln Glu Ser Phe His His Glu Arg Cys Pro Asp Leu Asn Leu
145                 150                 155                 160

Glu Leu Thr Ile Ser Pro Pro His His Pro Gln Pro Asp His Pro His
                165                 170                 175

Leu Lys Thr Leu Val Thr Asn Ser Asn Leu Cys Phe Pro Cys Ser Leu
            180                 185                 190

Gly Leu His Asn Ser Lys Asp Cys Ser Cys Ala Leu His Thr Ser Thr
        195                 200                 205

Ala Asn Ala Thr Ala Thr Gly Tyr Asp Phe Leu Ala Leu Lys Thr Thr
    210                 215                 220

Val Val Leu Asp Tyr Arg Thr Leu His Met Lys
225                 230                 235

<210> SEQ ID NO 73
<211> LENGTH: 744
<212> TYPE: DNA
<213> ORGANISM: Glycine max

<400> SEQUENCE: 73
atgggaaggt cccottgctg tgagaaagct cacacaaaca aggtgcatg gactaaagaa      60
gaagatgaca gactcatatc ttatattcga gctcacggcg aaggctgctg gcgttcactc    120
cccaaagccg ccggtcttct ccggtgcggc aaaagctgcc gtctccggtg atcaactac    180
ctccgccccg accttaaaag aggtaacttt accgaagaag aagacgagct catcatcaaa    240
ctccacagtc cctcggtaa caagtggtct tgatagctg gaagattgcc ggggagaaca      300
gacaatgaaa taaagaacta ttggaatacg cacataagaa ggaagctttt gaacagagga    360
atcgaccctg caactcatag gccactcaac gaagctgcaa ctgctgcaac tgttacaact    420
aatatatctt ttggcaaaca agaacaacaa gagacaagtt cgagtaacgg aagcgttgtt    480
aaaggttcca tcttggaacg ctgccctgac ttgaaccttg agttaaccat tagtcctcct    540
cgccaacaac aacagactca gaagaatctt tgtttcgttt gcagtttggg tttgcacaac    600
agcaaagatt gcagctgcaa cgtttccaac gctgtcactg tcaacaacac cactcctct     660
tctgctgctg ctgctgctgc ttatgatttc ttgggcatga aaaccagcgg cgtttgggat    720
tgcacccgct tggaaatgaa atga                                           744

<210> SEQ ID NO 74
<211> LENGTH: 247
<212> TYPE: PRT
<213> ORGANISM: Glycine max

<400> SEQUENCE: 74

Met Gly Arg Ser Pro Cys Cys Glu Lys Ala His Thr Asn Lys Gly Ala
1               5                   10                  15

Trp Thr Lys Glu Glu Asp Asp Arg Leu Ile Ser Tyr Ile Arg Ala His
            20                  25                  30

Gly Glu Gly Cys Trp Arg Ser Leu Pro Lys Ala Ala Gly Leu Leu Arg

```
                 35                  40                  45
Cys Gly Lys Ser Cys Arg Leu Arg Trp Ile Asn Tyr Leu Arg Pro Asp
 50                  55                  60

Leu Lys Arg Gly Asn Phe Thr Glu Glu Asp Glu Leu Ile Ile Lys
 65                  70                  75                  80

Leu His Ser Leu Leu Gly Asn Lys Trp Ser Leu Ile Ala Gly Arg Leu
                 85                  90                  95

Pro Gly Arg Thr Asp Asn Glu Ile Lys Asn Tyr Trp Asn Thr His Ile
                100                 105                 110

Arg Arg Lys Leu Leu Asn Arg Gly Ile Asp Pro Ala Thr His Arg Pro
                115                 120                 125

Leu Asn Glu Ala Ala Thr Ala Ala Thr Val Thr Thr Asn Ile Ser Phe
                130                 135                 140

Gly Lys Gln Glu Gln Gln Glu Thr Ser Ser Ser Asn Gly Ser Val Val
145                 150                 155                 160

Lys Gly Ser Ile Leu Glu Arg Cys Pro Asp Leu Asn Leu Glu Leu Thr
                165                 170                 175

Ile Ser Pro Pro Arg Gln Gln Gln Thr Gln Lys Asn Leu Cys Phe
                180                 185                 190

Val Cys Ser Leu Gly Leu His Asn Ser Lys Asp Cys Ser Cys Asn Val
                195                 200                 205

Ser Asn Ala Val Thr Val Asn Asn Thr Thr Pro Ser Ser Ala Ala Ala
                210                 215                 220

Ala Ala Ala Tyr Asp Phe Leu Gly Met Lys Thr Ser Gly Val Trp Asp
225                 230                 235                 240

Cys Thr Arg Leu Glu Met Lys
                245

<210> SEQ ID NO 75
<211> LENGTH: 741
<212> TYPE: DNA
<213> ORGANISM: Glycine max

<400> SEQUENCE: 75
atgggaaggt cccttgctg tgaggaagct cacacaaaca aaggtgcatg gactaaagaa        60
gaagatgaca gactcatatc ttatattcga gctcacggcg aaggctgctg cgttcactc       120 cccaaagccg ccggtcttct ccggtgcggc aaaagctgcc gtctccggtg atcaactac       180 ctccgccccg accttaaaag aggtaacttt accgaagaag aagacgagct catcatcaaa      240
ctccacagtc tcctcggtaa caagtggtct tgatagctg gaagattgcc ggggagaaca       300
gacaatgaaa taagaactta ttggaatacg cacataagaa ggaagctttt gaacagagga      360
atcgaccctg caactcatag gccactcaac gaggctgcaa ctgctgcaac tgttacaact      420
aatatatctt ttggcaaaca agaacaacaa gagacaagtt cgagtaacgg aagcgttgtt      480
aaaggttcca tcttggaacg ctgccctgac ttgaaccttg agttaaccat tagtcctcct      540
cgccaacaac aacagactca gaagaatctt tgtttcgttt gcagtttggg tttgcacaac      600
agcaaagatt gcagctgcaa cgtttccaac gctgtcactg tcaacaacac cactcctttt      660
tctgctgctg ctgctgctta tgatttcttg ggtatgaaaa ccagcggtgt ttgggattgc      720
acccgcttgg aaatgaaatg a                                               741

<210> SEQ ID NO 76
<211> LENGTH: 246
<212> TYPE: PRT
```

<213> ORGANISM: Glycine max

<400> SEQUENCE: 76

```
Met Gly Arg Ser Pro Cys Cys Glu Glu Ala His Thr Asn Lys Gly Ala
1               5                   10                  15
Trp Thr Lys Glu Glu Asp Asp Arg Leu Ile Ser Tyr Ile Arg Ala His
            20                  25                  30
Gly Glu Gly Cys Trp Arg Ser Leu Pro Lys Ala Ala Gly Leu Leu Arg
        35                  40                  45
Cys Gly Lys Ser Cys Arg Leu Arg Trp Ile Asn Tyr Leu Arg Pro Asp
    50                  55                  60
Leu Lys Arg Gly Asn Phe Thr Glu Glu Asp Glu Leu Ile Ile Lys
65                  70                  75                  80
Leu His Ser Leu Leu Gly Asn Lys Trp Ser Leu Ile Ala Gly Arg Leu
                85                  90                  95
Pro Gly Arg Thr Asp Asn Glu Ile Lys Asn Tyr Trp Asn Thr His Ile
            100                 105                 110
Arg Arg Lys Leu Leu Asn Arg Gly Ile Asp Pro Ala Thr His Arg Pro
        115                 120                 125
Leu Asn Glu Ala Ala Thr Ala Ala Thr Val Thr Thr Asn Ile Ser Phe
    130                 135                 140
Gly Lys Gln Glu Gln Gln Glu Thr Ser Ser Asn Gly Ser Val Val
145                 150                 155                 160
Lys Gly Ser Ile Leu Glu Arg Cys Pro Asp Leu Asn Leu Glu Leu Thr
                165                 170                 175
Ile Ser Pro Pro Arg Gln Gln Gln Thr Gln Lys Asn Leu Cys Phe
            180                 185                 190
Val Cys Ser Leu Gly Leu His Asn Ser Lys Asp Cys Ser Cys Asn Val
        195                 200                 205
Ser Asn Ala Val Thr Val Asn Asn Thr Thr Pro Phe Ser Ala Ala Ala
    210                 215                 220
Ala Ala Tyr Asp Phe Leu Gly Met Lys Thr Ser Gly Val Trp Asp Cys
225                 230                 235                 240
Thr Arg Leu Glu Met Lys
                245
```

<210> SEQ ID NO 77
<211> LENGTH: 762
<212> TYPE: DNA
<213> ORGANISM: Glycine max

<400> SEQUENCE: 77

```
atgggaaggt cccttgctg tgagaaagct cacacaaaca aaggtgcatg gactaaagaa      60
gaagatgaca gactcatatc ttatattcga gctcacggag aaggctgctg gcgttcactc    120
cccaaagccg ccggccttct ccggtgcggc aagagctgcc gtctccggtg atcaactac    180
ctccgccccg acctcaaaag aggtaacttt accgaagaag aagatgaact catcatcaaa    240
ctccacagtc tcctcggtaa caagtggtct ttgatagctg gaagattgcc ggggagaaca    300
gacaatgaaa taagaattta ttggaacacg cacataagaa ggaagctttt gaacagagga    360
atcgaccctg ctactcatag gccactcaac gaggctgctt ctgctgcaac tgttacaact    420
gccaccacta atatatcttt tgggaaacaa caagaacaag agacaagttc tagtaacgga    480
agcgttgtta aaggttccat cttgaacgc tgccctgact tgaaccttga gttaaccatt    540
agtcctcctc gccaacaaca acctcagaag aatctttgtt ttgtttgcag tttgggtttg    600
```

| | | |
|---|---|---|
| aacaacagca aggattgtag ctgcaacgtt gccaacactg ttactgttac tgtcagcaac | 660 | |
| actactcctt cttctgctgc tgctgctgct gctgctgctt atgatttctt gggcatgaaa | 720 | |
| accaacggtg tttgggattg cacccgcttg gaaatgaaat ga | 762 | |

<210> SEQ ID NO 78
<211> LENGTH: 253
<212> TYPE: PRT
<213> ORGANISM: Glycine max

<400> SEQUENCE: 78

```
Met Gly Arg Ser Pro Cys Cys Glu Lys Ala His Thr Asn Lys Gly Ala
1               5                   10                  15
Trp Thr Lys Glu Glu Asp Asp Arg Leu Ile Ser Tyr Ile Arg Ala His
            20                  25                  30
Gly Glu Gly Cys Trp Arg Ser Leu Pro Lys Ala Ala Gly Leu Leu Arg
        35                  40                  45
Cys Gly Lys Ser Cys Arg Leu Arg Trp Ile Asn Tyr Leu Arg Pro Asp
    50                  55                  60
Leu Lys Arg Gly Asn Phe Thr Glu Glu Asp Glu Leu Ile Ile Lys
65                  70                  75                  80
Leu His Ser Leu Leu Gly Asn Lys Trp Ser Leu Ile Ala Gly Arg Leu
                85                  90                  95
Pro Gly Arg Thr Asp Asn Glu Ile Lys Asn Tyr Trp Asn Thr His Ile
            100                 105                 110
Arg Arg Lys Leu Leu Asn Arg Gly Ile Asp Pro Ala Thr His Arg Pro
        115                 120                 125
Leu Asn Glu Ala Ala Ser Ala Ala Thr Val Thr Thr Ala Thr Thr Asn
    130                 135                 140
Ile Ser Phe Gly Lys Gln Gln Glu Gln Glu Thr Ser Ser Ser Asn Gly
145                 150                 155                 160
Ser Val Val Lys Gly Ser Ile Leu Glu Arg Cys Pro Asp Leu Asn Leu
                165                 170                 175
Glu Leu Thr Ile Ser Pro Pro Arg Gln Gln Pro Gln Lys Asn Leu
            180                 185                 190
Cys Phe Val Cys Ser Leu Gly Leu Asn Asn Ser Lys Asp Cys Ser Cys
        195                 200                 205
Asn Val Ala Asn Thr Val Thr Val Thr Val Ser Asn Thr Thr Pro Ser
    210                 215                 220
Ser Ala Ala Ala Ala Ala Ala Ala Tyr Asp Phe Leu Gly Met Lys
225                 230                 235                 240
Thr Asn Gly Val Trp Asp Cys Thr Arg Leu Glu Met Lys
                245                 250
```

<210> SEQ ID NO 79
<211> LENGTH: 633
<212> TYPE: DNA
<213> ORGANISM: Glycine max

<400> SEQUENCE: 79

| | | |
|---|---|---|
| atgggaaggt cccttgctg tgagaaagca cacacaaaca aggtgcatg gaccaaagaa | 60 | |
| gaagatcatc gcctcatttc ttacattaga gctcacggtg aaggctgctg gcgctctctc | 120 | |
| cccaaagccg ccggccttct ccgttgcggc aagagctgtc gtctccgctg gatcaactat | 180 | |
| ctccgccctg acctcaagcg cggcaatttc tccctcgaag aagaccaact catcatcaaa | 240 | |

```
ctccatagcc tccttggcaa caagtggtct ctaattgctg aagattgcc gggtagaacg    300 gacaatgaga taaagaatta ctggaatact cacataagaa ggaagcttct gagcagagga    360
attgaccctg ccactcacag gcctctcaac gatgacaagg tattggaacg ctgccctgac    420
ttgaaccttg agctaaccat tagtcctccc cgtcaacctc aatctgatca gcatcacttg    480
aagcccgttg ggagaaactc aaacctttgc tttgcctgca gtttgggttt gcaaaatagc    540
aaagatcatt gtagctgtgc gctcaacact gccaacgctg cttctggcca tgatttcttg    600
gccttgaaaa ccagcgtttt ggaaatgaaa tga                                633
```

<210> SEQ ID NO 80
<211> LENGTH: 210
<212> TYPE: PRT
<213> ORGANISM: Glycine max

<400> SEQUENCE: 80

```
Met Gly Arg Ser Pro Cys Cys Glu Lys Ala His Thr Asn Lys Gly Ala
1               5                   10                  15

Trp Thr Lys Glu Glu Asp His Arg Leu Ile Ser Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Ser Leu Glu Glu Asp Gln Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Ser Arg Gly Ile Asp Pro Ala Thr His Arg Pro
        115                 120                 125

Leu Asn Asp Asp Lys Val Leu Glu Arg Cys Pro Asp Leu Asn Leu Glu
    130                 135                 140

Leu Thr Ile Ser Pro Pro Arg Gln Pro Gln Ser Asp Gln His His Leu
145                 150                 155                 160

Lys Pro Val Gly Arg Asn Ser Asn Leu Cys Phe Ala Cys Ser Leu Gly
                165                 170                 175

Leu Gln Asn Ser Lys Asp His Cys Ser Cys Ala Leu Asn Thr Ala Asn
            180                 185                 190

Ala Ala Ser Gly His Asp Phe Leu Ala Leu Lys Thr Ser Val Leu Glu
        195                 200                 205

Met Lys
    210
```

<210> SEQ ID NO 81
<211> LENGTH: 633
<212> TYPE: DNA
<213> ORGANISM: Glycine max

<400> SEQUENCE: 81

```
atgggaaggt cccttgctg tgagaaagca cacacaaaca aggtgcatg gaccaaagaa     60 gaagatcatc gcctcatttc ttacattaga gctcacggtg aaggctgctg gcgctctctc    120
cccaaagccg ccggccttct ccgttgcggc aagagctgtc gtctccgctg atcaactat    180 ctccgccctg acctcaagcg cggcaatttc tccctcgaag aagaccaact catcatcaaa    240
```

```
ctccatcgcc tccttggcaa caagtggtct ctaattgctg aagattgcc gggtagaacg      300 gacaatgaga taaagaatta ctggaatact cacataagaa ggaagcttct gagcagagga      360
attgaccctg ccactcacag gcctctcaac gatgacaagg tattggaacg ctgccctgac      420
ttgaaccttg agctaaccat tagtcctccc cgtcaacctc aatctgatca gcatcacttg      480
aagcccgttg ggagaaactc aaacctttgc tttgcctgca gtttgggttt gcaaaatagc      540
aaaggtcatt gtagctgtgc gctcaacact gccaacgctg cttctggcca tgatttcttg      600
gccttgaaaa ccagcgtttt ggaaatgaaa tga                                   633
```

```
<210> SEQ ID NO 82
<211> LENGTH: 210
<212> TYPE: PRT
<213> ORGANISM: Glycine max

<400> SEQUENCE: 82

Met Gly Arg Ser Pro Cys Cys Glu Lys Ala His Thr Asn Lys Gly Ala
1               5                   10                  15

Trp Thr Lys Glu Glu Asp His Arg Leu Ile Ser Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Ser Leu Glu Glu Asp Gln Leu Ile Ile Lys
65                  70                  75                  80

Leu His Arg Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Ser Arg Gly Ile Asp Pro Ala Thr His Arg Pro
        115                 120                 125

Leu Asn Asp Asp Lys Val Leu Glu Arg Cys Pro Asp Leu Asn Leu Glu
    130                 135                 140

Leu Thr Ile Ser Pro Pro Arg Gln Pro Gln Ser Asp Gln His His Leu
145                 150                 155                 160

Lys Pro Val Gly Arg Asn Ser Asn Leu Cys Phe Ala Cys Ser Leu Gly
                165                 170                 175

Leu Gln Asn Ser Lys Gly His Cys Ser Cys Ala Leu Asn Thr Ala Asn
            180                 185                 190

Ala Ala Ser Gly His Asp Phe Leu Ala Leu Lys Thr Ser Val Leu Glu
        195                 200                 205

Met Lys
    210
```

```
<210> SEQ ID NO 83
<211> LENGTH: 849
<212> TYPE: DNA
<213> ORGANISM: Arabidopsis lyrata

<400> SEQUENCE: 83
atgggaaggt caccgtgttg tgagaaagct cacacaaaca aggagcatg gacgaaagaa       60 gaggacgaga ggctcatagc ttacattaaa gctcatggag aaggctgctg gagatctctc     120
cccaaagccg ccggacttct tcggtgtgga aaaagctgcc gtctccggtg gatcaactat     180
```

```
ctccggcctg accttaagcg tggaaacttc accgaggaag aagacgagct catcatcaag    240
ctccatagcc ttcttggcaa caaatggtcg cttattgccg ggagattgcc gggaagaaca    300
gataacgaga ttaagaacta ctggaacaca catatacgaa gaaagcttat aaacagaggg    360
attgatccaa cgactcatag accaatccaa gaatcatcag cttctcaaga ttctaaacct    420
acacaactag aaccagttac gagtaacacc attaatatct ccttcacttc tgctccaaag    480
gtcgaaacgt tccatgagag tataagtttt ccagagaaaa tctcaatgct tacgttcaaa    540
gaggaaaaag acgagtgccc agttgcagaa aagttcccag atttgaatct tgagctcaga    600
atcagtcttc ctgatgatgt tgatcgtcgt cgaggcttgg tgggacacgg aaagtcaaca    660
acgcctcgtt gtttcaagtg cagcttaggg atgataaacg gcatggagtg cagatgcgga    720
agaatgagat gcgatgtagt tggaggtagc agcaagggga gtgacttgag caagggattt    780
gattttttag ggttggcaaa gaaagagacc acttctcttt tgggttttag aagcttggag    840
atgaaataa                                                            849

<210> SEQ ID NO 84
<211> LENGTH: 282
<212> TYPE: PRT
<213> ORGANISM: Arabidopsis lyrata

<400> SEQUENCE: 84

Met Gly Arg Ser Pro Cys Cys Glu Lys Ala His Thr Asn Lys Gly Ala
1               5                   10                  15
Trp Thr Lys Glu Glu Asp Glu Arg Leu Ile Ala Tyr Ile Lys Ala His
                20                  25                  30
Gly Glu Gly Cys Trp Arg Ser Leu Pro Lys Ala Ala Gly Leu Leu Arg
            35                  40                  45
Cys Gly Lys Ser Cys Arg Leu Arg Trp Ile Asn Tyr Leu Arg Pro Asp
        50                  55                  60
Leu Lys Arg Gly Asn Phe Thr Glu Glu Asp Glu Leu Ile Ile Lys
65                  70                  75                  80
Leu His Ser Leu Leu Gly Asn Lys Trp Ser Leu Ile Ala Gly Arg Leu
                85                  90                  95
Pro Gly Arg Thr Asp Asn Glu Ile Lys Asn Tyr Trp Asn Thr His Ile
            100                 105                 110
Arg Arg Lys Leu Ile Asn Arg Gly Ile Asp Pro Thr Thr His Arg Pro
        115                 120                 125
Ile Gln Glu Ser Ser Ala Ser Gln Asp Ser Lys Pro Thr Gln Leu Glu
    130                 135                 140
Pro Val Thr Ser Asn Thr Ile Asn Ile Ser Phe Thr Ser Ala Pro Lys
145                 150                 155                 160
Val Glu Thr Phe His Glu Ser Ile Ser Phe Pro Glu Lys Ile Ser Met
                165                 170                 175
Leu Thr Phe Lys Glu Glu Lys Asp Glu Cys Pro Val Ala Glu Lys Phe
            180                 185                 190
Pro Asp Leu Asn Leu Glu Leu Arg Ile Ser Leu Pro Asp Asp Val Asp
        195                 200                 205
Arg Arg Arg Gly Leu Val Gly His Gly Lys Ser Thr Thr Pro Arg Cys
    210                 215                 220
Phe Lys Cys Ser Leu Gly Met Ile Asn Gly Met Glu Cys Arg Cys Gly
225                 230                 235                 240
Arg Met Arg Cys Asp Val Val Gly Gly Ser Ser Lys Gly Ser Asp Leu
                245                 250                 255
```

```
Ser Lys Gly Phe Asp Phe Leu Gly Leu Ala Lys Lys Glu Thr Thr Ser
            260                 265                 270

Leu Leu Gly Phe Arg Ser Leu Glu Met Lys
        275                 280
```

<210> SEQ ID NO 85
<211> LENGTH: 848
<212> TYPE: DNA
<213> ORGANISM: Arabidopsis thaliana

<400> SEQUENCE: 85

| | | | | | |
|---|---|---|---|---|---|
| atgggaaggt | caccgtgctg | tgagaaagct | cacacaaaca | aaggagcatg gacgaaagaa | 60 |
| gaggacgaga | ggctcgtcgc | ctacattaaa | gctcatggag | aaggctgctg gagatctctc | 120 |
| cccaaagccg | ccggacttct | tcgctgtggc | aagagctgcc | gtctccggtg gatcaactat | 180 |
| ctccggcctg | accttaagcg | tggaaacttc | accgaggaag | aagacgaact catcatcaag | 240 |
| ctccatagcc | ttcttggcaa | caaatgtcgc | ttattgccgg | agattaccg ggaagaacag | 300 |
| ataacgagat | aaagaactat | tggaacacgc | atatacgaag | aaagcttata aacagaggga | 360 |
| ttgatccaac | gagtcataga | ccaatccaag | aatcatcagc | ttctcaagat tctaaaccta | 420 |
| cacaactaga | accagttacg | agtaatacca | ttaatatctc | attcacttct gctccaaagg | 480 |
| tcgaaacgtt | ccatgaaagt | ataagctttc | cgggaaaatc | agagaaaatc tcaatgctta | 540 |
| cgttcaaaga | agaaaaagat | gagtgcccag | ttcaagaaaa | gttcccagat ttgaatcttg | 600 |
| agctcagaat | cagtcttcct | gatgatgttg | atcgtcttca | agggcatgga agtcaacaa | 660 |
| cgccacgttg | tttcaagtgc | agcttaggga | tgataaacgg | catggagtgc agatgcggaa | 720 |
| gaatgagatg | cgatgtagtc | ggaggtagca | gcaaggggag | tgacatgagc aatggatttg | 780 |
| attttttagg | gttggcaaag | aaagagacca | cttctctttt | gggctttcga agcttggaga | 840 |
| tgaaataa | | | | | 848 |

<210> SEQ ID NO 86
<211> LENGTH: 282
<212> TYPE: PRT
<213> ORGANISM: Arabidopsis thaliana

<400> SEQUENCE: 86

```
Met Gly Arg Ser Pro Cys Cys Glu Lys Ala His Thr Asn Lys Gly Ala
1               5                   10                  15

Trp Thr Lys Glu Glu Asp Glu Arg Leu Val Ala Tyr Ile Lys Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Ile Asn Arg Gly Ile Asp Pro Thr Ser His Arg Pro
        115                 120                 125

Ile Gln Glu Ser Ser Ala Ser Gln Asp Ser Lys Pro Thr Gln Leu Glu
    130                 135                 140
```

Pro Val Thr Ser Asn Thr Ile Asn Ile Ser Phe Thr Ser Ala Pro Lys
145                 150                 155                 160

Val Glu Thr Phe His Glu Ser Ile Ser Phe Pro Gly Lys Ser Glu Lys
                165                 170                 175

Ile Ser Met Leu Thr Phe Lys Glu Glu Lys Asp Glu Cys Pro Val Gln
            180                 185                 190

Glu Lys Phe Pro Asp Leu Asn Leu Glu Leu Arg Ile Ser Leu Pro Asp
        195                 200                 205

Asp Val Asp Arg Leu Gln Gly His Gly Lys Ser Thr Thr Pro Arg Cys
    210                 215                 220

Phe Lys Cys Ser Leu Gly Met Ile Asn Gly Met Glu Cys Arg Cys Gly
225                 230                 235                 240

Arg Met Arg Cys Asp Val Val Gly Gly Ser Ser Lys Gly Ser Asp Met
                245                 250                 255

Ser Asn Gly Phe Asp Phe Leu Gly Leu Ala Lys Lys Glu Thr Thr Ser
            260                 265                 270

Leu Leu Gly Phe Arg Ser Leu Glu Met Lys
        275                 280

<210> SEQ ID NO 87
<211> LENGTH: 849
<212> TYPE: DNA
<213> ORGANISM: Arabidopsis thaliana

<400> SEQUENCE: 87
atgggaaggt caccgtgctg tgagaaagct cacacaaaca aaggagcatg gacgaaagaa      60
gaggacgaga ggctcgtcgc ctacattaaa gctcatggag aaggctgctg agatctctc     120 cccaaagccg ccggacttct tcgctgtggc aagagctgcc gtctccggtg atcaactat     180 ctccggcctg accttaagcg tggaaacttc accgaggaag aagacgaact catcatcaag     240
ctccatagcc ttcttggcaa caaatggtcg cttattgccg ggagattacc gggaagaaca     300
gataacgaga taagaactta ttggaacacg catatacgaa gaaagcttat aaacagaggg     360
attgatccaa cgagtcatag accaatccaa gaatcatcag cttctcaaga ttctaaacct     420
atacaactag aaccagttac gagtaatacc attaatatct cattcacttc tgctccaaag     480
gtcgaaacgt tccatgaaag tataagcttt ccgggaaaat cagagaaaat ctcaatgctt     540
acgttcaaag aagaaaaaga tgagtgccca gttcaagaaa agttcccaga tttgaatctt     600
gagctcagaa tcagtcttcc tgatgatgtt gatcgtcttc aagggcatgg aaagtcaaca     660
acgccacgtt gtttcaagtg cagcttaggg atgataaacg gcatggagtg cagatgcgga     720
agaatgagat gcgatgtagt cggaggtagc agcaagggga gtgacatgag caatggattt     780 gatttttag ggttggcaaa gaaagagacc acttctcttt gggctttcg aagcttggag     840 atgaaataa                                                              849

<210> SEQ ID NO 88
<211> LENGTH: 282
<212> TYPE: PRT
<213> ORGANISM: Arabidopsis thaliana

<400> SEQUENCE: 88

Met Gly Arg Ser Pro Cys Cys Glu Lys Ala His Thr Asn Lys Gly Ala
1               5                   10                  15

Trp Thr Lys Glu Glu Asp Glu Arg Leu Val Ala Tyr Ile Lys Ala His
            20                  25                  30

```
Gly Glu Gly Cys Trp Arg Ser Leu Pro Lys Ala Ala Gly Leu Leu Arg
         35                  40                  45

Cys Gly Lys Ser Cys Arg Leu Arg Trp Ile Asn Tyr Leu Arg Pro Asp
 50                  55                  60

Leu Lys Arg Gly Asn Phe Thr Glu Glu Asp Glu Leu Ile Ile Lys
 65                  70                  75                  80

Leu His Ser Leu Leu Gly Asn Lys Trp Ser Leu Ile Ala Gly Arg Leu
                 85                  90                  95

Pro Gly Arg Thr Asp Asn Glu Ile Lys Asn Tyr Trp Asn Thr His Ile
                100                 105                 110

Arg Arg Lys Leu Ile Asn Arg Gly Ile Asp Pro Thr Ser His Arg Pro
             115                 120                 125

Ile Gln Glu Ser Ser Ala Ser Gln Asp Ser Lys Pro Ile Gln Leu Glu
         130                 135                 140

Pro Val Thr Ser Asn Thr Ile Asn Ile Ser Phe Thr Ser Ala Pro Lys
145                 150                 155                 160

Val Glu Thr Phe His Glu Ser Ile Ser Phe Pro Gly Lys Ser Glu Lys
                165                 170                 175

Ile Ser Met Leu Thr Phe Lys Glu Lys Asp Glu Cys Pro Val Gln
             180                 185                 190

Glu Lys Phe Pro Asp Leu Asn Leu Glu Leu Arg Ile Ser Leu Pro Asp
         195                 200                 205

Asp Val Asp Arg Leu Gln Gly His Gly Lys Ser Thr Thr Pro Arg Cys
210                 215                 220

Phe Lys Cys Ser Leu Gly Met Ile Asn Gly Met Glu Cys Arg Cys Gly
225                 230                 235                 240

Arg Met Arg Cys Asp Val Val Gly Gly Ser Ser Lys Gly Ser Asp Met
                245                 250                 255

Ser Asn Gly Phe Asp Phe Leu Gly Leu Ala Lys Lys Glu Thr Thr Ser
             260                 265                 270

Leu Leu Gly Phe Arg Ser Leu Glu Met Lys
         275                 280
```

<210> SEQ ID NO 89
<211> LENGTH: 810
<212> TYPE: DNA
<213> ORGANISM: Arabidopsis lyrata

<400> SEQUENCE: 89

```
atgggaagat ctccttgttg cgagaaagaa cacatgaaca aggtgcttg gactaaagaa      60
gaagacgaga gacttgtctc ttatatcaag tctcacggtg aaggttgttg gcgatctctt    120
cctagagccg ctggtctcct ccgttgcggt aaaagctgtc gtctccggtg gattaactat    180
ctccgacctg atctcaaaag aggaaacttt acacatgatg aagatgaact tatcgtcaag    240
cttcatagcc tccttggcaa caagtggtct ttaattgcgg cgagattacc tggaagaaca    300
gataacgaga tcaagaatta ctggaataca catataaaga ggaagctttt gagcaaaggg    360
attgatccgg ctacgcatag agcgatcaac gaggcgaaag tttctgattt gaagaaaaaa    420
gaggaccaaa ttgtaaaaga tgtttctttt gggtctaagt ttgagaaaat agaaaagtct    480
ggggacaaga agcaaaataa gcatattaga aatgggttag tgtgcaaaga agagagagtt    540
gttgttgaag aaaatatatg cccagatttg aatcttgagc ttaggatcag tccaccatgg    600
caaaaccaga gagaaatatc tccttgcact gcgtcccgtt tttacatgga aaacggcatg    660
```

```
gagtgtagta gtgaaagtgt gaaatgtcaa acagaggata gtagtagcat tagctattct    720
tctattgata ttagtagtag caacgttggt tatgacttct tgggtttgaa gacaagaatt    780
ttggattttc gaagcttgga aatgaaataa                                      810
```

<210> SEQ ID NO 90
<211> LENGTH: 269
<212> TYPE: PRT
<213> ORGANISM: Arabidopsis lyrata

<400> SEQUENCE: 90

```
Met Gly Arg Ser Pro Cys Cys Glu Lys Glu His Met Asn Lys Gly Ala
1               5                   10                  15

Trp Thr Lys Glu Glu Asp Glu Arg Leu Val Ser Tyr Ile Lys Ser His
            20                  25                  30

Gly Glu Gly Cys Trp Arg Ser Leu Pro Arg Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr His Asp Glu Asp Glu Leu Ile Val Lys
65                  70                  75                  80

Leu His Ser Leu Leu Gly Asn Lys Trp Ser Leu Ile Ala Ala Arg Leu
                85                  90                  95

Pro Gly Arg Thr Asp Asn Glu Ile Lys Asn Tyr Trp Asn Thr His Ile
            100                 105                 110

Lys Arg Lys Leu Leu Ser Lys Gly Ile Asp Pro Ala Thr His Arg Ala
        115                 120                 125

Ile Asn Glu Ala Lys Val Ser Asp Leu Lys Lys Lys Glu Asp Gln Ile
    130                 135                 140

Val Lys Asp Val Ser Phe Gly Ser Lys Phe Glu Lys Ile Glu Lys Ser
145                 150                 155                 160

Gly Asp Lys Lys Gln Asn Lys His Ile Arg Asn Gly Leu Val Cys Lys
                165                 170                 175

Glu Glu Arg Val Val Val Glu Glu Asn Ile Cys Pro Asp Leu Asn Leu
            180                 185                 190

Glu Leu Arg Ile Ser Pro Pro Trp Gln Asn Gln Arg Glu Ile Ser Pro
        195                 200                 205

Cys Thr Ala Ser Arg Phe Tyr Met Glu Asn Gly Met Glu Cys Ser Ser
    210                 215                 220

Glu Ser Val Lys Cys Gln Thr Glu Asp Ser Ser Ile Ser Tyr Ser
225                 230                 235                 240

Ser Ile Asp Ile Ser Ser Ser Asn Val Gly Tyr Asp Phe Leu Gly Leu
                245                 250                 255

Lys Thr Arg Ile Leu Asp Phe Arg Ser Leu Glu Met Lys
            260                 265
```

<210> SEQ ID NO 91
<211> LENGTH: 825
<212> TYPE: DNA
<213> ORGANISM: Arabidopsis thaliana

<400> SEQUENCE: 91

```
atgggaaggt ctccttgctg tgagaaagac cacacaaaca aaggagcttg gactaaggaa    60
gaagacgata agctcatctc ttacatcaaa gctcacggtg aaggttgttg gcgttctctt   120
cctagatccg ccggtcttca acgttgcgga aaaagctgtc gtctccgatg gattaactat   180
```

-continued

```
ctccgacctg atctcaagag gggtaacttc accctcgaag aagatgatct catcatcaaa    240
ctacatagcc ttctcggtaa caagtggtct cttattgcga cgagattacc aggaagaaca    300
gataacgaga ttaagaatta ctggaacaca catgttaaga ggaagctatt aagaaaaggg    360
attgatccgg cgactcatcg acctatcaac gagaccaaaa cttctcaaga ttcgtctgat    420
tctagtaaaa cagaggaccc tcttgtcaag attctctctt ttggtcctca gctggagaaa    480
atagcaaatt tcggggacga gagaattcaa aagagagttg agtactcagt tgttgaagaa    540
agatgtctgg acttgaatct tgagcttagg atcagtccac catggcaaga caagttccat    600
gatgagagga acctaaggtt tgggagagtg aagcataggt gcagtgcgtg ccgttttgga    660
ttcgggaacg gcaaggagtg tagctgtaat aatgtgaaat gtcaaacaga ggacagtagt    720
agcagcagtt attcttcaac cgacattagt agtagcattg gttatgactt cttgggtcta    780
aacaacacta gggttttgga ttttagcact ttggaaatga aatga                    825
```

<210> SEQ ID NO 92
<211> LENGTH: 274
<212> TYPE: PRT
<213> ORGANISM: Arabidopsis thaliana

<400> SEQUENCE: 92

```
Met Gly Arg Ser Pro Cys Cys Glu Lys Asp His Thr Asn Lys Gly Ala
1               5                  10                  15

Trp Thr Lys Glu Glu Asp Asp Lys Leu Ile Ser Tyr Ile Lys Ala His
            20                  25                  30

Gly Glu Gly Cys Trp Arg Ser Leu Pro Arg Ser Ala Gly Leu Gln Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Leu Glu Glu Asp Leu Ile Ile Lys
65                  70                  75                  80

Leu His Ser Leu Leu Gly Asn Lys Trp Ser Leu Ile Ala Thr Arg Leu
                85                  90                  95

Pro Gly Arg Thr Asp Asn Glu Ile Lys Asn Tyr Trp Asn Thr His Val
            100                 105                 110

Lys Arg Lys Leu Leu Arg Lys Gly Ile Asp Pro Ala Thr His Arg Pro
        115                 120                 125

Ile Asn Glu Thr Lys Thr Ser Gln Asp Ser Ser Asp Ser Ser Lys Thr
    130                 135                 140

Glu Asp Pro Leu Val Lys Ile Leu Ser Phe Gly Pro Gln Leu Glu Lys
145                 150                 155                 160

Ile Ala Asn Phe Gly Asp Glu Arg Ile Gln Lys Arg Val Glu Tyr Ser
                165                 170                 175

Val Val Glu Glu Arg Cys Leu Asp Leu Asn Leu Glu Leu Arg Ile Ser
            180                 185                 190

Pro Pro Trp Gln Asp Lys Phe His Asp Glu Arg Asn Leu Arg Phe Gly
        195                 200                 205

Arg Val Lys His Arg Cys Ser Ala Cys Arg Phe Gly Phe Gly Asn Gly
    210                 215                 220

Lys Glu Cys Ser Cys Asn Asn Val Lys Cys Gln Thr Glu Asp Ser Ser
225                 230                 235                 240

Ser Ser Ser Tyr Ser Ser Thr Asp Ile Ser Ser Ile Gly Tyr Asp
                245                 250                 255

Phe Leu Gly Leu Asn Asn Thr Arg Val Leu Asp Phe Ser Thr Leu Glu
```

Met Lys

<210> SEQ ID NO 93
<211> LENGTH: 825
<212> TYPE: DNA
<213> ORGANISM: Arabidopsis thaliana

<400> SEQUENCE: 93

```
atgggaaggt ctccttgctg tgagaaagac cacacaaaca aaggagcttg gactaaggaa      60
gaagacgata agctcatctc ttacatcaaa gctcacggtg aaggttgttg gcgttctctt     120
cctagatccg ccggtcttca acgttgcgga aaaagctgtc gtctccgatg gattaactat     180
ctccgacctg atctcaagag gggtaacttc accctcgaag aagatgatct catcatcaaa     240
ctacatagcc ttctcggtaa caagtggtct cttattgcga cgagattacc aggaagaaca     300
gataacgaga ttaagaatta ctggaacaca catgttaaga ggaagctatt aagaaaaggg     360
attgatccgg cgactcatcg acctatcaac gagaccaaaa cttctcaaga ttcgtctgat     420
tctagtaaaa cagaggaccc tcttgtcaag attctctctt ttggtcctca gctggagaaa     480
atagcaaatt tcggggacga gagaattcaa aagagagttg agtactcagt tgttgaagaa     540
agatgtctgg acttgaatct tgagcttagg atcagtccac catggcaaga caagctccat     600
gatgagagga acctaaggtt tgggagagtg aagtataggt gcagtgcgtg ccgttttgga     660
ttcgggaacg gcaaggagtg tagctgtaat aatgtgaaat gtcaaacaga ggacagtagt     720
agcagcagtt attcttcaac cgacattagt agtagcattg gttatgactt cttgggtcta     780
aacaacacta gggttttgga tttttagcact ttggaaatga aatga                    825
```

<210> SEQ ID NO 94
<211> LENGTH: 274
<212> TYPE: PRT
<213> ORGANISM: Arabidopsis thaliana

<400> SEQUENCE: 94

Met Gly Arg Ser Pro Cys Cys Glu Lys Asp His Thr Asn Lys Gly Ala
1               5                   10                  15

Trp Thr Lys Glu Glu Asp Asp Lys Leu Ile Ser Tyr Ile Lys Ala His
            20                  25                  30

Gly Glu Gly Cys Trp Arg Ser Leu Pro Arg Ser Ala Gly Leu Gln Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Leu Glu Glu Asp Asp Leu Ile Ile Lys
65                  70                  75                  80

Leu His Ser Leu Leu Gly Asn Lys Trp Ser Leu Ile Ala Thr Arg Leu
                85                  90                  95

Pro Gly Arg Thr Asp Asn Glu Ile Lys Asn Tyr Trp Asn Thr His Val
            100                 105                 110

Lys Arg Lys Leu Leu Arg Lys Gly Ile Asp Pro Ala Thr His Arg Pro
        115                 120                 125

Ile Asn Glu Thr Lys Thr Ser Gln Asp Ser Ser Asp Ser Ser Lys Thr
    130                 135                 140

Glu Asp Pro Leu Val Lys Ile Leu Ser Phe Gly Pro Gln Leu Glu Lys
145                 150                 155                 160

Ile Ala Asn Phe Gly Asp Glu Arg Ile Gln Lys Arg Val Glu Tyr Ser

```
            165                 170                 175
Val Val Glu Glu Arg Cys Leu Asp Leu Asn Leu Glu Leu Arg Ile Ser
            180                 185                 190

Pro Pro Trp Gln Asp Lys Leu His Asp Glu Arg Asn Leu Arg Phe Gly
            195                 200                 205

Arg Val Lys Tyr Arg Cys Ser Ala Cys Arg Phe Gly Phe Gly Asn Gly
            210                 215                 220

Lys Glu Cys Ser Cys Asn Asn Val Lys Cys Gln Thr Glu Asp Ser Ser
225                 230                 235                 240

Ser Ser Ser Tyr Ser Ser Thr Asp Ile Ser Ser Ile Gly Tyr Asp
                    245                 250                 255

Phe Leu Gly Leu Asn Asn Thr Arg Val Leu Asp Phe Ser Thr Leu Glu
                    260                 265                 270

Met Lys

<210> SEQ ID NO 95
<211> LENGTH: 810
<212> TYPE: DNA
<213> ORGANISM: Arabidopsis thaliana

<400> SEQUENCE: 95
atgggaagat ctccttgctg cgagaaagaa cacatgaaca aggtgcttg gactaaagaa      60 gaagatgaga gactagtctc ttacatcaag tctcacggtg aaggttgttg gcgatctctt     120
cctagagccg ctggtctcct tcgctgcggt aaaagctgcc gtcttcggtg gattaactat     180
ctccgacctg atctcaaaag aggaaacttt acacatgatg aagatgaact atcatcaag     240 cttcatagcc tcctaggcaa caagtggtct tgattgcgg cgagattacc tggaagaaca     300
gataacgaga tcaagaacta ctggaacaca catataaaga ggaagctttt gagcaaaggg     360
attgatccag ccactcatag agggatcaac gaggcaaaaa tttctgattt gaagaaaaca     420
aaggaccaaa ttgtaaaaga tgtttctttt gtgacaaagt tgaggaaaac agacaagtct     480
ggggaccaga agcaaaataa gtatattcga atgggttag tttgcaaaga agagagagtt      540
gttgttgaag aaaaaatagg cccagatttg aatcttgagc ttaggatcag tccaccatgg     600
caaaaccaga gagaaatatc tacttgcact gcgtcccgtt tttacatgga aaacgacatg     660
gagtgtagta gtgaaactgt gaaatgtcaa acagagaata gtagcagcat tagctattct     720
tctattgata ttagtagtag taacgttggt tatgacttct gggtttgaa gacaagaatt      780 ttggattttc gaagcttgga aatgaaataa                                      810

<210> SEQ ID NO 96
<211> LENGTH: 269
<212> TYPE: PRT
<213> ORGANISM: Arabidopsis thaliana

<400> SEQUENCE: 96

Met Gly Arg Ser Pro Cys Cys Glu Lys Glu His Met Asn Lys Gly Ala
1               5                   10                  15

Trp Thr Lys Glu Glu Asp Glu Arg Leu Val Ser Tyr Ile Lys Ser His
            20                  25                  30

Gly Glu Gly Cys Trp Arg Ser Leu Pro Arg Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr His Asp Glu Asp Glu Leu Ile Ile Lys
```

```
                65                  70                  75                  80
Leu His Ser Leu Leu Gly Asn Lys Trp Ser Leu Ile Ala Ala Arg Leu
                        85                  90                  95

Pro Gly Arg Thr Asp Asn Glu Ile Lys Asn Tyr Trp Asn Thr His Ile
                100                 105                 110

Lys Arg Lys Leu Leu Ser Lys Gly Ile Asp Pro Ala Thr His Arg Gly
                115                 120                 125

Ile Asn Glu Ala Lys Ile Ser Asp Leu Lys Lys Thr Lys Asp Gln Ile
        130                 135                 140

Val Lys Asp Val Ser Phe Val Thr Lys Phe Glu Glu Thr Asp Lys Ser
145                 150                 155                 160

Gly Asp Gln Lys Gln Asn Lys Tyr Ile Arg Asn Gly Leu Val Cys Lys
                165                 170                 175

Glu Glu Arg Val Val Val Glu Glu Lys Ile Gly Pro Asp Leu Asn Leu
                180                 185                 190

Glu Leu Arg Ile Ser Pro Pro Trp Gln Asn Gln Arg Glu Ile Ser Thr
            195                 200                 205

Cys Thr Ala Ser Arg Phe Tyr Met Glu Asn Asp Met Glu Cys Ser Ser
        210                 215                 220

Glu Thr Val Lys Cys Gln Thr Glu Asn Ser Ser Ile Ser Tyr Ser
225                 230                 235                 240

Ser Ile Asp Ile Ser Ser Ser Asn Val Gly Tyr Asp Phe Leu Gly Leu
                245                 250                 255

Lys Thr Arg Ile Leu Asp Phe Arg Ser Leu Glu Met Lys
                260                 265
```

<210> SEQ ID NO 97
<211> LENGTH: 942
<212> TYPE: DNA
<213> ORGANISM: Dahlia pinnata

<400> SEQUENCE: 97

```
atgggaagat caccttgttg tgaaaaagca cacaccaaca aaggagcatg gactaaagaa      60
gaagatgatc ggttaattgc ttatattaga actcacggcg aaggatgctg gcggtcccta     120
cctaaggccg ccggcctcct tcgctgcggc aagagctgcc gcctccggtg gatcaattac     180
ctccgcccgg accccaaacg tggcaacttc accgaagatg aagatgaact catcatcaaa     240
ctccatagcc ttcttggtaa caagtggtca ttgattgctg aagattgcc cggaagaaca      300
gataacgaga taagaattta ctggaacact catattagaa aaagcttttt aaaccggggg     360
attgatccga caactcatcg gccggtgaac gatagtccaa ctaattatcc caccaccaca     420
accgtcaccg ccaccaccac aactaacaac aataataata acaattcatc tctagatgtc     480
acaaccatat cttttgcaaa ccctcctcca accactcatc atctagttaa agaagaagta     540
gaagatgaac aaaacataa ctccgacgga agcgaccacc ggaaaatcaa cagcgtgttg     600
ccggaaattc aagaaagatg tccggatttg aatttggagt tgagaatgag cccacctcat     660
cattcatcat cttcatcctc atcatcatca tcatcatcat catcacacat acatccacaa     720
cttcaacaag aaaaccacta tcaccaccaa ctactaaaga cgggaggaag aagtcctcct     780
ggtggcacta atatatgctt tgcatgcagt ttaggtatag agaatagcaa ggagtgcagc     840
tgtaccaaca atattaatgg tacaagcagt agcagcactg gttatgattt cttaggtttg     900
aaaactcgtg ttttggacta cagaagctta gagatgaaat ga                        942
```

<210> SEQ ID NO 98
<211> LENGTH: 313
<212> TYPE: PRT
<213> ORGANISM: Dahlia pinnata

<400> SEQUENCE: 98

| | | | | | | | | | | | | | | | |
|---|---|---|---|---|---|---|---|---|---|---|---|---|---|---|---|
| Met | Gly | Arg | Ser | Pro | Cys | Cys | Glu | Lys | Ala | His | Thr | Asn | Lys | Gly | Ala |
| 1 | | | | 5 | | | | | 10 | | | | | 15 | |
| Trp | Thr | Lys | Glu | Glu | Asp | Asp | Arg | Leu | Ile | Ala | Tyr | Ile | Arg | Thr | His |
| | | | 20 | | | | | 25 | | | | | 30 | | |
| Gly | Glu | Gly | Cys | Trp | Arg | Ser | Leu | Pro | Lys | Ala | Ala | Gly | Leu | Leu | Arg |
| | | 35 | | | | | 40 | | | | | 45 | | | |
| Cys | Gly | Lys | Ser | Cys | Arg | Leu | Arg | Trp | Ile | Asn | Tyr | Leu | Arg | Pro | Asp |
| | 50 | | | | | 55 | | | | | 60 | | | | |
| Pro | Lys | Arg | Gly | Asn | Phe | Thr | Glu | Asp | Glu | Asp | Glu | Leu | Ile | Ile | Lys |
| 65 | | | | | 70 | | | | | 75 | | | | | 80 |
| Leu | His | Ser | Leu | Leu | Gly | Asn | Lys | Trp | Ser | Leu | Ile | Ala | Gly | Arg | Leu |
| | | | | 85 | | | | | 90 | | | | | 95 | |
| Pro | Gly | Arg | Thr | Asp | Asn | Glu | Ile | Lys | Asn | Tyr | Trp | Asn | Thr | His | Ile |
| | | | 100 | | | | | 105 | | | | | 110 | | |
| Arg | Arg | Lys | Leu | Leu | Asn | Arg | Gly | Ile | Asp | Pro | Thr | Thr | His | Arg | Pro |
| | | | 115 | | | | | 120 | | | | | 125 | | |
| Val | Asn | Asp | Ser | Pro | Thr | Asn | Tyr | Pro | Thr | Thr | Thr | Val | Thr | Ala | |
| | 130 | | | | | 135 | | | | | 140 | | | | |
| Thr | Thr | Thr | Thr | Asn | Asn | Asn | Asn | Asn | Asn | Ser | Ser | Leu | Asp | Val | |
| 145 | | | | | 150 | | | | | 155 | | | | | 160 |
| Thr | Thr | Ile | Ser | Phe | Ala | Asn | Pro | Pro | Thr | Thr | His | His | Leu | Val | |
| | | | | 165 | | | | | 170 | | | | | 175 | |
| Lys | Glu | Glu | Val | Glu | Asp | Glu | Pro | Lys | His | Asn | Ser | Asp | Gly | Ser | Asp |
| | | | 180 | | | | | 185 | | | | | 190 | | |
| His | Arg | Lys | Ile | Asn | Ser | Val | Leu | Pro | Glu | Ile | Gln | Glu | Arg | Cys | Pro |
| | | | 195 | | | | | 200 | | | | | 205 | | |
| Asp | Leu | Asn | Leu | Glu | Leu | Arg | Met | Ser | Pro | Pro | His | His | Ser | Ser | Ser |
| | 210 | | | | | 215 | | | | | 220 | | | | |
| Ser | Ser | Ser | Ser | Ser | Ser | Ser | Ser | Ser | Ser | His | Ile | His | Pro | Gln | |
| 225 | | | | | 230 | | | | | 235 | | | | | 240 |
| Leu | Gln | Gln | Glu | Asn | His | Tyr | His | His | Gln | Leu | Leu | Lys | Thr | Gly | Gly |
| | | | | 245 | | | | | 250 | | | | | 255 | |
| Arg | Ser | Pro | Pro | Gly | Gly | Thr | Asn | Ile | Cys | Phe | Ala | Cys | Ser | Leu | Gly |
| | | | 260 | | | | | 265 | | | | | 270 | | |
| Ile | Glu | Asn | Ser | Lys | Glu | Cys | Ser | Cys | Thr | Asn | Asn | Ile | Asn | Gly | Thr |
| | | | 275 | | | | | 280 | | | | | 285 | | |
| Ser | Ser | Ser | Ser | Thr | Gly | Tyr | Asp | Phe | Leu | Gly | Leu | Lys | Thr | Arg | Val |
| | | 290 | | | | | 295 | | | | | 300 | | | |
| Leu | Asp | Tyr | Arg | Ser | Leu | Glu | Met | Lys | | | | | | | |
| 305 | | | | 310 | | | | | | | | | | | |

<210> SEQ ID NO 99
<211> LENGTH: 663
<212> TYPE: DNA
<213> ORGANISM: Dendrobium sp. XMW-2002-10

<400> SEQUENCE: 99

```
atggggaggt ctgcttgttg tgagaaagca cacaccaaca aaggggcgtg gactaaagag    60
gaggatgaga ggctcatcgc tcacatccgc actcatggtg aaggatgttg gcgttcactc   120
```

| | |
|---|---|
| cccaaggctg ctggccttct tcgttgtggc aaaagctgtc gtcttcgttg gatcaattat | 180 |
| cttcgccctg acctcaagcg tgggaacttc accgatgagg aggatgaact catcatcaag | 240 |
| cttcatagcc tccttggcaa taatggtct ttgatagctg gaagactacc aggaagaact | 300 |
| gacaatgaga tcaaaaacta ctggaacact catatacgaa ggaagctact caataggga | 360 |
| atagatcccg cgacacatcg tcccgtatcc actgccacgg cttcgaatct taccatgtct | 420 |
| ttcagtagtg gcagttctgt gaaggataag agaaccagca gcagcagcag cagcagcaga | 480 |
| gttggcagaa tatctgcttt gctgccgcgt tgtcctgatc taaatcttga cctctgcatc | 540 |
| agcccttcat tggaggagca gatgccacag gacttattgg ttgaggagag caactgtgga | 600 |
| ggtgagtttc ttaggctagg cagcagcttt ctgcttgatt acagaagctt ggaaatgaag | 660 |
| tga | 663 |

```
<210> SEQ ID NO 100
<211> LENGTH: 220
<212> TYPE: PRT
<213> ORGANISM: Dendrobium sp. XMW-2002-10

<400> SEQUENCE: 100

Met Gly Arg Ser Ala Cys Cys Glu Lys Ala His Thr Asn Lys Gly Ala
1               5                   10                  15

Trp Thr Lys Glu Glu Asp Glu Arg Leu Ile Ala His Ile Arg Thr His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Asp Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Asn Arg Gly Ile Asp Pro Ala Thr His Arg Pro
        115                 120                 125

Val Ser Thr Ala Thr Ala Ser Asn Leu Thr Met Ser Phe Ser Ser Gly
    130                 135                 140

Ser Ser Val Lys Asp Lys Arg Thr Ser Ser Ser Ser Ser Ser Ser Arg
145                 150                 155                 160

Val Gly Arg Ile Ser Ala Leu Leu Pro Arg Cys Pro Asp Leu Asn Leu
                165                 170                 175

Asp Leu Cys Ile Ser Pro Ser Leu Glu Glu Gln Met Pro Gln Asp Leu
            180                 185                 190

Leu Val Glu Glu Ser Asn Cys Gly Gly Glu Phe Leu Arg Leu Gly Ser
        195                 200                 205

Ser Phe Leu Leu Asp Tyr Arg Ser Leu Glu Met Lys
    210                 215                 220

<210> SEQ ID NO 101
<211> LENGTH: 879
<212> TYPE: DNA
<213> ORGANISM: Thellungiella halophila

<400> SEQUENCE: 101
```

| | |
|---|---|
| atgggaaggt caccatgttg tgaaaaagct cacacgaaca aaggagcatg gacgaaagaa | 60 |

-continued

```
gaggacgaga gactcatagc ttacattaaa gctcatggcg aaggctgctg gagatctctc      120
cctaaagccg ccggccttct ccgctgtggc aaaagctgcc gtctccggtg atcaactat      180 ctccggcctg accttaagcg cggaaacttc accgaggaag aggatgagct catcatcaag      240
ctccatagcc ttcttggcaa caaatggtcg cttatcgcgg ggagattacc gggaagaaca      300
gataacgaga taaagaacta ttggaacaca catatacgaa gaaagctgat aaacagaggg      360
attgatccaa cgactcatag accaatccaa gaatcatcag cttctcagga ttctaaacct      420
atacagctag aaccaatcac gagtaataac accattaata tctccttcac ttcttcctct      480
tctactccaa aggtcgaaac tttccaggaa agcataagtt ttccgggaaa gtcagagaaa      540
atctcaatgc ttacgttcaa agaagaaaaa gatgagcgcc caatcgaaga aaagttccca      600
gatttgaatc ttgagctcag aatcagtctt cctgatgttg ctgatcgtcg ccaaggcttg      660
gtgggagagg ggatcttaac gacgccgcgt tgtttcaact gcagcttagg gatgataaac      720
ggcatggagt gcagatgtgg aagaaggaga tgcgatgttg tcggaggtag cagcggcagt      780
ggcaacggga gtgacataag caacggattt gattttttag ggttggcaaa gaaagaaacc      840
acttctcttt tgggttttag aagtttggag atgaaataa                             879
```

<210> SEQ ID NO 102
<211> LENGTH: 292
<212> TYPE: PRT
<213> ORGANISM: Thellungiella halophila

<400> SEQUENCE: 102

```
Met Gly Arg Ser Pro Cys Cys Glu Lys Ala His Thr Asn Lys Gly Ala
1               5                   10                  15

Trp Thr Lys Glu Glu Asp Glu Arg Leu Ile Ala Tyr Ile Lys Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Ile Asn Arg Gly Ile Asp Pro Thr Thr His Arg Pro
        115                 120                 125

Ile Gln Glu Ser Ser Ala Ser Gln Asp Ser Lys Pro Ile Gln Leu Glu
    130                 135                 140

Pro Ile Thr Ser Asn Asn Thr Ile Asn Ile Ser Phe Thr Ser Ser Ser
145                 150                 155                 160

Ser Thr Pro Lys Val Glu Thr Phe Gln Glu Ser Ile Ser Phe Pro Gly
                165                 170                 175

Lys Ser Glu Lys Ile Ser Met Leu Thr Phe Lys Glu Glu Lys Asp Glu
            180                 185                 190

Arg Pro Ile Glu Glu Lys Phe Pro Asp Leu Asn Leu Glu Leu Arg Ile
        195                 200                 205

Ser Leu Pro Asp Val Ala Asp Arg Arg Gln Gly Leu Val Gly Glu Gly
    210                 215                 220
```

Ile Leu Thr Thr Pro Arg Cys Phe Asn Cys Ser Leu Gly Met Ile Asn
225                 230                 235                 240

Gly Met Glu Cys Arg Cys Gly Arg Arg Cys Asp Val Val Gly Gly
            245                 250                 255

Ser Ser Gly Ser Gly Asn Gly Ser Asp Ile Ser Asn Gly Phe Asp Phe
            260                 265                 270

Leu Gly Leu Ala Lys Lys Glu Thr Thr Ser Leu Leu Gly Phe Arg Ser
            275                 280                 285

Leu Glu Met Lys
    290

<210> SEQ ID NO 103
<211> LENGTH: 885
<212> TYPE: DNA
<213> ORGANISM: Brassica rapa

<400> SEQUENCE: 103

```
atgggaaggt caccgtgttg tgagaaagct cacacaaaca aggagcatg gacaaaagaa      60
gaggacgaga ggctcatagc ttacattaaa gctcacggcg aaggctgctg gagatctctc    120
cccaaagccg ccggccttct ccggtgtggc aaaagctgcc gtctccggtg gatcaactat    180
ctccggcctg accttaagcg tggaaacttc actgaagaag aggacgagct catcatcaag    240
ctccatagtc ttcttggcaa caaatggtcg cttattgctg ggagattacc gggaagaaca    300
gataacgaga taagaactat tggaacacat atatacgaaa gaaagcttat aaaccgaggg    360
attgatccaa caactcatag accaatccaa gaatcgtcag cttctcagga ttctaaaccg    420
acacacctag aagcaatcac aagtaacacc attaatatct ccttcgcctc ttcctcttct    480
actccgaaga tggaaatatt ccaggaaagc acaagttttc ctggaaaaca agagaaaatc    540
tcaatggtta cgttcaaaga agaaaaagac gagtgtccag ttgaagagaa ctttccagat    600
ttgaacctcg agctcagaat cagccttcct gatgttgttg atcatcatca tcaaggcttt    660
gtcggagagg gaaagacaac aacaccacga cgttgtttca aatgcagttt agggacgata    720
aacgggatgg agtgcagatg cggaagaatg agatacgatg ttgttggagg tagcaaaggc    780
agtggcaagg ggagtgacat gagcaacggg ttcgattttt tagggttggc aagaaagag    840
accaacactt gtcttttgg ttttagaagc ttggagatga ataa                       885
```

<210> SEQ ID NO 104
<211> LENGTH: 294
<212> TYPE: PRT
<213> ORGANISM: Brassica rapa

<400> SEQUENCE: 104

Met Gly Arg Ser Pro Cys Cys Glu Lys Ala His Thr Asn Lys Gly Ala
1               5                   10                  15

Trp Thr Lys Glu Glu Asp Glu Arg Leu Ile Ala Tyr Ile Lys Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

```
Pro Gly Arg Thr Asp Asn Glu Ile Lys Asn Tyr Trp Asn Thr His Ile
            100                 105                 110
Arg Arg Lys Leu Ile Asn Arg Gly Ile Asp Pro Thr Thr His Arg Pro
        115                 120                 125
Ile Gln Glu Ser Ser Ala Ser Gln Asp Ser Lys Pro Thr His Leu Glu
    130                 135                 140
Ala Ile Thr Ser Asn Thr Ile Asn Ile Ser Phe Ala Ser Ser Ser Ser
145                 150                 155                 160
Thr Pro Lys Met Glu Ile Phe Gln Glu Ser Thr Ser Phe Pro Gly Lys
                165                 170                 175
Gln Glu Lys Ile Ser Met Val Thr Phe Lys Glu Glu Lys Asp Glu Cys
            180                 185                 190
Pro Val Glu Glu Asn Phe Pro Asp Leu Asn Leu Glu Leu Arg Ile Ser
        195                 200                 205
Leu Pro Asp Val Val Asp His His His Gln Gly Phe Val Gly Glu Gly
    210                 215                 220
Lys Thr Thr Thr Pro Arg Arg Cys Phe Lys Cys Ser Leu Gly Thr Ile
225                 230                 235                 240
Asn Gly Met Glu Cys Arg Cys Gly Arg Met Arg Tyr Asp Val Val Gly
                245                 250                 255
Gly Ser Lys Gly Ser Gly Lys Gly Ser Asp Met Ser Asn Gly Phe Asp
            260                 265                 270
Phe Leu Gly Leu Ala Lys Lys Glu Thr Asn Thr Cys Leu Phe Gly Phe
        275                 280                 285
Arg Ser Leu Glu Met Lys
    290
```

<210> SEQ ID NO 105
<211> LENGTH: 885
<212> TYPE: DNA
<213> ORGANISM: Brassica rapa

<400> SEQUENCE: 105

```
atgggaaggt caccgtgttg tgagaaagct cacacaaaca aaggagcatg gacaaaagaa      60
gaggacgaga ggctcatagc ttacattaaa gctcacggcg aaggctgctg agatctctc     120
cccaaagccg ccggccttct ccggtgtggc aaaagctgcc gtctccggtg atcaactat     180
ctccggcctg accttaagcg tggaaacttc actgaagaag aggacgagct catcatcaag     240
ctccatagtc ttcttggcaa caaatggtcg cttattgctg ggagattacc gggaagaaca     300
gataacgaga taagaactta ttggaacaca catatacgaa gaaagcttat aaaccgaggg     360
attgatccaa caactcatag accaatccaa gaatcgtcag cttctcagga ttctaaaccg     420
acacacctag aagcaatcac aagtaacacc attaatatct ccttcgcctc ttcctcttct     480
actccgaaga tggaaatatt ccaggaaagc acaagttttc ctggaaaaca agagaaaatc     540
tcaatggtta cgttcaaaga agaaaaagac gagtgtccag ttgagagaa ctttccagat     600
ttgaacctcg agctcagaat cagccttcct gatgttgttg atcatcatca tcaaggcttt     660
gtcggagagg gaaagacaac aacaccacga cgttgtttca aatgcagttt agggacgata     720
aacgggatgg agtgcagatg cggaagaatg agatgcgatg ttgttggagg tagcaaaggc     780
agtggcaagg ggagtgacat gagcaacggg ttcgattttt tagggttggc aaagaaagag     840
accaacactt gtcttttttgg ttttagaagc ttggagatga aataa                    885
```

<210> SEQ ID NO 106

```
<211> LENGTH: 294
<212> TYPE: PRT
<213> ORGANISM: Brassica rapa

<400> SEQUENCE: 106

Met Gly Arg Ser Pro Cys Cys Glu Lys Ala His Thr Asn Lys Gly Ala
1               5                   10                  15

Trp Thr Lys Glu Glu Asp Glu Arg Leu Ile Ala Tyr Ile Lys Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Ile Asn Arg Gly Ile Asp Pro Thr Thr His Arg Pro
        115                 120                 125

Ile Gln Glu Ser Ser Ala Ser Gln Asp Ser Lys Pro Thr His Leu Glu
    130                 135                 140

Ala Ile Thr Ser Asn Thr Ile Asn Ile Ser Phe Ala Ser Ser Ser Ser
145                 150                 155                 160

Thr Pro Lys Met Glu Ile Phe Gln Glu Ser Thr Ser Phe Pro Gly Lys
                165                 170                 175

Gln Glu Lys Ile Ser Met Val Thr Phe Lys Glu Glu Lys Asp Glu Cys
            180                 185                 190

Pro Val Glu Glu Asn Phe Pro Asp Leu Asn Leu Glu Leu Arg Ile Ser
        195                 200                 205

Leu Pro Asp Val Val Asp His His Gln Gly Phe Val Gly Glu Gly
    210                 215                 220

Lys Thr Thr Thr Pro Arg Arg Cys Phe Lys Cys Ser Leu Gly Thr Ile
225                 230                 235                 240

Asn Gly Met Glu Cys Arg Cys Gly Arg Met Arg Cys Asp Val Val Gly
                245                 250                 255

Gly Ser Lys Gly Ser Gly Lys Gly Ser Asp Met Ser Asn Gly Phe Asp
            260                 265                 270

Phe Leu Gly Leu Ala Lys Lys Glu Thr Asn Thr Cys Leu Phe Gly Phe
        275                 280                 285

Arg Ser Leu Glu Met Lys
    290

<210> SEQ ID NO 107
<211> LENGTH: 705
<212> TYPE: DNA
<213> ORGANISM: Triticum aestivum

<400> SEQUENCE: 107
atggggagat cgccgtgctg cgagaaggcg cacaccaaca agggcgcgtg gacgagggag      60
gaggacgagc ggctggtggc ccacgtccgg gcgcacgggg agggctgctg gcgctcgctg     120
cccagcgccg ccggcctgct cgcctgcggc aagagctgcc gcctcaggtg gatcaactac     180
ctccgccccg gtctcaatcg cggcaacttc agccgcgacg aggacgagct catcggcgag     240
```

```
ctccatagcc tcctcggcaa caagtggtcg ctcatcgccg cgcgcctgcc cgggaggacg      300
gacaacgaga tcaagaacta ctggaacacg cacatccgga ggaagctgct gggcaggggg      360
atcgacccgg tcacgcaccg ccccctcacc gacgccgcca ccgtctcctt cgtccatcct      420
gcagaggcga ccaagcaaca ggcgacggag gagaggaagc cgcccagatg cccggacctc      480
aacctggacc tctgcatcag gctgccgttc aacaggagg aggaacggcc gccggcgaga       540
gcgtgcgcca gccggtgaa gatggagcag ctgcaccagg gcggcatctg cttccgctgc       600
agcatcctca gagtgagagg agcggcgacc gagtgcagct gcggaagcaa cttcctgggc      660
ctcagggccg gcaagctcga cttcgcaggc ctcgagatga aatag                     705
```

<210> SEQ ID NO 108
<211> LENGTH: 234
<212> TYPE: PRT
<213> ORGANISM: Triticum aestivum

<400> SEQUENCE: 108

Met Gly Arg Ser Pro Cys Cys Glu Lys Ala His Thr Asn Lys Gly Ala
1               5                   10                  15

Trp Thr Arg Glu Glu Asp Glu Arg Leu Val Ala His Val Arg Ala His
            20                  25                  30

Gly Glu Gly Cys Trp Arg Ser Leu Pro Ser Ala Ala Gly Leu Leu Arg
        35                  40                  45

Cys Gly Lys Ser Cys Arg Leu Arg Trp Ile Asn Tyr Leu Arg Pro Gly
    50                  55                  60

Leu Asn Arg Gly Asn Phe Ser Arg Asp Glu Asp Glu Leu Ile Gly Glu
65                  70                  75                  80

Leu His Ser Leu Leu Gly Asn Lys Trp Ser Leu Ile Ala Ala Arg Leu
                85                  90                  95

Pro Gly Arg Thr Asp Asn Glu Ile Lys Asn Tyr Trp Asn Thr His Ile
            100                 105                 110

Arg Arg Lys Leu Leu Gly Arg Gly Ile Asp Pro Val Thr His Arg Pro
        115                 120                 125

Leu Thr Asp Ala Ala Thr Val Ser Phe Val His Pro Ala Glu Ala Thr
    130                 135                 140

Lys Gln Gln Ala Thr Glu Glu Arg Lys Pro Pro Arg Cys Pro Asp Leu
145                 150                 155                 160

Asn Leu Asp Leu Cys Ile Arg Leu Pro Phe Gln Gln Glu Glu Glu Arg
                165                 170                 175

Pro Pro Ala Arg Ala Cys Ala Lys Pro Val Lys Met Glu Gln Leu His
            180                 185                 190

Gln Gly Gly Ile Cys Phe Arg Cys Ser Ile Leu Arg Val Arg Gly Ala
        195                 200                 205

Ala Thr Glu Cys Ser Cys Gly Ser Asn Phe Leu Gly Leu Arg Ala Gly
    210                 215                 220

Lys Leu Asp Phe Ala Gly Leu Glu Met Lys
225                 230

<210> SEQ ID NO 109
<211> LENGTH: 795
<212> TYPE: DNA
<213> ORGANISM: Sorghum bicolor

<400> SEQUENCE: 109
atggggaggt cgccgtgctg cgagaaggcg cacaccaaca agggcgcgtg gaccaaggag      60

```
gaggacgacc gcctcgtggc gtacatcaag gcgcacggcg agggttgctg gcgctcgctg    120
cccaaggccg ccggcctcct gcgctgcggc aagagctgcc gcctccggtg gatcaactac    180
ctccgccccg acctcaagcg cggcaacttc acggaagagg aggacgagct catcatcaag    240
ctccacagcc tcctcggcaa caaatggtcc ctgatcgctg gaaggctgcc gggaaggacg    300
gacaacgaga tcaagaacta ctggaacacg cacatccgga ggaagctgct gagcagggg    360 atcgacccgg tgacacaccg ccccatcaac gagcacacgt ccaacataac catctcgttc    420
gaggcggcgg cggccgcgcg tgaccgtgag gagaataagg gcgccgtgtt ccggctggag    480
gagcacaaca aggcgacggc ggcggcggcc gccgcgatcg gccgcgatca tcatcagaac    540
caccaccccg ccggcgactg gggccagggg aagccgctca gtgccccga cctcaacctg    600 gacctctgca tcagcccgcc ggcggcgccg tgccaggagg agaaggccat ggtgacgatg    660
aagcccgtga agcgggaggc cgggctctgc ttcagctgca gcctgggcct ccccaagagc    720
gccgactgca gtgcagcaa cttcctcgga ctcaggaccg ccatgctcga cttcagaagc    780
ctcgagatga aatga                                                    795
```

<210> SEQ ID NO 110
<211> LENGTH: 264
<212> TYPE: PRT
<213> ORGANISM: Sorghum bicolor

<400> SEQUENCE: 110

```
Met Gly Arg Ser Pro Cys Cys Glu Lys Ala His Thr Asn Lys Gly Ala
1               5                   10                  15

Trp Thr Lys Glu Glu Asp Asp Arg Leu Val Ala Tyr Ile Lys Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Arg Arg Lys Leu Leu Ser Arg Gly Ile Asp Pro Val Thr His Arg Pro
        115                 120                 125

Ile Asn Glu His Thr Ser Asn Ile Thr Ile Ser Phe Glu Ala Ala Ala
    130                 135                 140

Ala Ala Arg Asp Arg Glu Glu Asn Lys Gly Ala Val Phe Arg Leu Glu
145                 150                 155                 160

Glu His Asn Lys Ala Thr Ala Ala Ala Ala Ile Gly Arg Asp
                165                 170                 175

His His Gln Asn His His Pro Ala Gly Asp Trp Gly Gln Gly Lys Pro
            180                 185                 190

Leu Lys Cys Pro Asp Leu Asn Leu Asp Leu Cys Ile Ser Pro Pro Ala
        195                 200                 205

Ala Pro Cys Gln Glu Glu Lys Ala Met Val Thr Met Lys Pro Val Lys
    210                 215                 220

Arg Glu Ala Gly Leu Cys Phe Ser Cys Ser Leu Gly Leu Pro Lys Ser
225                 230                 235                 240
```

```
Ala Asp Cys Lys Cys Ser Asn Phe Leu Gly Leu Arg Thr Ala Met Leu
            245                 250                 255

Asp Phe Arg Ser Leu Glu Met Lys
        260

<210> SEQ ID NO 111
<211> LENGTH: 24
<212> TYPE: DNA
<213> ORGANISM: Artificial sequence
<220> FEATURE:
<223> OTHER INFORMATION: Primer

<400> SEQUENCE: 111
caccatgggg cggtcgccgt gctg                                            24

<210> SEQ ID NO 112
<211> LENGTH: 24
<212> TYPE: DNA
<213> ORGANISM: Artificial sequence
<220> FEATURE:
<223> OTHER INFORMATION: Primer

<400> SEQUENCE: 112
tcaaacaaaa aaaaacagcc caac                                            24

<210> SEQ ID NO 113
<211> LENGTH: 19
<212> TYPE: DNA
<213> ORGANISM: Artificial sequence
<220> FEATURE:
<223> OTHER INFORMATION: Primer

<400> SEQUENCE: 113
tcttttgtcg atgctcacc                                                  19

<210> SEQ ID NO 114
<211> LENGTH: 20
<212> TYPE: DNA
<213> ORGANISM: Artificial sequence
<220> FEATURE:
<223> OTHER INFORMATION: Primer

<400> SEQUENCE: 114
tcacttcatc tcgaggcctc                                                 20

<210> SEQ ID NO 115
<211> LENGTH: 26
<212> TYPE: DNA
<213> ORGANISM: Artificial sequence
<220> FEATURE:
<223> OTHER INFORMATION: Primer

<400> SEQUENCE: 115
aaggaatcgg tcaatacact acatgg                                          26

<210> SEQ ID NO 116
<211> LENGTH: 23
<212> TYPE: DNA
<213> ORGANISM: Artificial sequence
<220> FEATURE:
<223> OTHER INFORMATION: Primer

<400> SEQUENCE: 116
aagaccaatg cggagcatat acg                                             23
```

```
<210> SEQ ID NO 117
<211> LENGTH: 41
<212> TYPE: DNA
<213> ORGANISM: Artificial sequence
<220> FEATURE:
<223> OTHER INFORMATION: Primer

<400> SEQUENCE: 117
gcgtaatacg actcactata gggtgctgcg agaaggcgca c                41

<210> SEQ ID NO 118
<211> LENGTH: 43
<212> TYPE: DNA
<213> ORGANISM: Artificial sequence
<220> FEATURE:
<223> OTHER INFORMATION: Primer

<400> SEQUENCE: 118
gcgtaatacg actcactata gggtcatctc gaggcctctg aag              43

<210> SEQ ID NO 119
<211> LENGTH: 18
<212> TYPE: DNA
<213> ORGANISM: Artificial sequence
<220> FEATURE:
<223> OTHER INFORMATION: Primer

<400> SEQUENCE: 119
tgctgcgaga aggcgcac                                          18

<210> SEQ ID NO 120
<211> LENGTH: 20
<212> TYPE: DNA
<213> ORGANISM: Artificial sequence
<220> FEATURE:
<223> OTHER INFORMATION: Primer

<400> SEQUENCE: 120
tcatctcgag gcctctgaag                                        20

<210> SEQ ID NO 121
<211> LENGTH: 20
<212> TYPE: DNA
<213> ORGANISM: Artificial sequence
<220> FEATURE:
<223> OTHER INFORMATION: Primer

<400> SEQUENCE: 121
tcggcatgct cctcgacttc                                        20

<210> SEQ ID NO 122
<211> LENGTH: 20
<212> TYPE: DNA
<213> ORGANISM: Artificial sequence
<220> FEATURE:
<223> OTHER INFORMATION: Primer

<400> SEQUENCE: 122
accagccgct cgcatctttc                                        20

<210> SEQ ID NO 123
<211> LENGTH: 22
<212> TYPE: DNA
<213> ORGANISM: Artificial sequence
<220> FEATURE:
<223> OTHER INFORMATION: Primer
```

```
<400> SEQUENCE: 123
aggcctcgag atgaagtgaa ac                                              22

<210> SEQ ID NO 124
<211> LENGTH: 22
<212> TYPE: DNA
<213> ORGANISM: Artificial sequence
<220> FEATURE:
<223> OTHER INFORMATION: Primer

<400> SEQUENCE: 124
agcccaacaa acaaacgaaa tt                                              22

<210> SEQ ID NO 125
<211> LENGTH: 22
<212> TYPE: DNA
<213> ORGANISM: Artificial sequence
<220> FEATURE:
<223> OTHER INFORMATION: Primer

<400> SEQUENCE: 125
ctcaatctcg acctctgcat ca                                              22

<210> SEQ ID NO 126
<211> LENGTH: 21
<212> TYPE: DNA
<213> ORGANISM: Artificial sequence
<220> FEATURE:
<223> OTHER INFORMATION: Primer

<400> SEQUENCE: 126
acgagctcct ggtcctcttc t                                               21

<210> SEQ ID NO 127
<211> LENGTH: 21
<212> TYPE: DNA
<213> ORGANISM: Artificial sequence
<220> FEATURE:
<223> OTHER INFORMATION: Primer

<400> SEQUENCE: 127
atgagctcct ggtcctcttc t                                               21

<210> SEQ ID NO 128
<211> LENGTH: 18
<212> TYPE: DNA
<213> ORGANISM: Artificial sequence
<220> FEATURE:
<223> OTHER INFORMATION: Primer

<400> SEQUENCE: 128
gagctcctgg tcctcttc                                                   18

<210> SEQ ID NO 129
<211> LENGTH: 22
<212> TYPE: DNA
<213> ORGANISM: Artificial sequence
<220> FEATURE:
<223> OTHER INFORMATION: Primer

<400> SEQUENCE: 129
catatagtgt gcgtgcgtgt gt                                              22

<210> SEQ ID NO 130
<211> LENGTH: 15
```

```
<212> TYPE: DNA
<213> ORGANISM: Artificial sequence
<220> FEATURE:
<223> OTHER INFORMATION: Primer

<400> SEQUENCE: 130
ctggcccgcc aatcg                                                    15

<210> SEQ ID NO 131
<211> LENGTH: 20
<212> TYPE: DNA
<213> ORGANISM: Artificial sequence
<220> FEATURE:
<223> OTHER INFORMATION: Primer

<400> SEQUENCE: 131
gggcagttca gcaaccagat                                               20

<210> SEQ ID NO 132
<211> LENGTH: 19
<212> TYPE: DNA
<213> ORGANISM: Artificial sequence
<220> FEATURE:
<223> OTHER INFORMATION: Primer

<400> SEQUENCE: 132
cgcgtttccg ggactctag                                                19

<210> SEQ ID NO 133
<211> LENGTH: 22
<212> TYPE: DNA
<213> ORGANISM: Artificial sequence
<220> FEATURE:
<223> OTHER INFORMATION: Primer

<400> SEQUENCE: 133
ttgagatggt tgtgtccgct ta                                            22

<210> SEQ ID NO 134
<211> LENGTH: 20
<212> TYPE: DNA
<213> ORGANISM: Artificial sequence
<220> FEATURE:
<223> OTHER INFORMATION: Primer

<400> SEQUENCE: 134
aggcggtccc ttctctcatt                                               20

<210> SEQ ID NO 135
<211> LENGTH: 18
<212> TYPE: DNA
<213> ORGANISM: Artificial sequence
<220> FEATURE:
<223> OTHER INFORMATION: Primer

<400> SEQUENCE: 135
caaccgcgtg ttcaacga                                                 18

<210> SEQ ID NO 136
<211> LENGTH: 22
<212> TYPE: DNA
<213> ORGANISM: Artificial sequence
<220> FEATURE:
<223> OTHER INFORMATION: Primer

<400> SEQUENCE: 136
```

```
cggtgtagaa ctcgagcagc tt                                              22

<210> SEQ ID NO 137
<211> LENGTH: 27
<212> TYPE: DNA
<213> ORGANISM: Artificial sequence
<220> FEATURE:
<223> OTHER INFORMATION: Primer

<400> SEQUENCE: 137
ctcttctatt tgtgcgtgta actgtgt                                         27

<210> SEQ ID NO 138
<211> LENGTH: 22
<212> TYPE: DNA
<213> ORGANISM: Artificial sequence
<220> FEATURE:
<223> OTHER INFORMATION: Primer

<400> SEQUENCE: 138
cagccctata gcatcgacat ga                                              22

<210> SEQ ID NO 139
<211> LENGTH: 23
<212> TYPE: DNA
<213> ORGANISM: Artificial sequence
<220> FEATURE:
<223> OTHER INFORMATION: Primer

<400> SEQUENCE: 139
cgagcagatc atgaaaggtt acc                                             23

<210> SEQ ID NO 140
<211> LENGTH: 18
<212> TYPE: DNA
<213> ORGANISM: Artificial sequence
<220> FEATURE:
<223> OTHER INFORMATION: Primer

<400> SEQUENCE: 140
cagccagccg tccttgtc                                                   18

<210> SEQ ID NO 141
<211> LENGTH: 23
<212> TYPE: DNA
<213> ORGANISM: Artificial sequence
<220> FEATURE:
<223> OTHER INFORMATION: Primer

<400> SEQUENCE: 141
ccgtctttct tttttggct ctt                                              23

<210> SEQ ID NO 142
<211> LENGTH: 24
<212> TYPE: DNA
<213> ORGANISM: Artificial sequence
<220> FEATURE:
<223> OTHER INFORMATION: Primer

<400> SEQUENCE: 142
gcatgaaaat gatgacagtt tcca                                            24

<210> SEQ ID NO 143
<211> LENGTH: 17
<212> TYPE: DNA
<213> ORGANISM: Artificial sequence
```

```
<220> FEATURE:
<223> OTHER INFORMATION: Primer

<400> SEQUENCE: 143
gcgtcgtggc tcgtcaa                                               17

<210> SEQ ID NO 144
<211> LENGTH: 19
<212> TYPE: DNA
<213> ORGANISM: Artificial sequence
<220> FEATURE:
<223> OTHER INFORMATION: Primer

<400> SEQUENCE: 144
tcgggtcatc tgggttcct                                             19

<210> SEQ ID NO 145
<211> LENGTH: 22
<212> TYPE: DNA
<213> ORGANISM: Artificial sequence
<220> FEATURE:
<223> OTHER INFORMATION: Primer

<400> SEQUENCE: 145
tcacatcaag catccaccat ct                                         22

<210> SEQ ID NO 146
<211> LENGTH: 21
<212> TYPE: DNA
<213> ORGANISM: Artificial sequence
<220> FEATURE:
<223> OTHER INFORMATION: Primer

<400> SEQUENCE: 146
gttctcgtgt ccgaggtgtg t                                          21

<210> SEQ ID NO 147
<211> LENGTH: 21
<212> TYPE: DNA
<213> ORGANISM: Artificial sequence
<220> FEATURE:
<223> OTHER INFORMATION: Primer

<400> SEQUENCE: 147
gcagaaggag cagcagtcat c                                          21

<210> SEQ ID NO 148
<211> LENGTH: 20
<212> TYPE: DNA
<213> ORGANISM: Artificial sequence
<220> FEATURE:
<223> OTHER INFORMATION: Primer

<400> SEQUENCE: 148
cgagcggcaa tagtcgttgt                                            20

<210> SEQ ID NO 149
<211> LENGTH: 20
<212> TYPE: DNA
<213> ORGANISM: Artificial sequence
<220> FEATURE:
<223> OTHER INFORMATION: Primer

<400> SEQUENCE: 149
caccatgcac cacctctcaa                                            20
```

```
<210> SEQ ID NO 150
<211> LENGTH: 22
<212> TYPE: DNA
<213> ORGANISM: Artificial sequence
<220> FEATURE:
<223> OTHER INFORMATION: Primer

<400> SEQUENCE: 150
atgcaaatcc ccatccagat at                                          22

<210> SEQ ID NO 151
<211> LENGTH: 15
<212> TYPE: DNA
<213> ORGANISM: Artificial sequence
<220> FEATURE:
<223> OTHER INFORMATION: Primer

<400> SEQUENCE: 151
tgggccggga tttcg                                                  15

<210> SEQ ID NO 152
<211> LENGTH: 20
<212> TYPE: DNA
<213> ORGANISM: Artificial sequence
<220> FEATURE:
<223> OTHER INFORMATION: Primer

<400> SEQUENCE: 152
ccatgatcgt cagcgacaaa                                             20

<210> SEQ ID NO 153
<211> LENGTH: 18
<212> TYPE: DNA
<213> ORGANISM: Artificial sequence
<220> FEATURE:
<223> OTHER INFORMATION: Primer

<400> SEQUENCE: 153
tgtagcacga gaacttcc                                               18

<210> SEQ ID NO 154
<211> LENGTH: 19
<212> TYPE: DNA
<213> ORGANISM: Artificial sequence
<220> FEATURE:
<223> OTHER INFORMATION: Primer

<400> SEQUENCE: 154
acggcatgct tcaccaaca                                              19

<210> SEQ ID NO 155
<211> LENGTH: 17
<212> TYPE: DNA
<213> ORGANISM: Artificial sequence
<220> FEATURE:
<223> OTHER INFORMATION: Primer

<400> SEQUENCE: 155
ggccacgtcc gcatttc                                                17

<210> SEQ ID NO 156
<211> LENGTH: 22
<212> TYPE: DNA
<213> ORGANISM: Artificial sequence
<220> FEATURE:
<223> OTHER INFORMATION: Primer
```

```
<400> SEQUENCE: 156
gcatggtgac taccacattg ga                                          22

<210> SEQ ID NO 157
<211> LENGTH: 21
<212> TYPE: DNA
<213> ORGANISM: Artificial sequence
<220> FEATURE:
<223> OTHER INFORMATION: Primer

<400> SEQUENCE: 157
gacaaagtgt tcacagcaat g                                           21

<210> SEQ ID NO 158
<211> LENGTH: 21
<212> TYPE: DNA
<213> ORGANISM: Artificial sequence
<220> FEATURE:
<223> OTHER INFORMATION: Primer

<400> SEQUENCE: 158
taacagatwg gaagaggagc a                                           21

<210> SEQ ID NO 159
<211> LENGTH: 20
<212> TYPE: DNA
<213> ORGANISM: Artificial sequence
<220> FEATURE:
<223> OTHER INFORMATION: Primer

<400> SEQUENCE: 159
tcaacacaat ggtggaatgc                                             20

<210> SEQ ID NO 160
<211> LENGTH: 20
<212> TYPE: DNA
<213> ORGANISM: Artificial sequence
<220> FEATURE:
<223> OTHER INFORMATION: Primer

<400> SEQUENCE: 160
actttgggac gtttggttca                                             20

<210> SEQ ID NO 161
<211> LENGTH: 21
<212> TYPE: DNA
<213> ORGANISM: Artificial sequence
<220> FEATURE:
<223> OTHER INFORMATION: Primer

<400> SEQUENCE: 161
cttctcaacc atcccaacat t                                           21

<210> SEQ ID NO 162
<211> LENGTH: 21
<212> TYPE: DNA
<213> ORGANISM: Artificial sequence
<220> FEATURE:
<223> OTHER INFORMATION: Primer

<400> SEQUENCE: 162
ctaacaacaa aagccactgg a                                           21

<210> SEQ ID NO 163
```

```
<211> LENGTH: 20
<212> TYPE: DNA
<213> ORGANISM: Artificial sequence
<220> FEATURE:
<223> OTHER INFORMATION: Primer

<400> SEQUENCE: 163
ggctgccaat ccatgatgct                                              20

<210> SEQ ID NO 164
<211> LENGTH: 21
<212> TYPE: DNA
<213> ORGANISM: Artificial sequence
<220> FEATURE:
<223> OTHER INFORMATION: Primer

<400> SEQUENCE: 164
gcaacagatt gactgccatc a                                            21

<210> SEQ ID NO 165
<211> LENGTH: 20
<212> TYPE: DNA
<213> ORGANISM: Artificial sequence
<220> FEATURE:
<223> OTHER INFORMATION: Primer

<400> SEQUENCE: 165
tggctgaggt gatcaagaac                                              20

<210> SEQ ID NO 166
<211> LENGTH: 20
<212> TYPE: DNA
<213> ORGANISM: Artificial sequence
<220> FEATURE:
<223> OTHER INFORMATION: Primer

<400> SEQUENCE: 166
tatgggaggt tggggaagtc                                              20

<210> SEQ ID NO 167
<211> LENGTH: 20
<212> TYPE: DNA
<213> ORGANISM: Artificial sequence
<220> FEATURE:
<223> OTHER INFORMATION: Primer

<400> SEQUENCE: 167
acaccctatg gaatggatca                                              20

<210> SEQ ID NO 168
<211> LENGTH: 21
<212> TYPE: DNA
<213> ORGANISM: Artificial sequence
<220> FEATURE:
<223> OTHER INFORMATION: Primer

<400> SEQUENCE: 168
ccttgttgag ttccaatacg a                                            21

<210> SEQ ID NO 169
<211> LENGTH: 20
<212> TYPE: DNA
<213> ORGANISM: Artificial sequence
<220> FEATURE:
<223> OTHER INFORMATION: Primer

<400> SEQUENCE: 169
```

```
gaaactctac gacttcaccc                                              20

<210> SEQ ID NO 170
<211> LENGTH: 20
<212> TYPE: DNA
<213> ORGANISM: Artificial sequence
<220> FEATURE:
<223> OTHER INFORMATION: Primer

<400> SEQUENCE: 170
tgactttgcc ggaatatggt                                              20

<210> SEQ ID NO 171
<211> LENGTH: 20
<212> TYPE: DNA
<213> ORGANISM: Artificial sequence
<220> FEATURE:
<223> OTHER INFORMATION: Primer

<400> SEQUENCE: 171
cctgcaaatg ggaaggtgat                                              20

<210> SEQ ID NO 172
<211> LENGTH: 20
<212> TYPE: DNA
<213> ORGANISM: Artificial sequence
<220> FEATURE:
<223> OTHER INFORMATION: Primer

<400> SEQUENCE: 172
cagtcctttc tttgcctcct                                              20

<210> SEQ ID NO 173
<211> LENGTH: 20
<212> TYPE: DNA
<213> ORGANISM: Artificial sequence
<220> FEATURE:
<223> OTHER INFORMATION: Primer

<400> SEQUENCE: 173
ctcgggagaa agagcatcac                                              20

<210> SEQ ID NO 174
<211> LENGTH: 20
<212> TYPE: DNA
<213> ORGANISM: Artificial sequence
<220> FEATURE:
<223> OTHER INFORMATION: Primer

<400> SEQUENCE: 174
cctctccatt gcagtgttga                                              20

<210> SEQ ID NO 175
<211> LENGTH: 21
<212> TYPE: DNA
<213> ORGANISM: Artificial sequence
<220> FEATURE:
<223> OTHER INFORMATION: Primer

<400> SEQUENCE: 175
atgtgacgaa gccaagggta a                                            21

<210> SEQ ID NO 176
<211> LENGTH: 21
<212> TYPE: DNA
```

```
<213> ORGANISM: Artificial sequence
<220> FEATURE:
<223> OTHER INFORMATION: Primer

<400> SEQUENCE: 176
gtaggaattg gaaggtgacc t                                              21

<210> SEQ ID NO 177
<211> LENGTH: 19
<212> TYPE: DNA
<213> ORGANISM: Artificial sequence
<220> FEATURE:
<223> OTHER INFORMATION: Primer

<400> SEQUENCE: 177
caccgctgtc acgtttcgt                                                 19

<210> SEQ ID NO 178
<211> LENGTH: 23
<212> TYPE: DNA
<213> ORGANISM: Artificial sequence
<220> FEATURE:
<223> OTHER INFORMATION: Primer

<400> SEQUENCE: 178
agggcttgcc caactaaact atc                                            23

<210> SEQ ID NO 179
<211> LENGTH: 20
<212> TYPE: DNA
<213> ORGANISM: Artificial sequence
<220> FEATURE:
<223> OTHER INFORMATION: Primer

<400> SEQUENCE: 179
tgcagagagt caggccattg                                                20

<210> SEQ ID NO 180
<211> LENGTH: 18
<212> TYPE: DNA
<213> ORGANISM: Artificial sequence
<220> FEATURE:
<223> OTHER INFORMATION: Primer

<400> SEQUENCE: 180
cggcgggaag gtttcatt                                                  18

<210> SEQ ID NO 181
<211> LENGTH: 20
<212> TYPE: DNA
<213> ORGANISM: Artificial sequence
<220> FEATURE:
<223> OTHER INFORMATION: Primer

<400> SEQUENCE: 181
gcgagaagtt gcggagaaga                                                20

<210> SEQ ID NO 182
<211> LENGTH: 23
<212> TYPE: DNA
<213> ORGANISM: Artificial sequence
<220> FEATURE:
<223> OTHER INFORMATION: Primer

<400> SEQUENCE: 182
catcatttca tgggcttcta acc                                            23
```

<210> SEQ ID NO 183
<211> LENGTH: 50
<212> TYPE: DNA
<213> ORGANISM: Artificial sequence
<220> FEATURE:
<223> OTHER INFORMATION: Primer

<400> SEQUENCE: 183
cggtaccagt ccacctaccg ccacctaccg ccacctaccg ctgttctcga            50

<210> SEQ ID NO 184
<211> LENGTH: 50
<212> TYPE: DNA
<213> ORGANISM: Artificial sequence
<220> FEATURE:
<223> OTHER INFORMATION: Primer

<400> SEQUENCE: 184
tcgagaacag cggtaggtgg cggtaggtgg cggtaggtgg actggtaccg            50

<210> SEQ ID NO 185
<211> LENGTH: 50
<212> TYPE: DNA
<213> ORGANISM: Artificial sequence
<220> FEATURE:
<223> OTHER INFORMATION: Primer

<400> SEQUENCE: 185
cggtaccagt ccaccaaccg ccaccaaccg ccaccaaccg ctgttctcga            50

<210> SEQ ID NO 186
<211> LENGTH: 50
<212> TYPE: DNA
<213> ORGANISM: Artificial sequence
<220> FEATURE:
<223> OTHER INFORMATION: Primer

<400> SEQUENCE: 186
tcgagaacag cggttggtgg cggttggtgg cggttggtgg actggtaccg            50

<210> SEQ ID NO 187
<211> LENGTH: 41
<212> TYPE: DNA
<213> ORGANISM: Artificial sequence
<220> FEATURE:
<223> OTHER INFORMATION: Primer

<400> SEQUENCE: 187
ccagtccacc taactctacc taactctacc taacgctgtt c            41

<210> SEQ ID NO 188
<211> LENGTH: 41
<212> TYPE: DNA
<213> ORGANISM: Artificial sequence
<220> FEATURE:
<223> OTHER INFORMATION: Primer

<400> SEQUENCE: 188
gaacagcgtt aggtagagtt aggtagagtt aggtggactg g            41

<210> SEQ ID NO 189
<211> LENGTH: 41
<212> TYPE: DNA
<213> ORGANISM: Artificial sequence
<220> FEATURE:

```
<223> OTHER INFORMATION: Primer

<400> SEQUENCE: 189
ccagtccacc aaactctacc aaactctacc aaacgctgtt c                    41

<210> SEQ ID NO 190
<211> LENGTH: 41
<212> TYPE: DNA
<213> ORGANISM: Artificial sequence
<220> FEATURE:
<223> OTHER INFORMATION: Primer

<400> SEQUENCE: 190
gaacagcgtt tggtagagtt tggtagagtt tggtggactg g                    41

<210> SEQ ID NO 191
<211> LENGTH: 47
<212> TYPE: DNA
<213> ORGANISM: Artificial sequence
<220> FEATURE:
<223> OTHER INFORMATION: Primer

<400> SEQUENCE: 191
cttaactctt aactggtcga accaaccatg aatgatttgg gcataat              47

<210> SEQ ID NO 192
<211> LENGTH: 47
<212> TYPE: DNA
<213> ORGANISM: Artificial sequence
<220> FEATURE:
<223> OTHER INFORMATION: Primer

<400> SEQUENCE: 192
attatgccca aatcattcat ggttggttcg accagttaag agttaag              47
```

COMPOSITIONS AND METHODS FOR IMPROVED PLANT FEEDSTOCK

This application claims priority to U.S. Provisional Patent Appl. Ser. No. 61/483,460, filed May 6, 2011, the entire disclosure of which is incorporated herein by reference.

GOVERNMENTAL INTEREST

This invention was made with government support under Grant No. DE-AC05-00OR22725 awarded by the U.S. Department of Energy through the BioEnergy Science Center of the Office of Biological and Environmental Research. The government has certain rights in the invention.

FIELD OF THE INVENTION

The present invention relates generally to the field of agriculture and plant genetics. More particularly, it concerns methods and compositions for producing improved feedstocks.

BACKGROUND OF THE INVENTION

Switchgrass is one of the most promising lignocellulosic bioenergy crops for North America owning to its high biomass yield and wide geographic adaptation. However, the major barrier to efficient conversion of its lignocellulose to fuel is the recalcitrant nature of the lignin-enriched cell wall which prevents enzymatic degradation and thereby increases pretreatment costs. Reducing recalcitrance in switchgrass and other biomass crops by manipulating lignin biosynthesis through the expression of key transcription factors is one strategy for increasing biofuel availability.

SUMMARY OF THE INVENTION

In one aspect, the invention provides methods and compositions for improving biofuel feedstock by reducing lignin production through the over-expression of a transcription factor involved in the repression of lignin biosynthetic pathways. In another aspect, the invention provides compositions and methods for modifying MYB4 transcription factor expression to achieve desirable plant phenotypes. In further aspects, the invention provides constructs for over-expressing MYB4 in plants comprising a MYB4 transcription factor sequence as disclosed herein operably linked to a heterologous promoter that directs expression of the nucleotide sequence in a plant cell. MYB4 transcription factor sequences may also be down-regulated in accordance with the invention. Suppression of MYB4 expression may be accomplished by any method known in the art including, for instance via RNAi-mediated suppression, among other approaches. In certain aspects, the plant exhibits a reduced cell wall-bound coumaric acid to ferulic acid ratio. In further aspects, the plant are amenable to processing of sugars from their cell walls. In additional aspects, the plants have a decreased height but increased tillers and have a normal or even enhanced overall biomass.

In one aspect, the invention provides a nucleic acid molecule comprising a nucleic acid sequence selected from the group consisting of (a) a nucleic acid sequence that hybridizes to the sequence of SEQ ID NO:1; SEQ ID NO:7; SEQ ID NO:9; SEQ ID NO:11; SEQ ID NO:13; SEQ ID NO:31; SEQ ID NO:33; SEQ ID NO:37; SEQ ID NO:39; SEQ ID NO:41; SEQ ID NO:43; SEQ ID NO:53; SEQ ID NO:55; SEQ ID NO:59; SEQ ID NO:61; SEQ ID NO:65; SEQ ID NO:75; SEQ ID NO:81; SEQ ID NO:83; SEQ ID NO:89; SEQ ID NO:99; SEQ ID NO:101; SEQ ID NO:107; or SEQ ID NO:109 under conditions of 1×SSC and 65° C.; (b) a nucleic acid comprising the sequence of SEQ ID NO:1; SEQ ID NO:7; SEQ ID NO:9; SEQ ID NO:11; SEQ ID NO:13; SEQ ID NO:31; SEQ ID NO:33; SEQ ID NO:37; SEQ ID NO:39; SEQ ID NO:41; SEQ ID NO:43; SEQ ID NO:53; SEQ ID NO:55; SEQ ID NO:59; SEQ ID NO:61; SEQ ID NO:65; SEQ ID NO:75; SEQ ID NO:81; SEQ ID NO:83; SEQ ID NO:89; SEQ ID NO:99; SEQ ID NO:101; SEQ ID NO:107; or SEQ ID NO:109; (c) a nucleic acid sequence exhibiting at least 85% sequence identity to the nucleic acid sequence of SEQ ID NO:1; SEQ ID NO:7; SEQ ID NO:9; SEQ ID NO:11; SEQ ID NO:13; SEQ ID NO:31; SEQ ID NO:33; SEQ ID NO:37; SEQ ID NO:39; SEQ ID NO:41; SEQ ID NO:43; SEQ ID NO:53; SEQ ID NO:55; SEQ ID NO:59; SEQ ID NO:61; SEQ ID NO:65; SEQ ID NO:75; SEQ ID NO:81; SEQ ID NO:83; SEQ ID NO:89; SEQ ID NO:99; SEQ ID NO:101; SEQ ID NO:107; or SEQ ID NO:109; (d) a nucleic acid sequence that encodes a polypeptide at least 85% identical to the polypeptide sequence of SEQ ID NO:2; SEQ ID NO:8; SEQ ID NO:10; SEQ ID NO:12; SEQ ID NO:14; SEQ ID NO:32; SEQ ID NO:34; SEQ ID NO:38; SEQ ID NO:40; SEQ ID NO:42; SEQ ID NO:44; SEQ ID NO:54; SEQ ID NO:56; SEQ ID NO:60; SEQ ID NO:62; SEQ ID NO:66; SEQ ID NO:76; SEQ ID NO:82; SEQ ID NO:84; SEQ ID NO:90; SEQ ID NO:100; SEQ ID NO:102; SEQ ID NO:108; or SEQ ID NO:110; and (e) a nucleic acid sequence comprising the full complement of (a)-(d).

In another aspect, the invention is a A DNA construct comprising a nucleic acid sequence selected from the group consisting of: (a) a nucleic acid sequence that hybridizes to the sequence of SEQ ID NO:1; SEQ ID NO:7; SEQ ID NO:9; SEQ ID NO:11; SEQ ID NO:13; SEQ ID NO:31; SEQ ID NO:33; SEQ ID NO:37; SEQ ID NO:39; SEQ ID NO:41; SEQ ID NO:43; SEQ ID NO:53; SEQ ID NO:55; SEQ ID NO:59; SEQ ID NO:61; SEQ ID NO:65; SEQ ID NO:75; SEQ ID NO:81; SEQ ID NO:83; SEQ ID NO:89; SEQ ID NO:99; SEQ ID NO:101; SEQ ID NO:107; or SEQ ID NO:109 under conditions of 1×SSC and 65° C.; (b) a nucleic acid comprising the sequence of SEQ ID NO:1; SEQ ID NO:7; SEQ ID NO:9; SEQ ID NO:11; SEQ ID NO:13; SEQ ID NO:31; SEQ ID NO:33; SEQ ID NO:37; SEQ ID NO:39; SEQ ID NO:41; SEQ ID NO:43; SEQ ID NO:53; SEQ ID NO:55; SEQ ID NO:59; SEQ ID NO:61; SEQ ID NO:65; SEQ ID NO:75; SEQ ID NO:81; SEQ ID NO:83; SEQ ID NO:89; SEQ ID NO:99; SEQ ID NO:101; SEQ ID NO:107; or SEQ ID NO:109; (c) a nucleic acid sequence exhibiting at least 85% sequence identity to the nucleic acid sequence of SEQ ID NO:1; SEQ ID NO:7; SEQ ID NO:9; SEQ ID NO:11; SEQ ID NO:13; SEQ ID NO:31; SEQ ID NO:33; SEQ ID NO:37; SEQ ID NO:39; SEQ ID NO:41; SEQ ID NO:43; SEQ ID NO:53; SEQ ID NO:55; SEQ ID NO:59; SEQ ID NO:61; SEQ ID NO:65; SEQ ID NO:75; SEQ ID NO:81; SEQ ID NO:83; SEQ ID NO:89; SEQ ID NO:99; SEQ ID NO:101; SEQ ID NO:107; or SEQ ID NO:109; (d) a nucleic acid sequence that encodes a polypeptide at least 85% identical to the polypeptide sequence of SEQ ID NO:2; SEQ ID NO:8; SEQ ID NO:10; SEQ ID NO:12; SEQ ID NO:14; SEQ ID NO:32; SEQ ID NO:34; SEQ ID NO:38; SEQ ID NO:40; SEQ ID NO:42; SEQ ID NO:44; SEQ ID NO:54; SEQ ID NO:56; SEQ ID NO:60; SEQ ID NO:62; SEQ ID NO:66; SEQ ID NO:76; SEQ ID NO:82; SEQ ID NO:84; SEQ ID NO:90; SEQ ID NO:100; SEQ ID NO:102; SEQ ID NO:108; or SEQ ID NO:110; and (e) a nucleic acid sequence comprising the full complement of (a)-(d), wherein the nucleic acid sequence is operably linked to a heterologous promoter sequence and wherein expression of the nucleic acid sequence in a transgenic plant reduces the lignin content of the plant. In still another aspect, the heterologous promoter sequence is a developmentally-regulated, organelle-specific, inducible, tissue-specific, constitutive, cell-specific, seed specific, or germination-specific promoter. In a further aspect, a plant comprises the above DNA construct.

In another aspect, the plant is forage plant, a biofuel crop, or a cereal crop. In a further aspect, the biofuel crop is switchgrass (Panicum virgatum), giant reed (Arundo donax), reed canarygrass (Phalaris arundinacea), Miscanthus×giganteus, Miscanthus sp., sericea lespedeza (Lespedeza cuneata), corn, sugarcane, sorghum, millet, ryegrass (Lolium multiflorum, Lolium sp.), timothy, Kochia (Kochia scoparia), soybean, alfalfa, clover, sunn hemp, kenaf, bahiagrass, bermudagrass, dallisgrass, pangolagrass, big bluestem, indiangrass, fescue (Festuca sp.), Eremochloa ophiuroides (centipede grass), Dactylis sp., Brachypodium distachyon, smooth bromegrass, orchardgrass, Kentucky bluegrass, poplar, rice, cotton, Salvia miltiorrhiza (red sage), apple, Vitis vinifera (common grape), Ricinus communis (castor oil plant), Humulus lupulus (hops), Dahlia, Dendrobium (orchid), Brassica rapa (mustard), kudzu (Pueraria lobata) or wheat. In a further aspect, the transgenic plant comprising a DNA construct of the invention is an R0 transgenic plant or progeny of any generation of an R0 transgenic plant, wherein the transgenic plant has inherited the DNA construct.

In another aspect, the plant further comprises at least a second nucleic acid sequence that down-regulates lignin biosynthesis, and wherein the sequence down-regulates a lignin biosynthesis gene selected from the group consisting of 4-coumarate 3-hydroxylase (C3H), phenylalanine ammonialyase (PAL), cinnamate 4-hydroxylase (C4H), hydroxycinnamoyl coenzyme A: shikimate hydroxycinnamoyltransferase (HCT), caffeic acid O-methyltransferase (COMT), caffeoyl CoA 3-O-methyltransferase (CCoAOMT), ferulate 5-hydroxylase (F5H), cinnamyl alcohol dehydrogenase (CAD), cinnamoyl CoA-reductase (CCR), and 4-coumarate-CoA ligase (4CL). In another aspect, the transgenic plant of the present invention comprising a second nucleic acid sequence comprises an antisense or RNAi construct.

In yet another aspect, the present invention provides a method of modifying the lignin content of a plant comprising down-regulating or over-expressing in the plant a MYB4 transcription factor that functions to suppress lignin biosynthesis. In certain aspects, the method comprises over-expressing in the plant the MYB4 transcription factor and wherein lignin content is decreased in the plant. In another aspect, the method comprises expressing in the plant a certain DNA construct. In still another aspect, the plant expressing the DNA construct has an increased content of fermentable carbohydrates. In a further aspect, the plant comprises down-regulating the MYB4 transcription factor and increasing lignin. In an additional aspect, down-regulating the MYB4 transcription factor comprises expressing in the plant a RNAi or antisense construct comprising all or a part of the nucleic acid sequence of SEQ ID NO:1; SEQ ID NO:7; SEQ ID NO:9; SEQ ID NO:11; SEQ ID NO:13; SEQ ID NO:31; SEQ ID NO:33; SEQ ID NO:37; SEQ ID NO:39; SEQ ID NO:41; SEQ ID NO:43; SEQ ID NO:53; SEQ ID NO:55; SEQ ID NO:59; SEQ ID NO:61; SEQ ID NO:65; SEQ ID NO:75; SEQ ID NO:81; SEQ ID NO:83; SEQ ID NO:89; SEQ ID NO:99; SEQ ID NO:101; SEQ ID NO:107; or SEQ ID NO:109; wherein the expression of the RNAi or antisense construct down-regulates said MYB4 transcription factor.

Embodiments discussed in the context of methods and/or compositions of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating illustrative embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. Asterisks on tops of the bars of figures indicate values that were determined by the Student's t-test to be significantly different from the wild type or its relevant control ($p<0.05$).

FIGS. 1A-1C illustrate that PvMYB4 belongs to the R2R3-MYB Subfamily 4. (A) ClustalW alignment of the amino acid sequences of PvMYB4 and other R2R3-MYB subfamily 4 proteins. The R2, R3 MYB domains are underlined. The shaded boxes highlight the sequences of the potential functional motifs shown in (B). (B) Structure of PvMYB4 protein domains and motifs. PPI, protein-protein interaction motif for interaction with bHLH protein; C1, C2, Zf and C4, C-terminal motifs. (C) Phylogenetic analysis of PvMYB4 with other subfamily 4 protein sequences by Phylogeny.fr program (worldwideweb.phylogeny.fr/). The dotted boxes indicate dicot and monocot phylogenetic clades. Accession numbers for subgroup 4 sequences: PvMYB4a (JF299185) (SEQ ID NO:2), PvMYB4b (JF299186) (SEQ ID NO:8), PvMYB4c (JF299187) (SEQ ID NO:10), PvMYB4d (JF299188) (SEQ ID NO:12), PvMYB4e (JF299189) (SEQ ID NO:14), AtMYB32 (NM_119665) (SEQ ID NO:16), EgMYB1 (CAE09058) (SEQ ID NO:18), AmMYB308 (JQ0960) (SEQ ID NO:20), AtMYB4 (AY519615) (SEQ ID NO:22), AmMYB330 (JQ0957) (SEQ ID NO:24), ZmMYB42 (CAJ42204) (SEQ ID NO:26) and ZmMYB31 (CAJ42202) (SEQ ID NO:28).

FIGS. 2A-2B present PvMYB4 Gene Variants in Switchgrass. (A) ClustalW alignment of the amino acid sequences of PvMYB4a, 4b, 4c, 4d, and 4e. The box indicates the P-Q-rich region. Accession numbers and SED ID NOs for the sequences in the alignment: PvMYB4a (JF299185) (SEQ ID NO:2), PvMYB4b (JF299186) (SEQ ID NO:8), PvMYB4c (JF299187) (SEQ ID NO:10), PvMYB4d (JF299188) (SEQ ID NO:12), PvMYB4e (JF299189) (SEQ ID NO:14), (B) Different EST clones sequenced. The EST clone MYB_6497_S3 was used for making all the constructs herein.

FIGS. 4A-4G illustrate PvMYB4 binding to AC elements. (A) Synthetic AC I-IV elements (SEQ ID NOs: 3-6) tested in electrophoretic mobility shift assay (EMSA) and yeast assays. (B) Effector and reporter plasmids for testing the binding of PvMYB4 to AC elements in yeast. The transcription factors PtMYB4 and HY5 were used as positive and negative controls, respectively. (C) PtMYB4 can bind to AC elements in yeast to activate the lacZ reporter gene. AC(1, 2, 3, 4)-AD and AC(1, 2, 3, 4)-Pt refer to assays with reporters containing three consecutive copies of the AC I, II, III, or IV elements fused to the pCYC1 minimal promoter and lacZ (as shown in panel B with either GAL4AD or GAL4AD-PtMYB4 as effector). Data are means±SE (n=4). (D) β-Galactosidase assays for lacZ expression driven by PvMYB4 binding to AC elements in yeast. AC(1, 2, 3, 4)-AD, as above. AC(1, 2, 3, 4)-Pv and AC(1, 2, 3, 4)-HY are the reporters containing three consecutive copies of the AC I, II, III, or IV elements fused to the pCYC1 minimal promoter and lacZ with either GAL4AD-PvMYB4 or GAL4AD-HY5 as effectors. Data are means±SE (n=4). (E) EMSAs of PvMYB4 with AC elements. F, free probe; B, shifted band. (F) Effector and reporter constructs for testing the PvMYB4 repression motif in yeast. GBD, GAL4 DNA binding domain; VP16, activation motif of the VP16 protein, GALBs, GAL4 protein binding sites. (G) β-Galactosidase assays showing relative activation of lacZ expression from the reporter 6GALBs-LacZ by the effectors with different PvMYB4 C-terminal deletions (numbers 1 to 8) shown in (F). Data were normalized to the vector control pGBT-9 (GBD), and are means±SE (n=4). Bars with the same letters are not significantly different.

DESCRIPTION OF ILLUSTRATIVE EMBODIMENTS

Figure 1B:
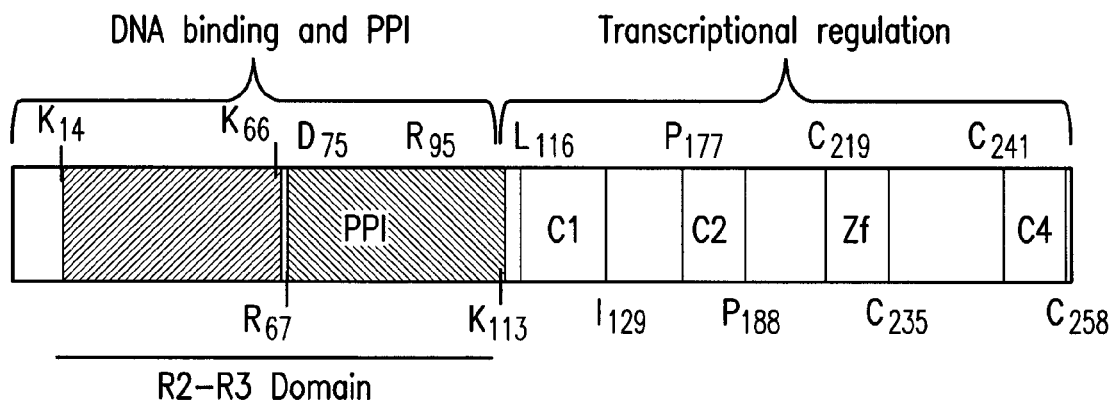

The invention provides methods and compositions for improving biofuel feedstock by reducing lignin production through the over-expression of a transcription factor identified by the inventors as involved in the repression of lignin biosynthetic pathways. It was also surprisingly found by the inventors that plants could be obtained exhibiting reduced cell wall-bound coumaric acid to ferulic acid ratio. Plants produced in accordance with the invention were further found to be more amenable to processing of sugars from their cell walls, which is beneficial for forage digestibility as well as biofuel processing by fermentation. Furthermore, transgenic plants were identified with a decreased height but increased tillers, beneficial for forage use, and some lines were recovered with a normal or even enhanced overall biomass.

The invention therefore provides compositions and methods for modifying MYB4 transcription factor expression to achieve desirable plant phenotypes. This includes constructs for over-expressing MYB4 in plants comprising a MYB4 transcription factor sequence as disclosed herein operably linked to a heterologous promoter that directs expression of the nucleotide sequence in a plant cell.

MYB4 transcription factor sequences may also be down-regulated in accordance with the invention. Suppression of MYB4 expression may be accomplished by any method known in the art including, for instance via RNAi-mediated suppression, among other approaches.

Of particular interest are polynucleotide molecules wherein the polynucleotide molecules encode a polypeptide with MYB4 transcription factor activity, such as the ability to suppress lignin biosynthesis. This includes sequences that comprise, in specific embodiments, at least about 85% sequence identity, at least about 90% sequence identity, at least about 92% sequence identity, at least about 94% sequence identity, or even greater sequence identity, specifically including about 95%, 96%, 97%, 98%, and about 99% or greater sequence identity with any of the nucleic acid sequences disclosed herein, including those of SEQ ID NO:1; SEQ ID NO:7; SEQ ID NO:9; SEQ ID NO:11; SEQ ID NO:13; SEQ ID NO:31; SEQ ID NO:33; SEQ ID NO:37; SEQ ID NO:39; SEQ ID NO:41; SEQ ID NO:43; SEQ ID NO:53; SEQ ID NO:55; SEQ ID NO:59; SEQ ID NO:61; SEQ ID NO:65; SEQ ID NO:75; SEQ ID NO:81; SEQ ID NO:83; SEQ ID NO:89; SEQ ID NO:99; SEQ ID NO:101; SEQ ID NO:107; and SEQ ID NO:109.

The invention further provides polypeptide sequences, and the nucleic acids that encode them, wherein the polypeptide comprises at least about 85% sequence identity, at least about 90% sequence identity, at least about 92% sequence identity, at least about 94% sequence identity, or even greater sequence identity, specifically including about 95%, 96%, 97%, 98%, and about 99% or greater sequence identity with any of the polypeptide sequences disclosed herein, including those of SEQ ID NO:2; SEQ ID NO:8; SEQ ID NO:10; SEQ ID NO:12; SEQ ID NO:14; SEQ ID NO:32; SEQ ID NO:34; SEQ ID NO:38; SEQ ID NO:40; SEQ ID NO:42; SEQ ID NO:44; SEQ ID NO:54; SEQ ID NO:56; SEQ ID NO:60; SEQ ID NO:62; SEQ ID NO:66; SEQ ID NO:76; SEQ ID NO:82; SEQ ID NO:84; SEQ ID NO:90; SEQ ID NO:100; SEQ ID NO:102; SEQ ID NO:108; or SEQ ID NO:110. In particular embodiments, the polypeptide is defined as comprising MYB4 transcription factor activity.

In certain embodiments of the invention, nucleic acids hybridizing to the disclosed sequences or a complement or reverse complement thereof, under stringent conditions, are provided. Such stringent conditions are well known in the art and include 5×.SSC, 50% formamide and 42° C., or 1× (or less) SSC and 65° C. The invention further provides nucleic acid sequences that encode a sequence complementary to all or a part of an mRNA encoded by a MYB4 transcription factor sequence provided herein, as described herein and known in the art, wherein the expression of the sequences functions to down-regulate MYB4. In certain embodiments of the invention, fragments or complements thereof of at least 21 contiguous nucleotides of a nucleic acid sequence disclosed herein are provided.

I. PRODUCTION OF ETHANOL FROM LIGNOCELLULOSIC BIOMASS

The overall process for the production of ethanol from biomass typically involves two steps: saccharification and fermentation. First, saccharification produces fermentable sugars from the cellulose and hemicellulose in the lignocellulosic biomass. Second, those sugars are then fermented to produce ethanol. Additional methods and protocols for the production of ethanol from biomass are known in the art and reviewed in, for example, Wyman (1999); Gong et al., (1999); Sun and Cheng, (2002); and Olsson and Hahn-Hagerdal (1996).

A. Pretreatment

Raw biomass is typically pretreated to increase porosity, hydrolyze hemicellulose, remove lignin and reduce cellulose crystallinity, all in order to improve recovery of fermentable sugars from the cellulose polymer. As a preliminary step in pretreatment, the lignocellulosic material may be chipped or ground. The size of the biomass particles after chipping or grinding is typically between 0.2 and 30 mm. After chipping a number of other pretreatment options may be used to further prepare the biomass for saccharification and fermentation, including steam explosion, ammonia fiber explosion, acid hydrolysis.

1. Steam Explosion

Steam explosion is a very common method for pretreatment of lignocellulosic biomass and increases the amount of cellulose available for enzymatic hydrolysis (U.S. Pat. No. 4,461,648). Generally, the material is treated with high-pressure saturated steam and the pressure is rapidly reduced, causing the materials to undergo an explosive decompression. Steam explosion is typically initiated at a temperature of 160-260° C. for several seconds to several minutes at pressures of up to 4.5 to 5 MPa. The biomass is then exposed to atmospheric pressure. The process causes hemicellulose degradation and lignin transformation. Addition of $H_2SO_4$, $SO_2$, or $CO_2$ to the steam explosion reaction can improve subsequent cellulose hydrolysis, decrease production of inhibitory compounds and lead to the more complete removal of hemicellulose (Morjanoff and Gray, 1987).

2. Ammonia Fiber Explosion (AFEX)

In AFEX pretreatment, the biomass is treated with approximately 1-2 kg ammonia per kg dry biomass for approximately 30 minutes at pressures of 1.5 to 2 MPa. (U.S. Pat. No. 4,600,590; U.S. Pat. No. 5,037,663; Mes-Hartree, et al., 1988). Like steam explosion, the pressure is then rapidly reduced to atmospheric levels, boiling the ammonia and exploding the lignocellulosic material. AFEX pretreatment appears to be especially effective for biomass with a relatively low lignin content, but not for biomass with high lignin content such as newspaper or aspen chips (Sun and Cheng, 2002).

3. Acid Hydrolysis

Concentrated or dilute acids may also be used for pretreatment of lignocellulosic biomass. $H_2SO_4$ and HCl have been used at high, >70%, concentrations. In addition to pretreatment, concentrated acid may also be used for hydrolysis of cellulose (U.S. Pat. No. 5,972,118). Dilute acids can be used at either high (>160° C.) or low (<160° C.) temperatures, although high temperature may be beneficial for cellulose hydrolysis (Sun and Cheng, 2002). $H_2SO_4$ and HCl at concentrations of 0.3 to 2% (w/w) and treatment times ranging from minutes to 2 hours or longer can be used for dilute acid pretreatment.

Other pretreatments include alkaline hydrolysis, oxidative delignification, organosolv process, or biological pretreatment; see Sun and Cheng (2002).

B. Saccharification

After pretreatment, the cellulose in the lignocellulosic biomass may be hydrolyzed with cellulase enzymes. Cellulase catalyzes the breakdown of cellulose to release glucose which can then be fermented into ethanol.

Bacteria and fungi produce cellulases suitable for use in ethanol production (Duff and Murray, 1995). For example, *Cellulomonas fimi* and *Thermomonospora fusca* have been extensively studied for cellulase production. Among fungi, members of the *Trichoderma* genus, and in particular *Trichoderma reesi*, have been the most extensively studied. Numerous cellulases are available from commercial sources as well. Cellulases are usually actually a mixture of several different specific activities. First, endoglucanases create free chain ends of the cellulose fiber. Exoglucanases remove cellobiose units from the free chain ends and beta-glucosidase hydrolyzes cellobiose to produce free glucose.

Reaction conditions for enzymatic hydrolysis are typically around pH 4.8 at a temperature between 45 and 50° C. with incubations of between 10 and 120 hours. Cellulase loading can vary from around 5 to 35 filter paper units (FPU) of activity per gram of substrate Surfactants like Tween 20, 80, polyoxyethylene glycol or Tween 81 may also be used during enzyme hydrolysis to improve cellulose conversion. Additionally, combinations or mixtures of available cellulases and other enzymes may also lead to increased saccharification.

Aside from enzymatic hydrolysis, cellulose may also be hydrolyzed with weak acids or hydrochloric acid (Lee et al., 1999).

C. Fermentation

Once fermentable sugars have been produced from the lignocellulosic biomass, those sugars may be used to produce ethanol via fermentation. Fermentation processes for producing ethanol from lignocellulosic biomass are extensively reviewed in Olsson and Hahn-Hagerdal (1996). Briefly, for maximum efficiencies, both pentose sugars from the hemicellulose fraction of the lignocellulosic material (e.g., xylose) and hexose sugars from the cellulose fraction (e.g., glucose) should be utilized. *Saccharomyces cerevisiae* are widely used for fermentation of hexose sugars. Pentose sugars, released from the hemicellulose portion of the biomass, may be fermented using genetically engineered bacteria, including *Escherichia coli* (U.S. Pat. No. 5,000,000) or *Zymomonas mobilis* (Zhang et al., 1995). Fermentation with yeast strains is typically optimal around temperatures of 30 to 37° C.

D. Simultaneous Saccharification and Fermentation (SSF)

Cellulase activity is inhibited by its end products, cellobiose and glucose. Consequently, as saccharification proceeds, the build up of those end products increasingly inhibits continued hydrolysis of the cellulose substrate. Thus, the fermentation of sugars as they are produced in the saccharification process leads to improved efficiencies for cellulose utilization (e.g., U.S. Pat. No. 3,990,944). This process is known as simultaneous saccharification and fermentation (SSF), and is an alternative to the above described separate saccharification and fermentation steps. In addition to increased cellulose utilization, SSF also eliminates the need for a separate vessel and processing step. The optimal temperature for SSF is around 38° C., which is a compromise between the optimal temperatures of cellulose hydrolysis and sugar fermentation. SSF reactions can proceed up to 5 to 7 days.

E. Distillation

The final step for production of ethanol is distillation. The fermentation or SSF product is distilled using conventional methods producing ethanol, for instance 95% ethanol.

II. PLANT TRANSFORMATION CONSTRUCTS

In a certain embodiment DNA constructs for plant transformation are provided. Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton et al. (1996).

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Components that may be included with vectors used in the current invention are as follows.

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), α-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters.

The DNA sequence between the transcription initiation site and the start of the coding sequence, i.e., the untranslated leader sequence, can also influence gene expression. One may thus wish to employ a particular leader sequence with a transformation construct of the invention. Leader sequences are contemplated to include those which comprise sequences predicted to direct optimum expression of the attached gene, i.e., to include a consensus leader sequence which may increase or maintain mRNA stability and prevent inappropriate initiation of translation. The choice of such sequences will be known to those of skill in the art in light of the present disclosure. Sequences that are derived from genes that are highly expressed in plants may be beneficial in particular embodiments.

It is contemplated that vectors for use in accordance with the present invention may be constructed to include an ocs enhancer element. This element was first identified as a 16 bp palindromic enhancer from the octopine synthase (ocs) gene of *Agrobacterium* (Ellis et al., 1987), and is present in at least 10 other promoters (Bouchez et al., 1989). The use of an enhancer element, such as the ocs element and particularly multiple copies of the element, may act to increase the level of transcription from adjacent promoters when applied in the context of plant transformation.

It is envisioned that MYB4 coding sequences (or complements thereof) may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue.

Transformation constructs prepared in accordance with the invention will typically include a 3' end DNA sequence that acts as a signal to terminate transcription and allow for the poly-adenylation of the mRNA produced by coding sequences operably linked to a promoter. It is envisioned that the native terminator of a MYB4 coding sequence may be used. Alternatively, a heterologous 3' end may enhance the expression of sense or antisense MYB4 coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces* viridochromogenes. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228). The gene that encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

III. ANTISENSE AND RNAi CONSTRUCTS

Antisense and RNAi treatments represent one way of reducing MYB4 transcription factor expression in accordance with the invention. Techniques for RNAi are well known in the art and are described in, for example, Lehner et al., (2004) and Downward (2004). The technique is based on the fact that double stranded RNA is capable of directing the degradation of messenger RNA with sequence complementary to one or the other strand (Fire et al., 1998). Therefore, by expression of a particular coding sequence in sense and antisense orientation, either as a fragment or longer portion of the corresponding coding sequence, the expression of that coding sequence can be down-regulated.

Antisense, and in some aspects RNAi, methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense and RNAi constructs, or DNA encoding such RNA's, may be employed to inhibit gene transcription or translation or both within a host cell, either in vitro or in vivo, such as within a host plant cell. In certain embodiments of the invention, such an oligonucleotide may comprise any unique portion of a nucleic acid sequence provided herein. In certain embodiments of the invention, such a sequence comprises at least 17, 18, 19, 20, 21, 25, 30, 50, 75 or 100 or more contiguous nucleic acids of the nucleic acid sequence of any of the MYB4 transcription factor sequences provided herein, and/or complements thereof, which may be in sense and/or antisense orientation. By including sequences in both sense and antisense orientation, increased suppression of the corresponding coding sequence may be achieved.

Constructs may be designed that are complementary to all or part of the promoter and other control regions, exons, introns or even exon-intron boundaries of a gene. It is contemplated that the most effective constructs may include regions complementary to intron/exon splice junctions. Thus, it is proposed that one embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an RNAi or antisense construct which has limited regions of high homology, but also contains a non-homologous region (e.g., ribozyme; see above) could be designed. Methods for selection and design of sequences that generate RNAi are well known in the art (e.g., Reynolds, 2004). These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence. Constructs useful for generating RNAi may also comprise concatemers of sub-sequences that display gene regulating activity.

IV. METHODS FOR GENETIC TRANSFORMATION

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species, including biofuel crop species, may be stably transformed, and these cells developed into transgenic plants.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is often the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

Similarly, *Agrobacterium* mediated transformation has also proven to be effective in switchgrass. Somleva et al., (2002) describe the creation of approximately 600 transgenic switchgrass plants carrying a bar gene and a uidA gene (beta-glucuronidase) under control of a maize ubiquitin promoter and rice actin promoter respectively. Both genes were expressed in the primary transformants and could be inherited and expressed in subsequent generations. Addition of 50 to 200 µM acetosyringone to the inoculation medium increased the frequency of transgenic switchgrass plants recovered.

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Another method for delivering transforming DNA segments to plant cells is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and gold. For the bombardment, cells in suspension can be concentrated on filters or solid culture medium. Alternatively, immature embryos or other target cells may be arranged on solid culture medium. The cells to be bombarded are positioned at an appropriate distance below a macroprojectile stopping plate.

Examples of species for which have been transformed by microprojectile bombardment include monocot species such as maize (PCT Application WO 95/06128), barley (Ritala et al., 1994; Hensgens et al., 1993), wheat (U.S. Pat. No. 5,563, 055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al., 1994), peanut (Singsit et al., 1997), cotton (McCabe and Martinell, 1993), tomato (VanEck et al., 1995), and legumes in general (U.S. Pat. No. 5,563,055, specifically incorporated herein by reference in its entirety).

Richards et al., (2001) describe the creation of transgenic switchgrass plants using particle bombardment. Callus was bombarded with a plasmid carrying a sgfp (green fluorescent protein) gene and a bar (bialaphos and Basta tolerance) gene under control of a rice actin promoter and maize ubiquitin promoter respectively. Plants regenerated from bombarded callus were Basta tolerant and expressed GFP. These primary transformants were then crossed with non-transgenic control plants, and Basta tolerance was observed in progeny plants, demonstrating inheritance of the bar gene.

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. BACTOAGAR, GELRITE, and GELGRO are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al., (1975) and MS media (Murashige and Skoog, 1962).

V. PRODUCTION AND CHARACTERIZATION OF STABLY TRANSFORMED PLANTS

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

Another example of a herbicide which is useful for selection of transformed cell lines is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. Many other selectable markers are well known and may also be used.

Screenable markers are also well known. An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soiless plant growth mix, and hardened, e.g., in an environmentally controlled chamber, for example, at about 85% relative humidity, 600 ppm $CO_2$, and 25-250 microeinsteins $m^2$/s of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with 10-5M abscisic acid and then transferred to growth regulator-free medium for germination.

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

Frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes. Morphological changes may include a change in stature or thicker stalks. Most often changes in response of plants or plant parts to imposed treatments are evaluated under carefully controlled conditions termed bioassays.

VI. BREEDING PLANTS OF THE INVENTION

In addition to direct transformation of a particular plant genotype with a construct prepared according to the current invention, transgenic plants may be made by crossing a plant having a selected DNA of the invention to a second plant lacking the construct. For example, a transgenic event can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants.

As used herein the term "progeny" denotes the offspring of any generation of a parent plant prepared in accordance with the instant invention, wherein the progeny comprises a selected DNA construct. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:
  (a) plant seeds of the first (starting line) and second (donor plant line that comprises a transgene of the invention) parent plants;
  (b) grow the seeds of the first and second parent plants into plants that bear flowers;
  (c) pollinate a flower from the first parent plant with pollen from the second parent plant; and
  (d) harvest seeds produced on the parent plant bearing the fertilized flower.

Backcrossing is herein defined as the process including the steps of:
  (a) crossing a plant of a first genotype containing a desired gene, DNA sequence or element to a plant of a second genotype lacking the desired gene, DNA sequence or element;
  (b) selecting one or more progeny plant containing the desired gene, DNA sequence or element;
  (c) crossing the progeny plant to a plant of the second genotype; and
  (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VII. DEFINITIONS

Biofuel crop species: A plant that may be used to provide biomass for production of lignocellulosic-derived ethanol.

Examples of such plants include switchgrass (*Panicum virgatum*), giant reed (*Arundo donax*), reed canarygrass (*Phalaris arundinacea*), Miscanthus×giganteus, Miscanthus sp., sericea lespedeza (*Lespedeza cuneata*), corn, sugarcane, sorghum, millet, ryegrass (*Lolium multiflorum, Lolium* sp.), timothy, Kochia (*Kochia scoparia*), forage soybeans, alfalfa, clover and other legumes, sunn hemp, kenaf, bahiagrass, bermudagrass, dallisgrass, pangolagrass, big bluestem, indiangrass, fescue (*Festuca* sp.), *Dactylis* sp., *Brachypodium distachyon*, smooth bromegrass, orchardgrass, Kentucky bluegrass, poplar, willow, and agave, among others, as well as other crops such as wheat, rice, and grapes.

Expression: The combination of intracellular processes, including transcription and translation undergone by a coding DNA molecule such as a structural gene to produce a polypeptide.

Forage crops: Crops including grasses and legumes used as fodder or silage for livestock production.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an R0 transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

R0 transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Transformation constructs generally comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VIII. EXAMPLES

The following examples are included to demonstrate illustrative embodiments of the invention. It should be appreciated by those of skill in the art that the techniques disclosed in the examples which follow represent techniques discovered by the inventor to function well in the practice of the invention, and thus can be considered to constitute one embodiment of modes for its practice. However, those of skill in the art should, in light of the present disclosure, appreciate that many changes can be made in the specific embodiments which are disclosed and still obtain a like or similar result without departing from the spirit and scope of the invention.

Example 1

Switchgrass PvMYB4 Belongs to the R2-R3MYB Subfamily 4

To clone orthologs of the MYB subfamily 4 genes in switchgrass, an AtMYB4 (SEQ ID NO:22) amino acid sequence was used to blast against the switchgrass EST database (Tobias et al., 2005). The ORF of the most homologous gene sequence from switchgrass (cv Alamo) was cloned into the pENTR_D topo vector using RT-PCR. An 836 bp full length cDNA was obtained. The sequence alignment of PvMYB4 with other MYB subfamily 4 members shows that PvMYB4 has a highly conserved R2-R3 domain at the N-terminal region, while the C-terminal domain is more divergent, both in sequence and length (FIG. 1A). However, three typical protein motifs of the MYB subgroup 4 were identified at the C-terminal: "LlsrGIDPxT/SHRxI/L", "pdLNLD/ELxiG/S" and "$CX_{1-2}CX_{7-12}CX_2C$" (Stracke et al., 2001; Fornalé et al., 2006). A "$FLGLX_{4-7}V/LLD/GF/YR/SX_1LEMK$" motif was identified using the ClustalW sequence alignment tool (worldwideweb.ebi.ac.uk/Tools/msa/clustalw2/) (FIG. 1A). The above motifs are termed the C1, C2, Zf and C4 motifs, respectively (FIG. 1B).

Figure 1C:
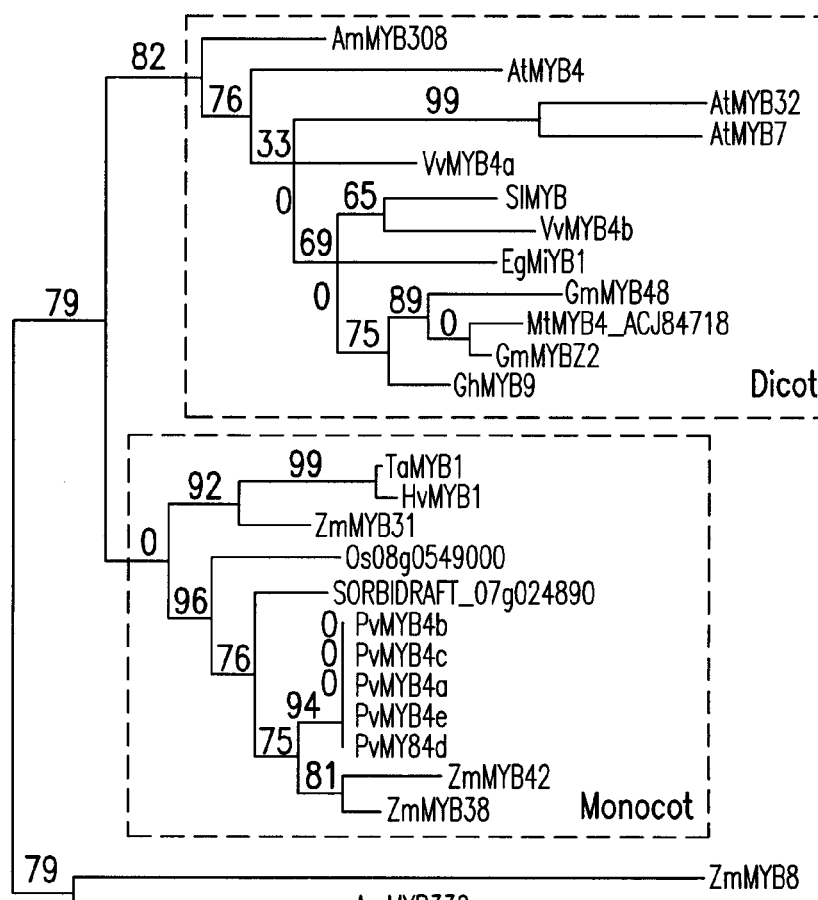

A phylogenetic analysis was performed using the PhyML method and tools available at Phylogeny.fr: worldwideweb.phylogeny.fr to identify the most closely related R2R3-MYB factors within the subfamily 4 group (Dereeper et al., 2008). Most of the dicot and monocot R2R3-MYB subfamily 4 proteins are grouped into separate clades (FIG. 1C). This suggests that the R2R3-MYB subfamily 4 proteins might have divergent biological functions in dicot and monocot plants. Phylogenetic analysis also shows that PvMYB4 is more closely related to ZmMYB42, ZmMYB38 and ZmMYB31 than to the other well-known phenylpropanoid/lignin biosynthesis repressors such as AmMYB308, AtMYB4, and AtMYB32.

Sequencing of the PvMYB4 clones indicated the presence of at least five gene variants of PvMYB4, namely PvMYB4a (SEQ ID NO:1), 4b (SEQ ID NO:7), 4c (SEQ ID NO:9), 4d (SEQ ID NO:11) and 4e (SEQ ID NO:13), in the tetraploid outcrossing switchgrass genome (FIGS. 2A, B). A similar phenomenon has been reported for the switchgrass lignin biosynthesis gene PvCCR1 (Escamilla-Trevino et al., 2009). All constructs were made based on the PvMYB4a sequence.

Example 2

Figure 3A:
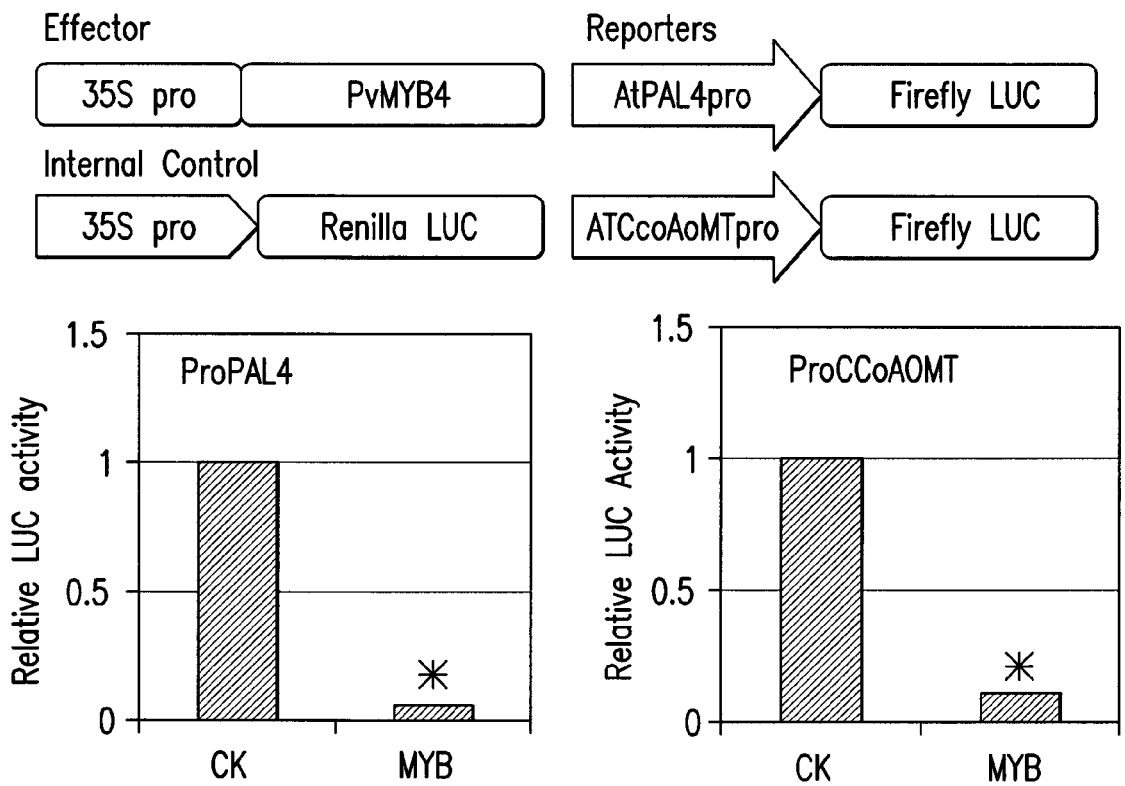
FIGS. 3A-3D show expression patterns and transcriptional repression activity of PvMYB4. (A) Dual luciferase assay of 35S:PvMYB4 effector with firefly luciferase reporter constructs in Arabidopsis protoplasts. CK, vector control used as effector. (B) qRT-PCR analysis of tissue expression pattern of PvMYB4 in switchgrass. Bars with the same letters are not significantly different. (C) in-situ hybridization of PvMYB4 in young stem sections. VT, vascular tissue; P, parenchyma, E, epidermis. Bar=500 μm. Red boxes indicate the vascular bundle areas shown in both upper and lower panels. (D) Confocal images of nuclear localization of PvMYB:eGFP protein in tobacco epidermal cells. Top panel, lower magnification (20× objective lens), bar=50 μm; bottom panel, higher magnification (63× water immersion objective lens), bar=10 μm.

PvMYB4 is a Transcriptional Repressor and is Expressed in the Vascular Bundles of Switchgrass Transcriptional repression activity was analyzed using a dual Luciferase reporter assay in *Arabidopsis* protoplasts. When PvMYB4a (SEQ ID NO:1) was co-expressed with the *Arabidopsis* PALO or CCoAOMT (caffeoyl CoA 3-O-methyltransferase) promoters driving a Luciferase reporter gene, Luciferase expression was repressed by almost 80-90% compared to the values obtained from these lignin pathway promoters in the absence of PvMYB4 expression (FIG. 3A).

Figure 3B:
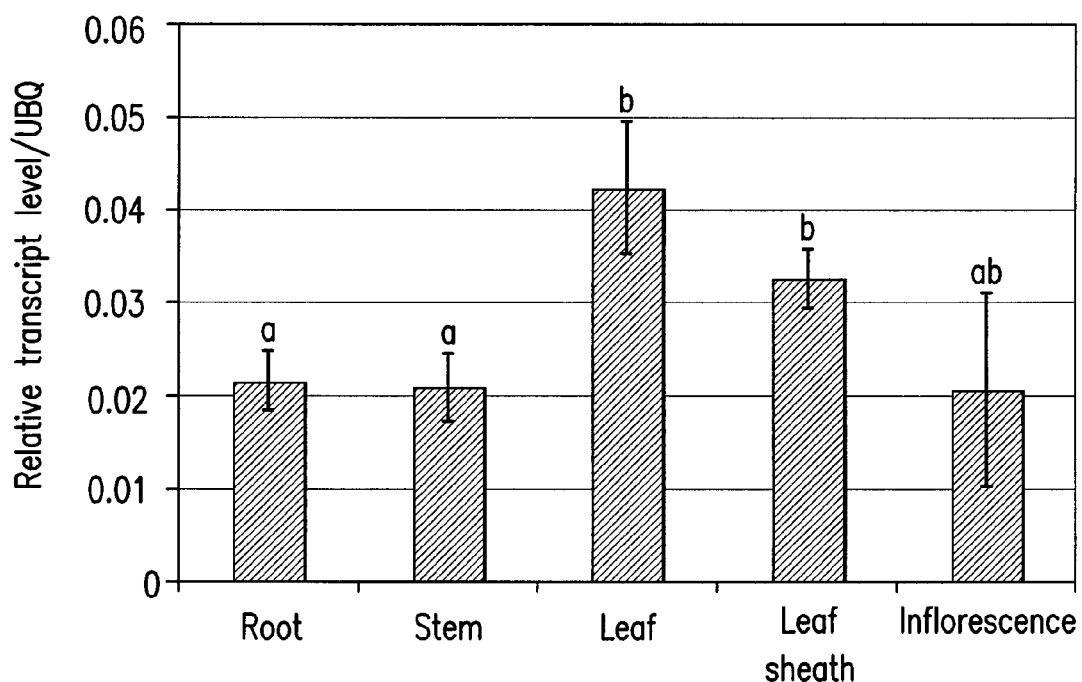
Figure 3C:
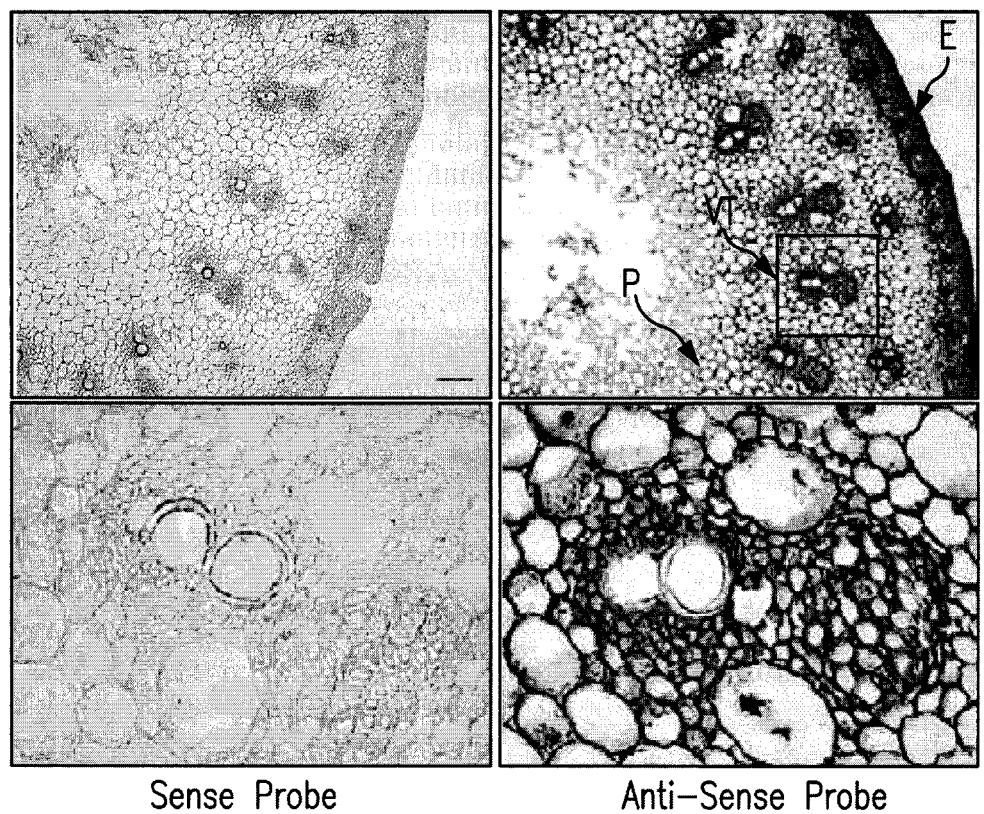
Figure 3D:
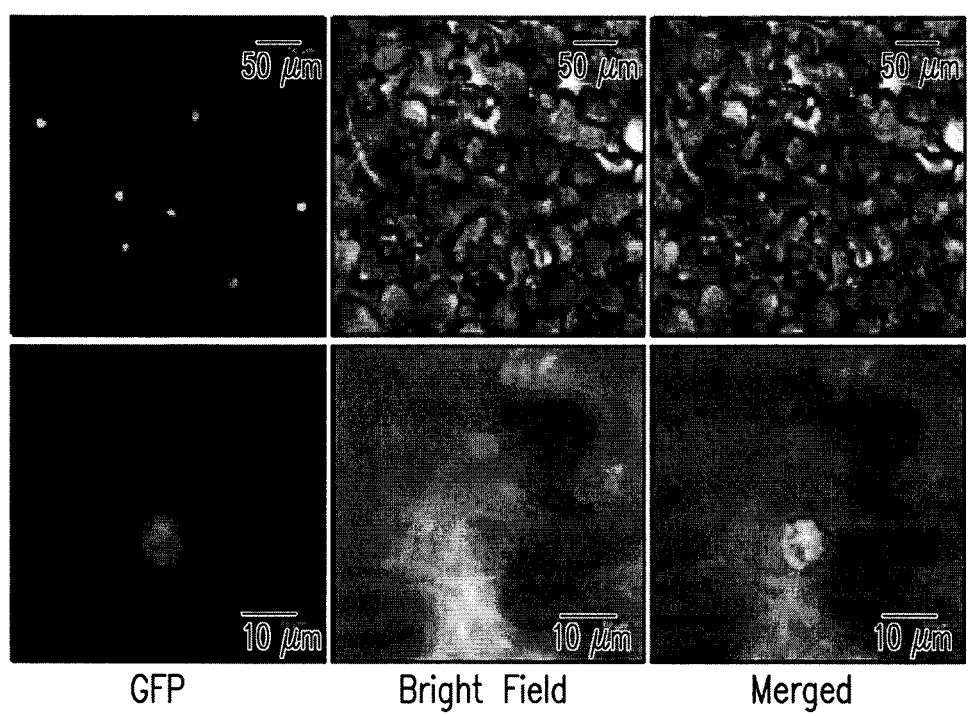

To test the tissue-specific expression pattern of PvMYB4 in switchgrass, total RNA was isolated from different tissues at the R1 developmental stage and qRT-PCR analysis was performed (Moore et al., 1991; Sarath et al., 2007). The PvMYB4 gene was expressed in all the tissues tested, with highest expression in leaf and leaf sheath (FIG. 3B). In-situ hybridization analysis of young stem tissue sections indicated that PvMYB4 is expressed throughout the stem, including the parenchyma cells, vascular tissues and epidermis. The highest expression level appeared to be in vascular bundles (FIG. 3C). To test whether PvMYB4 is localized to the nucleus, infiltration assays were performed of tobacco epidermal cells with a construct for expression of a PvMYB4: eGFP fusion protein. GFP fluorescence was shown to localize to the nucleus by confocal microscopy (FIG. 3D).

Example 3

The PvMYB4 Protein Binds to the AC Elements in the Genes Involved in the Lignin Biosynthesis Pathway Several R2-R3 MYB proteins from subfamily 4 have been reported to bind the AC elements in monolignol pathway gene promoters (Romero et al., 1998; Legay et al., 2007; Zhao et al., 2007). Use of electrophoretic mobility shift assay (EMSA) led to the conclusion that these proteins might bind to "GKTWGGTR" elements in vitro (Romero et al., 1998). The reverse complement sequence of "GKTWGGTR" is "YACCWAMC" with Y as T or C, W as T or A, and M as A or C. The possible elements can therefore be designated as "T/CACCT/AA/CC". AtMYB4 can bind to the AC-I (ACCTACC; SEQ ID NO:3, AC-II (ACCAACC; SEQ ID NO:4) and AC-III (ACCTAAC; SEQ ID NO:5) elements (Zhao et al., 2007). It also binds to the "ACCGCCC" elements (MYB elements) found in its own promoter region (Zhao et al., 2007). EgMYB1 binds to a region of the promoter of the EgCAD (cinnamyl alcohol dehydrogenase) gene containing both the "ACCCACC" and "ACCTACC" elements (AC-I) (Legay et al., 2007).

Figure 4C:
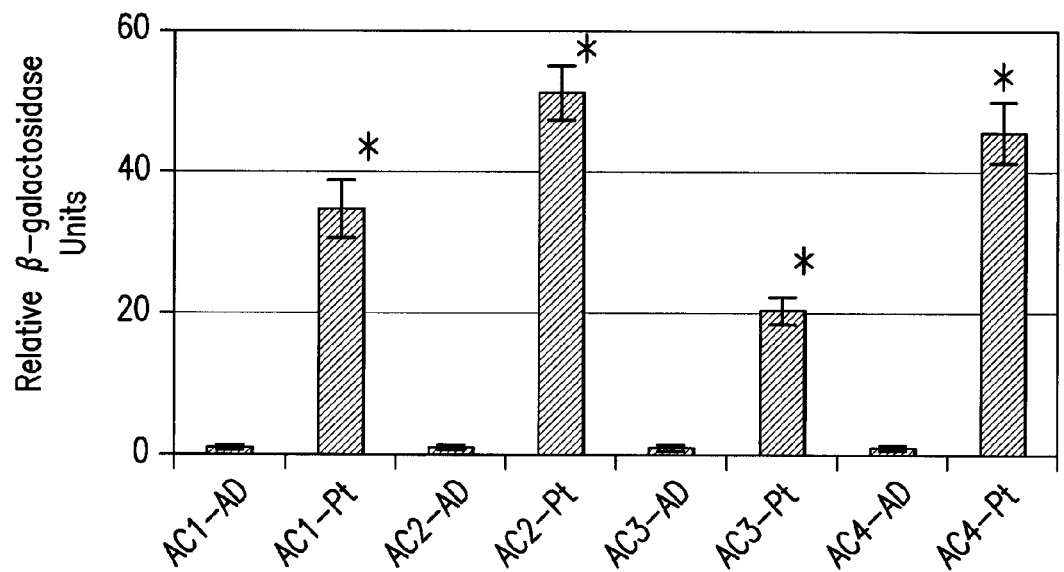
Figure 4D:
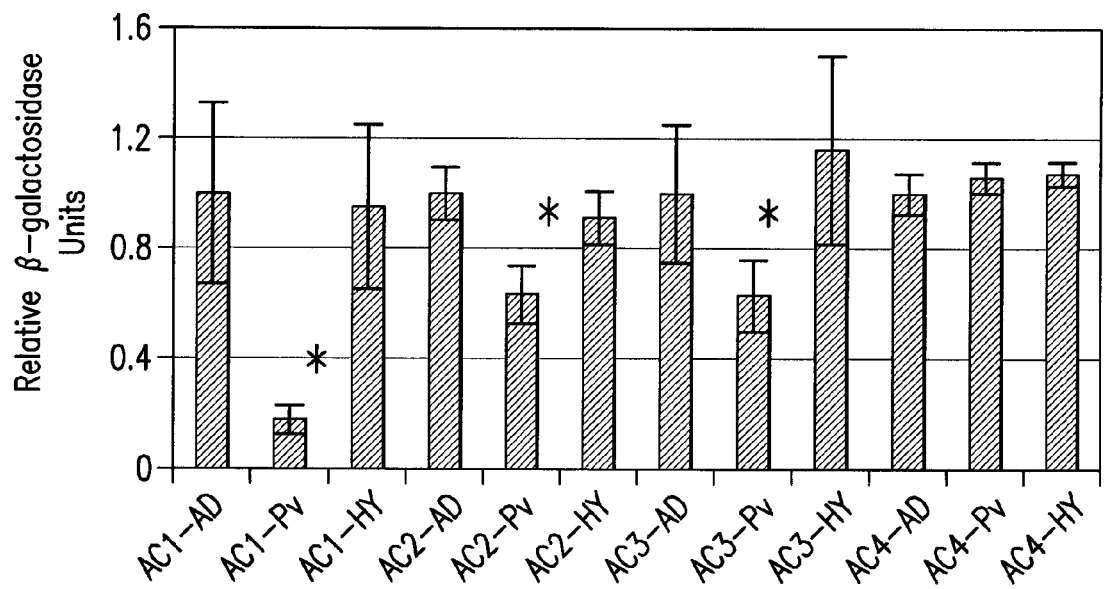
Figure 4E:
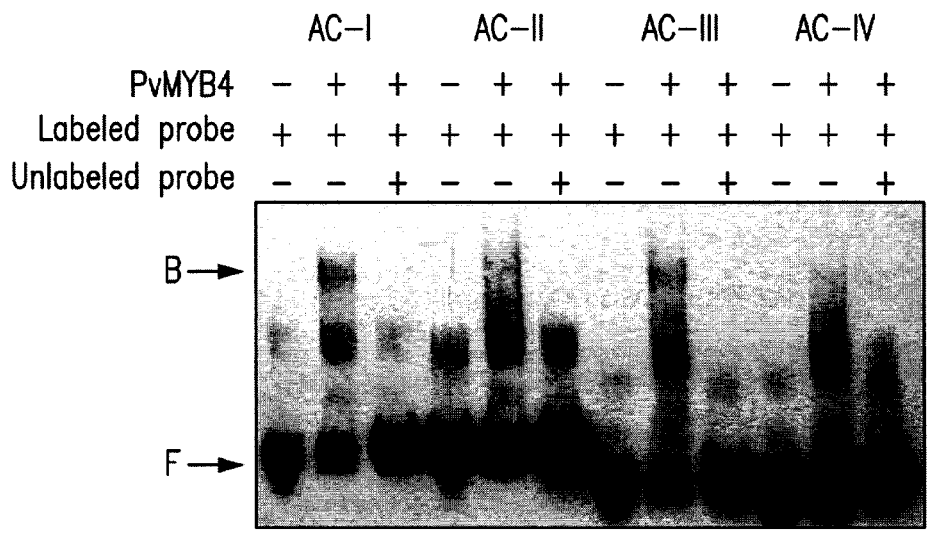

To test whether PvMYB4 can bind to similar AC-rich elements, three repeats of the AC-I, AC-II, AC-III, and AC-IV (ACCAAAC; SEQ ID NO:6) elements (FIG. 4A) were cloned into the pLACZi vector immediately upstream of a pCYC1 minimal promoter driving the LacZ reporter gene, for expression in yeast (FIG. 4B). Since PvMYB4 has transcriptional repression activity, PvMYB4 as a fusion with the GAL4 activation domain (AD) was cloned to generate a chimeric effector (FIG. 4B). If PvMYB4 binds to the test AC-rich elements, it will block the expression of the LacZ reporter gene activated by the GAL4 AD. A R2R3-MYB transcriptional activator PtMYB4 (Bomal et al., 2008) and a bZip transcription factor HY5 (ELONGATED HYPOCOTYL 5) (Oyama et al., 1997) were used as positive and negative controls, respectively, along with the vector control containing only the GAL4-AD (FIG. 4B). The positive control PtMYB4 activated the lacz reporter gene expression by about 50-100 fold compared to the vector and negative controls, indicating that the system is functional in yeast (FIG. 4C). In contrast, PvMYB4 repressed the expression from the three AC-I, 3AC-II and 3AC-III elements fused to the Mini-pCyC1 promoter driving the lacZ reporter gene by about 50-80% compared to the vector and negative control (HY5) under the same conditions (FIG. 4D). However, PvMYB4 did not repress transcription driven by the three AC-IV elements in yeast (FIG. 4D), suggesting that it may not bind to the AC-IV element. PvMYB4 was cloned into the pDEST17 vector with a His tag fusion at the N-terminal, and the purified protein from *E. coli* extracts shown to bind to the AC-I, AC-II and AC-III elements in EMSA assays. No binding affinity of PvMYB4 to AC-IV was observed under the same conditions, which is consistent with the repression activity assay in yeast (FIG. 4E).

Figure 4F:
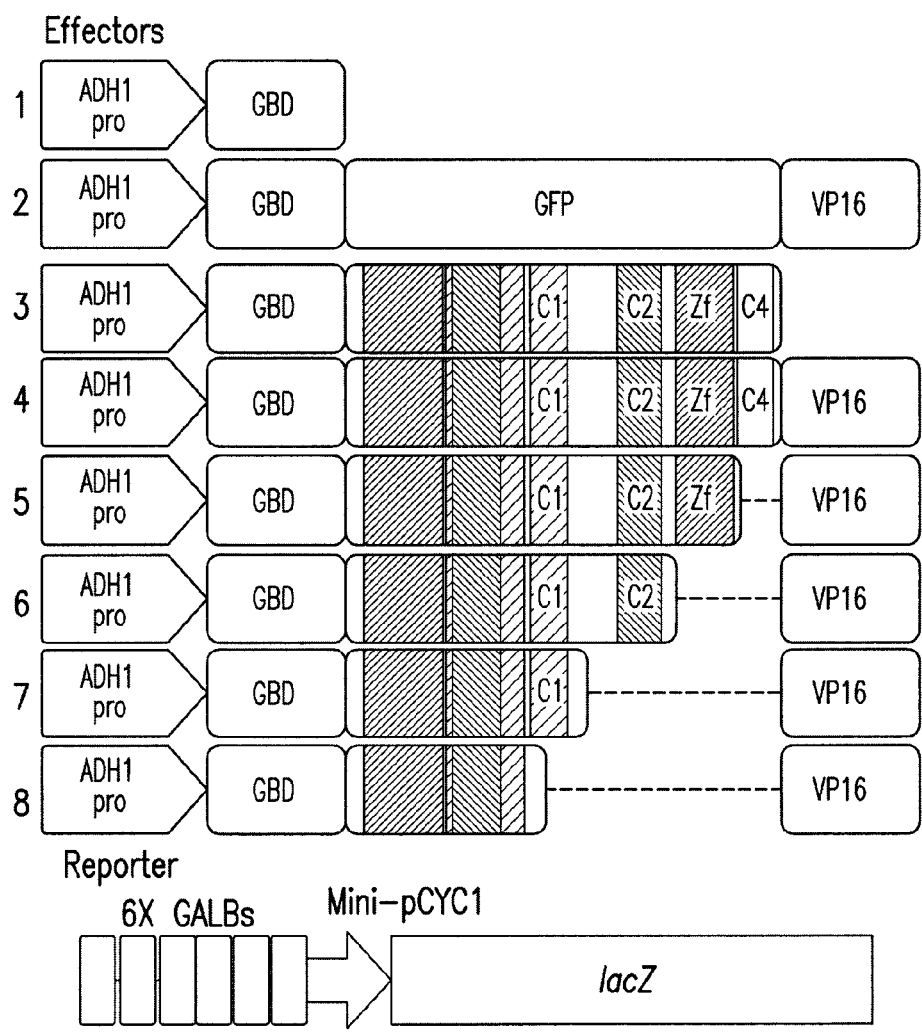
Figure 4G:
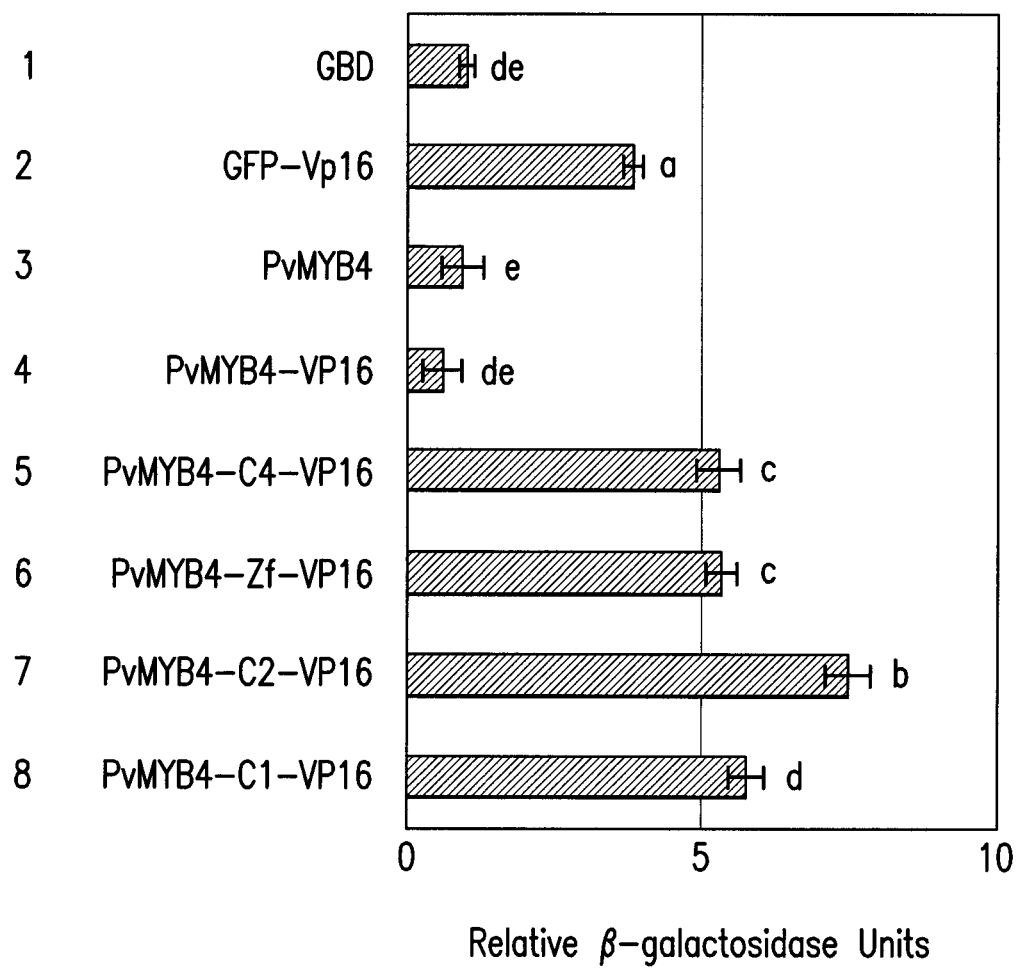

To investigate the functions of the C-terminal motifs in PvMYB4 in more detail, different deletions of PvMYB4 were fused between the VP16 activation motif from herpes simplex virus protein VP16 (Sadowski et al., 1988) and the GAL4 AD (FIG. 4F). The reporter construct was made by placing six GAL4-binding motifs in front of the pCYC1 minimal promoter driving the LacZ reporter gene. After expression of reporter and effector constructs in yeast, β-galactosidase assays indicated that the C1, C2, and C4 motifs all have transcriptional repression activities because the deletion of these motifs restored the transcriptional activation effects contributed to PvMYB4 by the VP16 activation motif. In contrast, the Zf motif (FIG. 1B) did not appear to have significant repression activity (FIG. 4G).

Figures 5A, 5B:
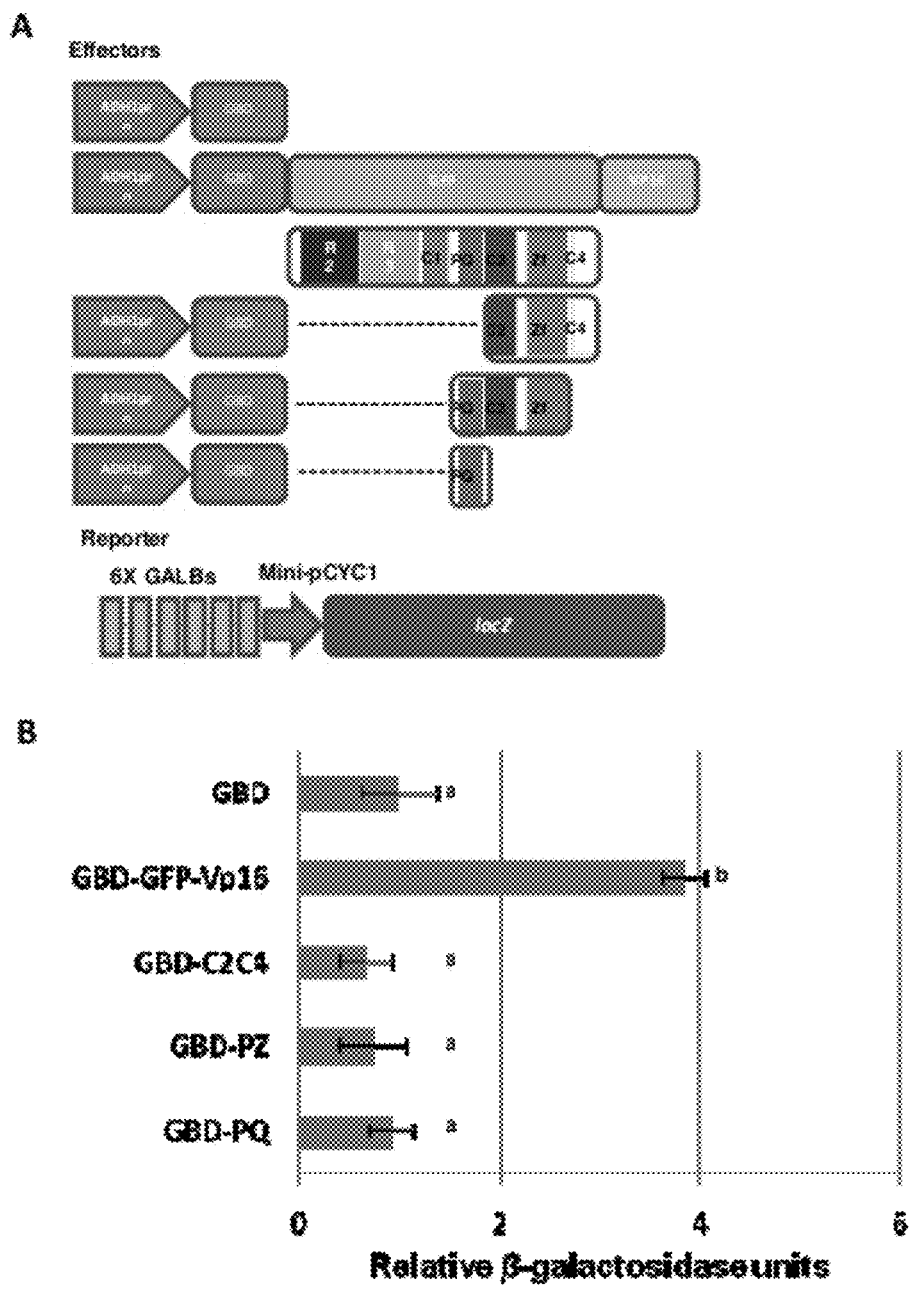
FIGS. 5A-5B illustrate that the PQ-rich motif does not possess transcriptional activation activity. (A) Effectors and reporter constructs for testing the PQ-rich motif in yeast. GBD, GAL4 DNA binding domain; VP16, activation motif of the VP16 protein; GALBs, GAL4 protein binding sites. (B) β-Galactosidase assays showing activation of lacZ expression from the reporter 6GALBs-LacZ by effectors with different C-terminal motifs. Data were normalized to the vector control pGBT-9 (GBD), and are means±SE (n=4).

A region with a high percentage of proline (P) and glutamate (Q) residues is located between the C1 and C2 motifs of PvMYB4, and most of the sequence variations were found in this area (FIG. 1B, FIG. 2A). It has been reported that P-Q-rich and acidic-blob-type regions are associated with transcriptional activation domains (Ruden et al., 1991). To test this hypothesis, a fusion was created of the PQ motif (FIG. 2, box) with the GAL4 AD as an effector plasmid and was expressed in yeast with the 6GAL4-Mini-pCYC1:lacZ reporter construct. No transcriptional activation of β-galactosidase was detected (FIG. 5), indicating that the P-Q-rich region has no transcriptional activation activity.

Example 4

Expression of PvMYB4 in Transgenic Tobacco

Figures 6A, 6B:
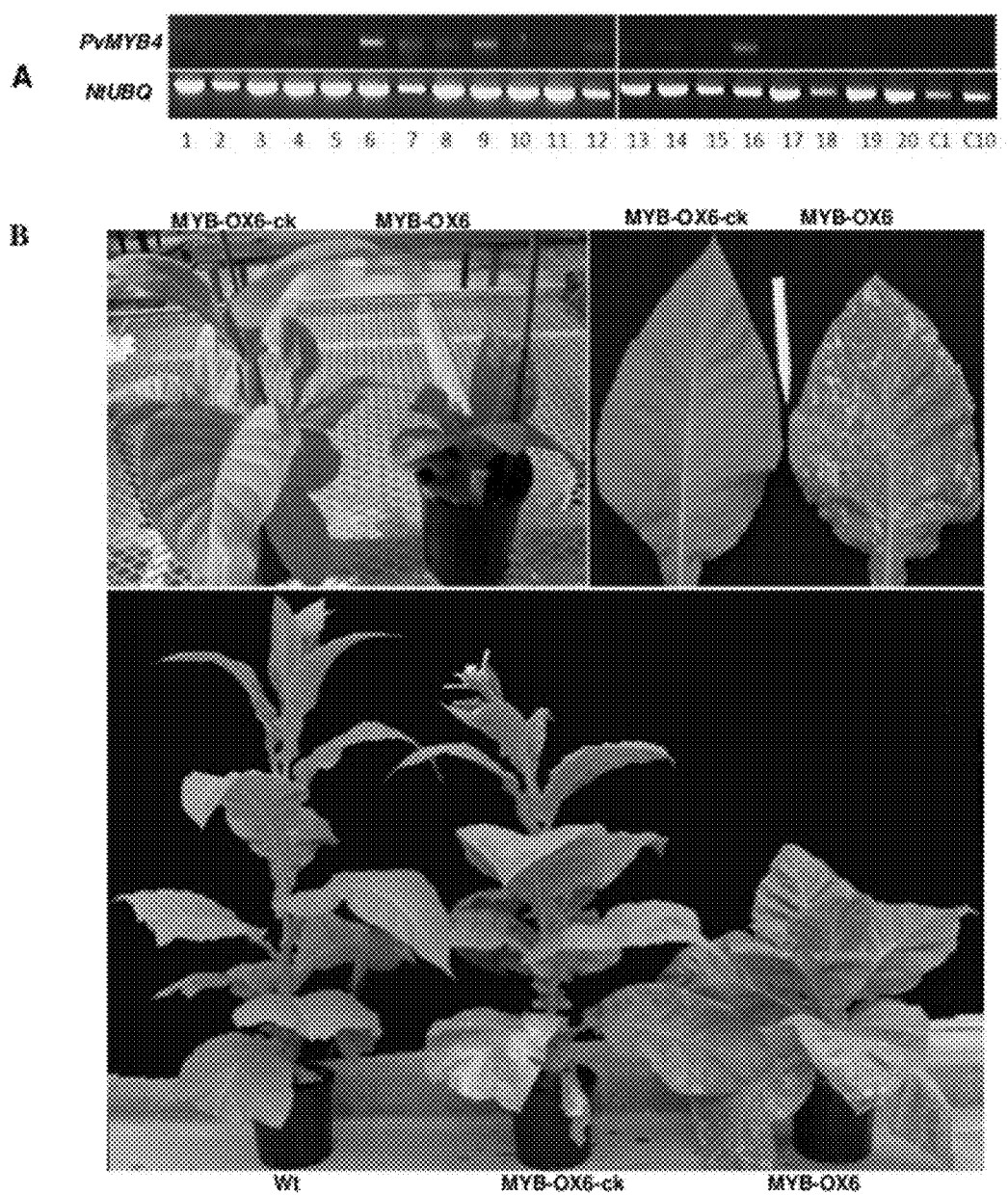
FIGS. 6A-6B show transgenic tobacco plants over-expressing PvMYB4 have reduced growth and lesion mimic phenotypes. (A) Semi-quantitative RT-PCR analysis of PvMYB4-OX transgenic tobacco plants. (B) Growth and leaf lesion phenotypes of PvMYB4OX6 transgenic tobacco plants.

To investigate the biological function of PvMYB4, it was over-expressed under the control of the constitutive 35S promoter in tobacco (MYB-OX). Several independent lines, such as #6, #9 and #16, showed relatively high expression of PvMYB4 transcripts (FIG. 6A). Over-expression of PvMYB4 gave rise to the same phenotypes as observed previously for AmMYB308 and AtMYB4 in transgenic tobacco (Tamagnone et al., 1998; Jin et al., 2000), namely a reduction in plant stature and appearance of numerous white lesions on the mature leaves (FIG. 6B). The latter phenotype has been linked to reduced levels of hydroxycinnamic acid derivatives (Elkind et al., 1990; Tamagnone et al., 1998).

Figures 7A, 7B, 7C, 7D, 7E, 7F, 7G, 7H:
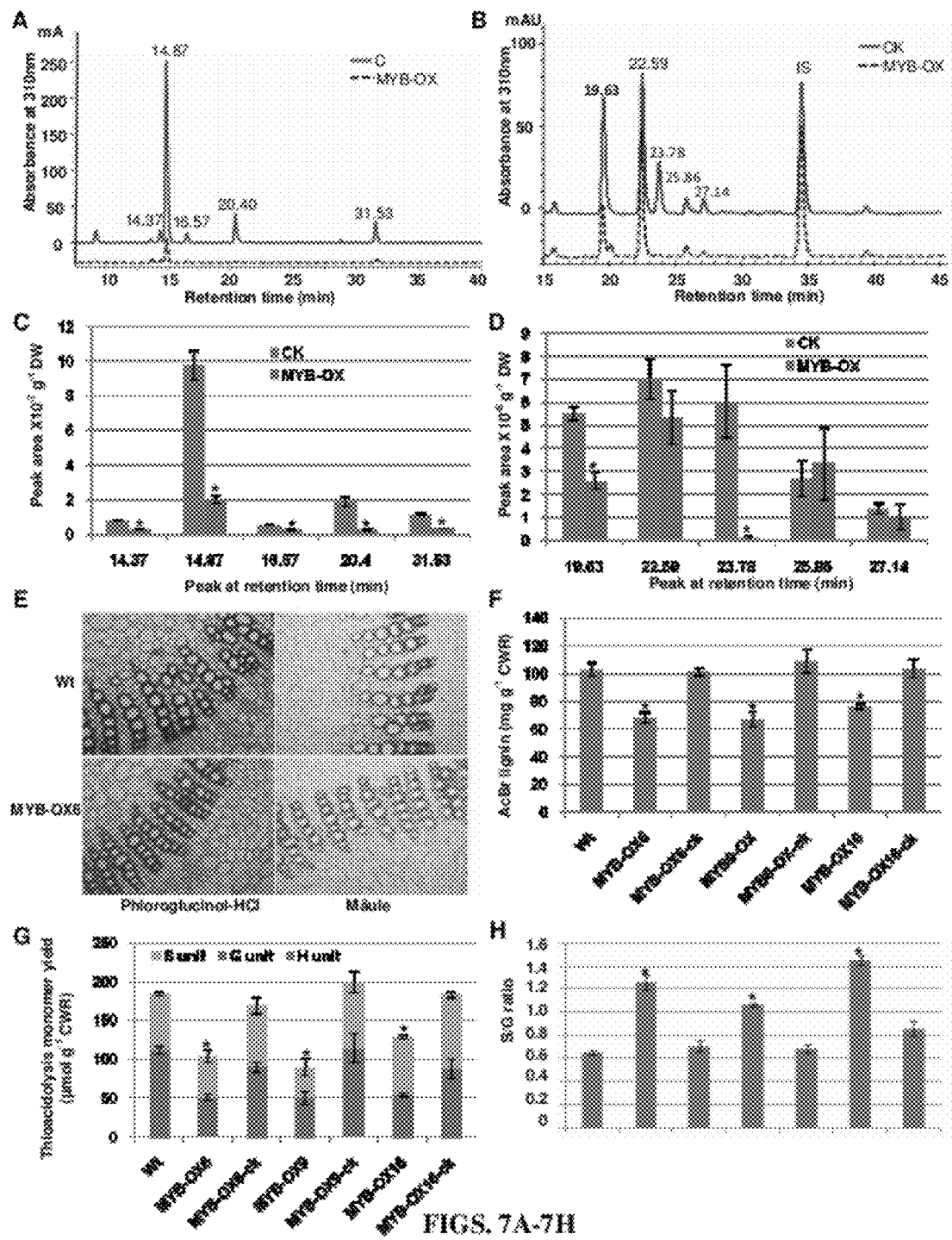
FIGS. 7A-7H show that over-expression of PvMYB4 alters phenylpropanoid metabolism in transgenic tobacco plants. (A, B) Typical HPLC chromatograms of methanol/water soluble fractions (A) and ester-linked wall bound phenolics (B) from stems of wild-type and PvMYB4-ox tobacco lines. (C, D) Quantification of the peaks in panels (A) and (B). The peak areas were quantified according to automatic integration of the HPLC signal using 32 Karat Software version 5.0 (Beckman Coulter, Fullerton, Calif.), and plotted as a function of dry weight (DW). The major soluble phenolic compound is chlorogenic acid (Rt=14.87 min). Wall bound ester-linked phenolic compounds: vanillin (Rt=19.63); syringyl aldehyde (Rt=22.59); p-coumaric acid (p-CA, Rt=23.78) and ferulic acid (FA, Rt=27.14) (E) Phloroglucinol-HCl staining (left panel) and Maule staining (right panel) of cross-sections of the leaf petioles of wild-type and PvMYB4-OX tobacco transgenic plants. (F) AcBr lignin content of stems of wild-type and PvMYB4-ox transgenic tobacco. (G) Lignin composition of stems of wild-type and PvMYB4-ox transgenic tobacco as determined by thioacidolysis. (H) S/G ratio (from thioacidolysis) of stems of wild-type and PvMYB4-ox transgenic tobacco. CWR, cell wall residue; S, syringyl unit; G, guaiacyl unit; H, p-hydroxyphenyl unit. All data are means±SE (n=6).

The most abundant soluble phenolic compound in methanolic extracts of tobacco stems is chlorogenic acid (CGA, Rt 14.87 min), which exists with a minor isomer (Rt=14.37 min) (FIG. 7A). Over-expression of PvMYB4 in tobacco caused an approximately 80% reduction in soluble CGA levels (FIGS. 7A,C). The most abundant ester-linked wall-bound phenolic compounds released from low temperature hydrolysis of tobacco stem cell walls are vanillin (Rt=19.63), syringyl aldehyde (Rt=22.59) and p-coumaric acid (p-CA, Rt=23.78). Over-expression of PvMYB4 significantly reduced the content of vanillin and p-CA compared to the wild type, but syringyl aldehyde levels were not significantly changed (FIGS. 7B, D).

The lignin content and composition of PvMYB4-OX transgenic tobacco plants were also significantly changed. Leaf petiole sections of PvMYB4-OX plants showed reduced staining with phloroglucinol-HCl (FIG. 7E), suggesting an overall reduced level of lignin, confirmed by the reduction in acetyl bromide lignin level (FIG. 7F). Maule staining showed a decrease in the red coloration of the xylem vessels, consistent with a reduction in S lignin (FIG. 7E), and this was confirmed by thioacidolysis analysis of lignin monomer yield (FIG. 7G). The latter indicated a reduction in lignin content of from 40-60% in the PvMYB4-OX over-expressing lines compared to controls (FIG. 7G). However, overall the G units were reduced more than the S units, leading to an increased S/G ratio in the MYB4 over-expressors (FIG. 7H).

Example 5

Over-Expression of PvMYB4 in Switchgrass

Figures 8A, 8B, 8C:
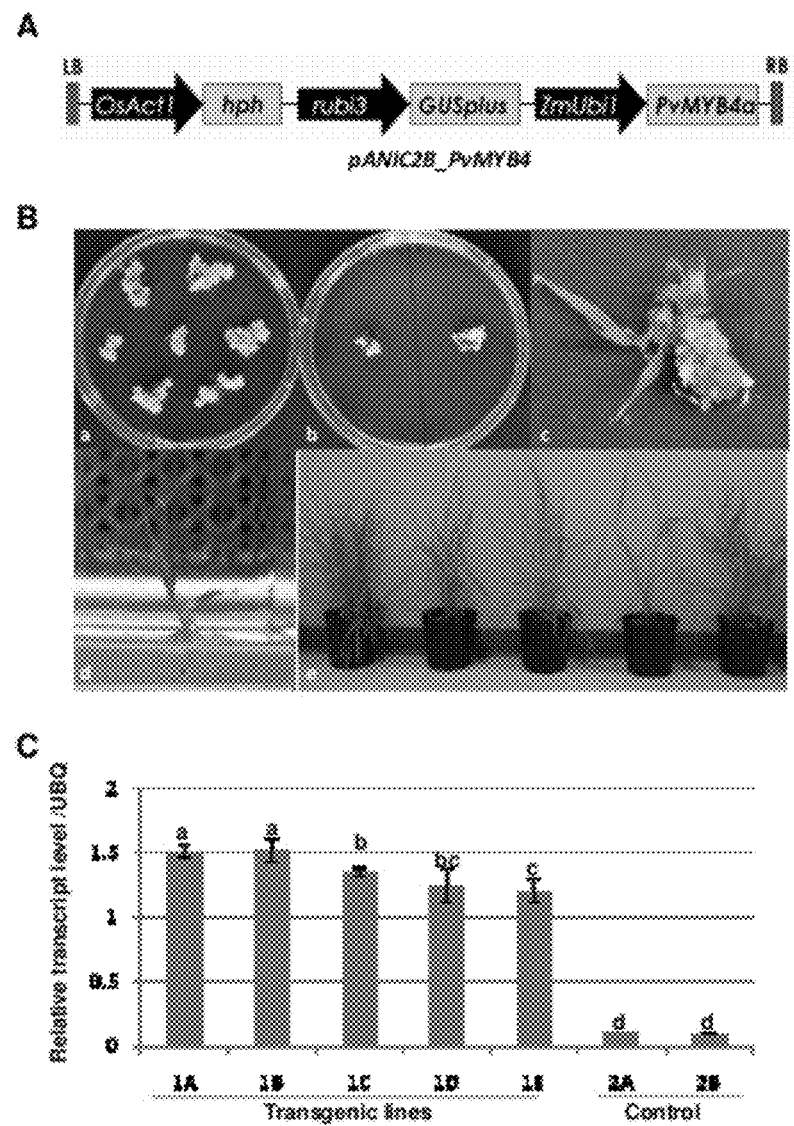
FIGS. 8A-8C show the results of over-expression of PvMYB4 in transgenic switchgrass. (A) pANIC2B-PvMYB4 construct used for switchgrass transformation. OsAct1, promoter of rice Actin1 gene; rubi3, promoter of rubisco3 gene; ZmUbi1, promoter of maize ubiquitin 1 gene. hph, hygromycin resistance gene for transformation selection marker. LB and RB, left and right borders of the T-DNA sequences. (B) Representative pictures of the switchgrass transformation procedure. a, embryonic callus used for transformation. b, transformed callus on selection media. c, regenerated seedlings on regeneration media. d, regenerated seedling on rooting media. e, putative regenerated PvMYB4-OX plants in greenhouse. (C) qRT-PCR analysis of PvMYB4 transcripts in control lines 2a-2b and PvMYB4-OX transgenic switchgrass lines 1a-1e. The qRT-PCR primer pairs are HS543 and HS544 (Table 1). Data are means±SE (n=3). Bars with the same letters are not significantly different.

To generate switchgrass PvMYB4-OX lines, the full length PvMYB4a open reading frame was cloned into the pANIC2B binary vector fused with an AcV5 epitope tag (Monsma and Blissard, 1995) at the C-terminal and driven by the maize ZmUbi promoter. The hygromycin (hph) resistance gene was used as selectable marker for transformation (FIG. 8A). Embryonic callus generated from immature inflorescences of switchgrass cv Alamo line ST2 was transformed by *Agrobacterium*-mediated transformation. The transformation process, based on modifications of previously published protocols (Somleva et al., 2002; Xi et al., 2009), is illustrated in FIG. 8B. The ST2 line was specifically selected for its high tissue culture response. Since the ST2 line is vegetatively propagated by tillers, all the lines are in the same genetic background, an important point for a highly heterozygous outcrossing species.

Figures 9A, 9B, 9C:
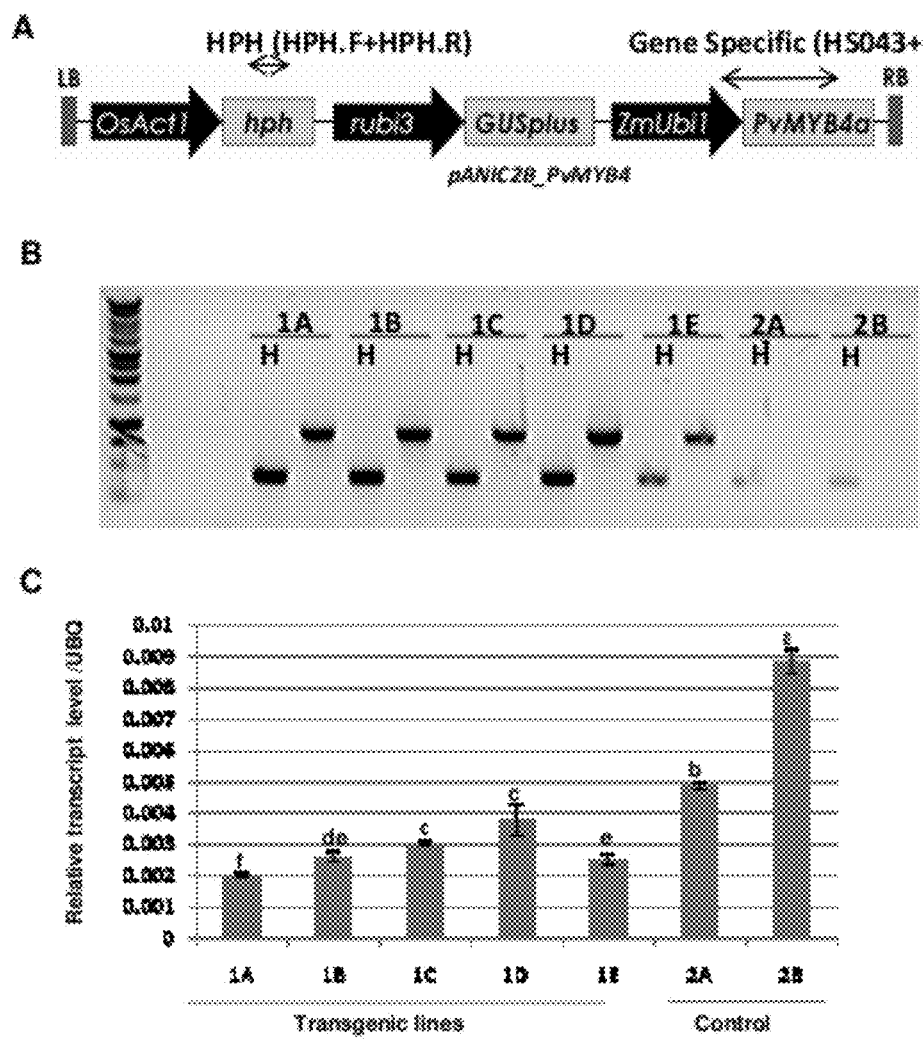
FIGS. 9A-9C are the construct and results of a genomic DNA PCR and qRT-PCR analysis of PvMYB4-OX transgenic switchgrass. (A) The pANIC2B-PvMYB4 construct showing the primer pairs used for genomic DNA PCR testing. HPH, hygromycin specific gene primer pairs; Gene specific, primer pairs covering the ZmUBI1 promoter region and PvMYB4 gene specific region. (B) Genomic DNA PCR. 2A and 2B are two control lines that only have the half T-DNA (HPH) part of the construct. (C) qRT-PCR analysis showing the endogenous PvMYB4 gene is down-regulated by the over-expression of PvMYB4 in switchgrass. Primer pairs are HS360 and HS361 (Table 1). Data are means±SE (n=3).

Genomic DNA PCR analysis showed that transgenic lines 2A and 2B could serve as appropriate controls because only the hygromycin resistance gene portion of the T-DNA was integrated into the genome (FIGS. 9A, B).

To confirm the over-expression of the PvMYB4 gene in the transgenic plants, two primers, HS543 and HS544, which cover the PvMYB4 ORF and AcV5 tag sequence, were used for qRT-PCR analysis (Table 1). The selected PvMYB4-OX lines exhibited a 10-12 fold increase in PvMYB4 expression (FIG. 8C) in transgenic switchgrass lines 1a-1e. The HS360 and HS361 primer pairs were designed from the 3'-UTR region of the PvMYB4 sequence to determine expression of the endogenous PvMYB4 genes in switchgrass (FIG. 9C). The endogenous PvMYB4 gene was repressed in the transgenic plants, indicating a similar self-repression feedback regulatory network as described for AtMYB4 in *Arabidopsis* (Zhao et al., 2007) (FIG. 9C).

Figures 10A, 10B, 10C:
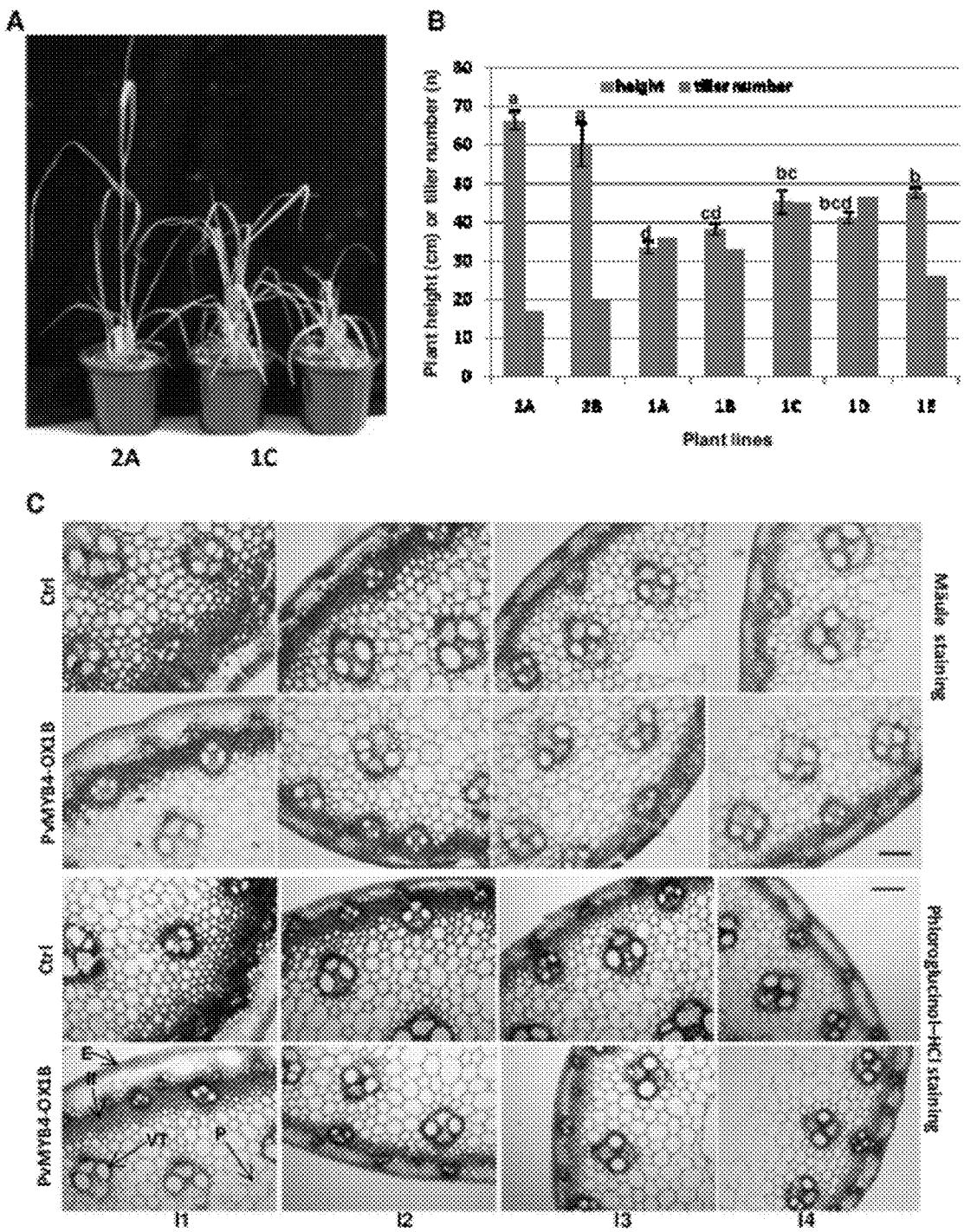
FIGS. 10A-10C demonstrate PvMYB4-OX transgenic switchgrass has reduced lignin and altered growth morphology. (A) Visible phenotypes of control (2A) and PvMYB4-OX transgenic switchgrass (1A, C). The over-expressing lines have reduced stature but increased tillering. (B) Plant height and tiller numbers for control and PvMYB4-OX transgenic switchgrass. Data are means±SE (n≥4). Bars with the same letters are not significantly different. (C) Phloroglucinol-HCl staining (bottom panel) and Maule staining (upper panel) of cross-sections of different internodes of PvMYB4-OX transgenic switchgrass. I1-I4: Internode 1 (bottom) to internode 4 (upper) of E4 tillers. VT, vascular tissue; P, parenchyma, E, epidermis; If, interfascicular fiber. Bar=100 μm

Over-expression of PvMYB4 in switchgrass had dramatic effects on plant morphology. The PvMYB4-OX transgenic plants showed a reduction in plant height (by about 40% on average) but more tillers (up to a 2.5-fold increase) (FIGS. 10A, B). In contrast to the PvMYB4-OX tobacco plants, no white lesions were observed on the leaves.

Figure 11A:
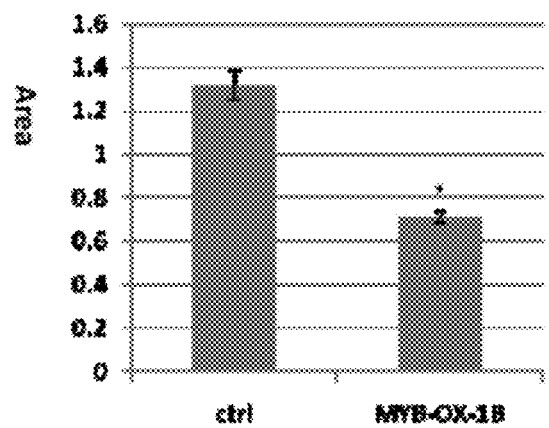
FIGS. 11A-11B illustrate that PvMYB4-OX transgenic switchgrass has smaller vascular bundles and thinner tillers. (A) Vascular bundle areas. The measurement was done with ImageJ (worldwideweb.rsbweb.nih.gov/ij) software. Bars show standard errors of the means (n≥8). Only the vascular bundles within the 12 (E4 stage) were measured and compared unless they were located in the interfascicular fiber area of the stem. (B) Tiller diameter. Only the middle parts of 12 internode of E4 stage tillers were measured with the venire scale. Data are means±SE (n≥5).
Figure 11B:
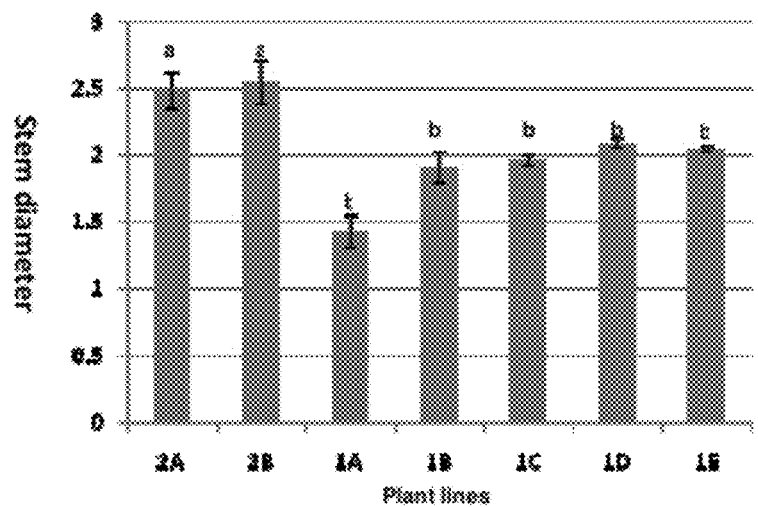

A. PvMYB4 Over-Expression Reduces Lignin Levels, Alters Cell-Wall Phenolic Levels, and Reduces Recalcitrance in Transgenic Switchgrass The lignin levels in the middle parts of the different internodes of E4 stage stems of PvMYB4-OX and control switchgrass plants were first evaluated by staining with phloroglucinol-HCl and Maule reagent. Clearly, total lignin levels (phloroglucinol-HCl staining, red color) and S lignin (Maule staining, reddish-brown color) were reduced in all the internodes of the transgenic plants, especially the mature I1 and I2 internodes (FIG. 10C). Furthermore, although the structure of the vascular bundles remained the same, their size was significantly reduced in the transgenic plants based on the measurement of vascular bundles from internode 2 (FIG. 10C, FIG. 11A). Tillers of PvMYB4-OX lines were thinner than those of the controls (FIG. 11B).

Figures 12A, 12B, 12C, 12D, 12E, 12F:
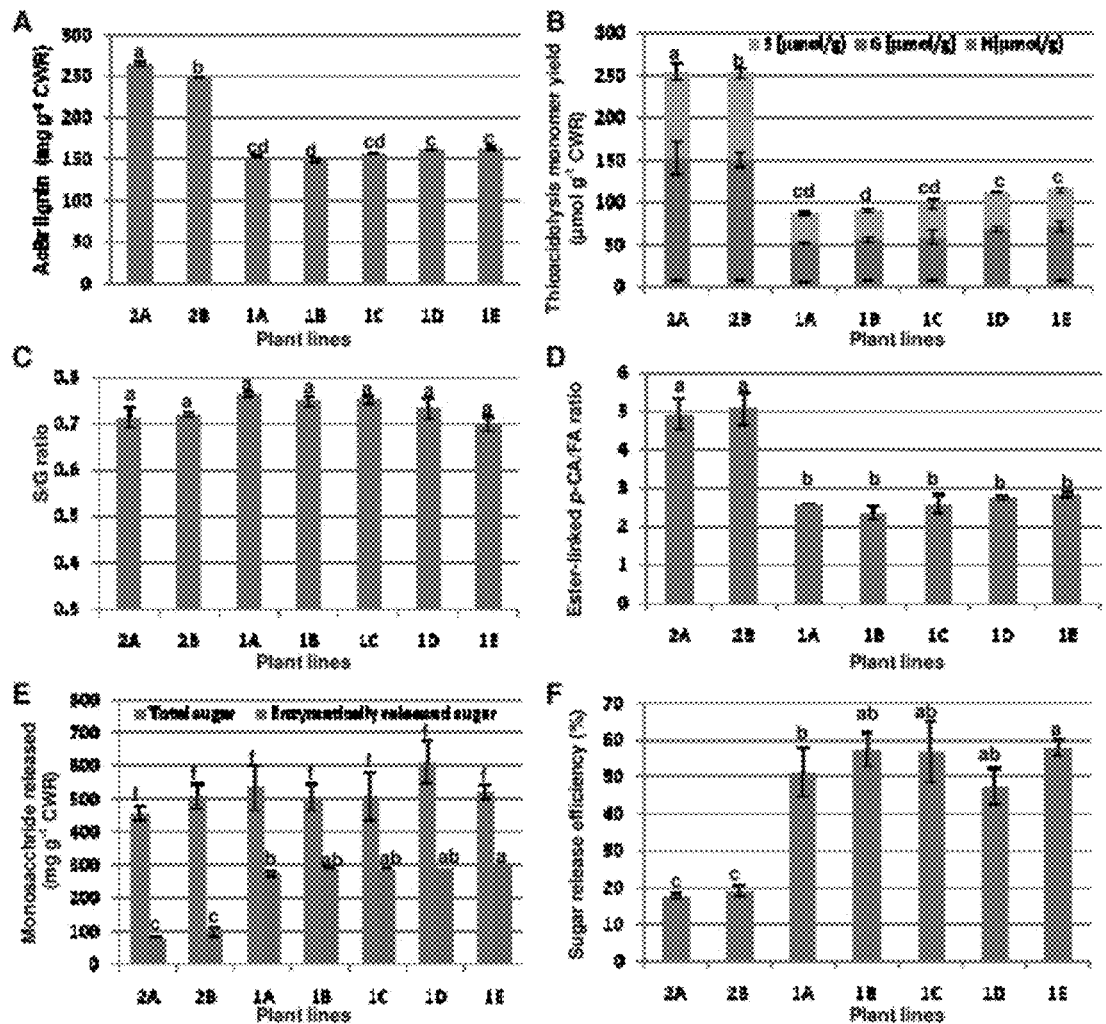
FIGS. 12A-12F show that over-expression of PvMYB4 alters phenylpropanoid metabolism in transgenic switchgrass plants. (A) AcBr lignin content of whole E4 stems. (B) lignin composition determined by thioacidolysis. (C) S/G ratio. CWR, cell wall residue; S, syringyl unit; G, guaiacyl unit; H, p-hydroxyphenyl unit. (D) p-Coumaric acid/ferulic acid ratios of the ester-linked wall-bound phenolics. (E) Total monosaccharide released from CWR and monosaccharide released from enzymatic saccharification without acid pre-treatment. (F) Sugar release efficiency of enzymatic saccharification without acid pre-treatment. Data are means±SE (n=3). 2A, 2B are two control lines. Bars with the same letters are not significantly different.
Figure 13:
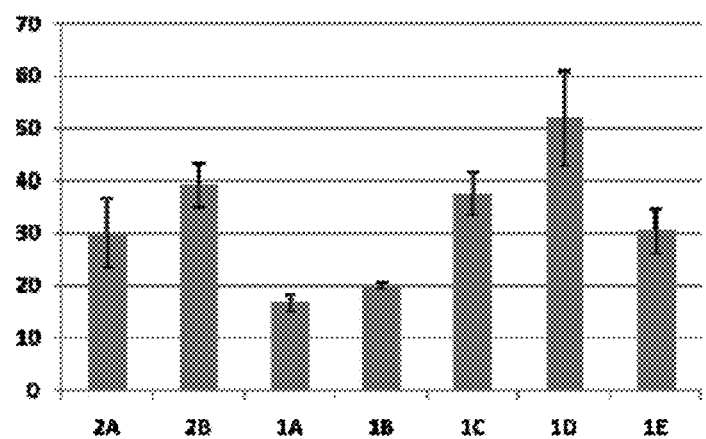
FIG. 13 provide an estimation of total dry biomass yield for PvMYB4-OX transgenic switchgrass. Only the tillers at E4 stage were measured. Total dry biomass was estimated by multiplying the average tiller dry biomass with the total tiller number within the same time period. Data are means±SE (n≥3).

Total lignin levels in whole stems of E4 stage plants were reduced by about 40-50% (determined as AcBr lignin) or 60-70% (determined by thioacidolysis) as a result of over-expression of PvMYB4 (FIGS. 12A, B). However, in contrast to the PvMYB4-OX tobacco lines, the S/G ratio was only slightly increased (FIG. 12C). The ester linked p-CA/FA ratio was reduced about 50% compared to the control lines (FIG. 12D). Since both the lignin content and the ester linked p-CA/FA ratio are reduced in the PvMYB4-OX transgenic switchgrass lines, these lines could exhibit significantly higher saccharification efficiency than the control lines based on previous observations of natural variation (Shen et al., 2009b). To test this, sugar release from cell wall residues (CWR) was measured by enzymatic saccharification without acid pre-treatment. The total sugar released from the PvMYB4-OX transgenic switchgrass lines as a function of total available cell wall sugar levels was about three-fold higher from the PvMYB4 over-expressing lines than from the controls (FIGS. 12E, F). Dry biomass production was estimated under greenhouse condition, the transgenic PvMYB4-OX lines have less (1A, 1B and 1E lines), similar (line 1C) or about 20% increased (line 1D) biomass depending on the different transgenic lines. (FIG. 13).

B. Downstream Target Genes of PvMYB4

Given that PvMYB4 represses phenylpropanoid metabolism and lignin content in both switchgrass and tobacco, and represses transcription of the *Arabidopsis* PAL0 and CCoAOMT7 promoters in vitro, the transgenic PvMYB4-OX tobacco system was used to gain a broader picture of the downstream gene targets. Total RNA was extracted from the leaves of control and PvMYB4-OX tobacco lines. First strand cDNA was synthesized and quantitative RT-PCR primer pairs (Table 1) were designed for each of the genes encoding the enzymes of phenylpropanoid and monolignol biosynthesis.

TABLE 1

Primer sequences

| Primer code | Primer name | Sequence (SEQ ID NO) |
|---|---|---|
| | | PvMYB4 cloning |
| HS010 | MYB1_6497.F | caccATGGGGCGGTCGCCGTGCTG (SEQ ID NO: 111) |
| HS011 | MYB1_6497.R | TCAAACAAAAAAAAACAGCCCAAC (SEQ ID NO: 112) |
| | | Genomic DNA PCR |
| HS043 | Zmubi.pro.F2 | TCTTTTGTCGATGCTCACC (SEQ ID NO: 113) |
| HS314 | HS314.MYB1.R1 | TCACTTCATCTCGAGGCCTC (SEQ ID NO: 114) |
| | HPH.F | AAGGAATCGGTCAATACACTACATGG (SEQ ID NO: 115) |
| | HPH.R | AAGACCAATGCGGAGCATATACG (SEQ ID NO: 116) |
| | | In Situ Hybridization |
| | PvMYB_T7_F | GCGTAATACGACTCACTATAGGGTGCTGCGAGAAGGCGCAC (SEQ ID NO: 117) |
| | PvMYB_T7_R | GCGTAATACGACTCACTATAGGGTCATCTCGAGGCCTCTGAAG (SEQ ID NO: 118) |
| | PvMYB_F | TGCTGCGAGAAGGCGCAC (SEQ ID NO: 119) |
| | PvMYB_R | TCATCTCGAGGCCTCTGAAG (SEQ ID NO: 120) |
| | | PvMYB4 qRT-PCR in switchgrass |
| HS543 | PvMYB4.F | TCGGCATGCTCCTCGACTTC (SEQ ID NO: 121) |
| HS544 | AcV5.R | ACCAGCCGCTCGCATCTTTC (SEQ ID NO: 122) |
| HS360 | PvMYB1_798F | AGGCCTCGAGATGAAGTGAAAC (SEQ ID NO: 123) |
| HS361 | PvMYB1_859R | AGCCCAACAAACAAACGAAATT (SEQ ID NO: 124) |
| HS126 | MYB_7X_QRTF1 | CTCAATCTCGACCTCTGCATCA (SEQ ID NO: 125) |
| HS127 | MYB_7X_QRTR1 | ACGAGCTCCTGGTCCTCTTCT (SEQ ID NO: 126) |
| HS334 | MYBqRTR1 | ATGAGCTCCTGGTCCTCTTCT (SEQ ID NO: 127) |
| HS335 | MYB.R3 | GAGCTCCTGGTCCTCTTC (SEQ ID NO: 128) |
| HS181 | PAL_F | CATATAGTGTGCGTGCGTGT (SEQ ID NO: 129) |
| HS182 | PAL_R | CTGGCCCGCCAATCG (SEQ ID NO: 130) |
| HS090 | C4H1_1534F | GGGCAGTTCAGCAACCAGAT (SEQ ID NO: 131) |
| HS091 | C4H1_1611R | CGCGTTTCCGGGACTCTAG (SEQ ID NO: 132) |
| HS094 | C3H1_739F | TTGAGATGGTTGTGTCCGCTTA (SEQ ID NO: 133) |
| HS095 | C3H1_803R | AGGCGGTCCCTTCTCTCATT (SEQ ID NO: 134) |
| | PvCOMT_F461 | CAACCGCGTGTTCAACGA (SEQ ID NO: 135) |
| | PvCOMT_R534 | CGGTGTAGAACTCGAGCAGCTT (SEQ ID NO: 136) |
| HS108 | F5H_1720F | CTCTTCTATTTGTGCGTGTAACTGTGT (SEQ ID NO: 137) |
| HS109 | F5H_1792R | CAGCCCTATAGCATCGACATGA (SEQ ID NO: 138) |
| | 4CL1_1179_F | CGAGCAGATCATGAAAGGTTACC (SEQ ID NO: 139) |
| | 4CL1_1251_R | CAGCCAGCCGTCCTTGTC (SEQ ID NO: 140) |
| HS100 | CCOMT_966F | CCGTCTTTCTTTTTTTGGCTCTT (SEQ ID NO: 141) |
| HS101 | CCOMT_1029R | GCATGAAAATGATGACAGTTTCCA (SEQ ID NO: 142) |

TABLE 1-continued

Primer sequences

| Primer code | Primer name | Sequence (SEQ ID NO) |
|---|---|---|
| | PvCCR1.112_F | GCGTCGTGGCTCGTCAA (SEQ ID NO: 143) |
| | PvCCR1.187_R | TCGGGTCATCTGGGTTCCT (SEQ ID NO: 144) |
| | PvCAD_F116 | TCACATCAAGCATCCACCATCT (SEQ ID NO: 145) |
| | PvCAD_R184 | GTTCTCGTGTCCGAGGTGTGT (SEQ ID NO: 146) |
| | HCT_973_F | GCAGAAGGAGCAGCAGTCATC (SEQ ID NO: 147) |
| | HCT_1035_R | CGAGCGGCAATAGTCGTTGT (SEQ ID NO: 148) |
| HS545 | PvGA20ox1a.F | CACCATGCACCACCTCTCAA (SEQ ID NO: 149) |
| HS546 | PvGA20ox1a.R | ATGCAAATCCCCATCCAGATAT (SEQ ID NO: 150) |
| HS551 | PvGA20ox2a.F | TGGGCCGGGATTTCG (SEQ ID NO: 151) |
| HS552 | PvGA20ox2a.R | CCATGATCGTCAGCGACAAA (SEQ ID NO: 152) | qRT-PCR primers for PvMYB4-OX transgenic tobacco

| | | |
|---|---|---|
| HS368 | NtGA20ox1.F | TGTAGCACGAGAACTTCC (SEQ ID NO: 153) |
| HS369 | NtGA20ox1.R | ACGGCATGCTTCACCAACA (SEQ ID NO: 154) |
| HS384 | NtRSG1.F | GGCCACGTCCGCATTTC (SEQ ID NO: 155) |
| HS385 | NtRSG1.R | GCATGGTGACTACCACATTGGA (SEQ ID NO: 156) |
| | PAL.F | GACAAAGTGTTCACAGCAATG (SEQ ID NO: 157) |
| | PAL.R | TAACAGATWGGAAGAGGAGCA (SEQ ID NO: 158) |
| | C4H.F | TCAACACAATGGTGGAATGC (SEQ ID NO: 159) |
| | C4H.R | ACTTTGGGACGTTTGGTTCA (SEQ ID NO: 160) |
| | 4CL.F | CTTCTCAACCATCCCAACATT (SEQ ID NO: 161) |
| | 4CL.R | CTAACAACAAAAGCCACTGGA (SEQ ID NO: 162) |
| | HCT.F | GGCTGCCAATCCATGATGCT (SEQ ID NO: 163) |
| | HCT.R | GCAACAGATTGACTGCCATCA (SEQ ID NO: 164) |
| | C3H.F | TGGCTGAGGTGATCAAGAAC (SEQ ID NO: 165) |
| | C3H.R | TATGGGAGGTTGGGGAAGTC (SEQ ID NO: 166) |
| | CCoAOMT.F | ACACCCTATGGAATGGATCA (SEQ ID NO: 167) |
| | CCoAOMT.R | CCTTGTTGAGTTCCAATACGA (SEQ ID NO: 168) |
| | F5H.F | GAAACTCTACGACTTCACCC (SEQ ID NO: 169) |
| | F5H.R | TGACTTTGCCGGAATATGGT (SEQ ID NO: 170) |
| | COMT.F | CCTGCAAATGGGAAGGTGAT (SEQ ID NO: 171) |
| | COMT.R | CAGTCCTTTCTTTGCCTCCT (SEQ ID NO: 172) |
| | CAD.F | CTCGGGAGAAAGAGCATCAC (SEQ ID NO: 173) |
| | CAD.R | CCTCTCCATTGCAGTGTTGA (SEQ ID NO: 174) |
| | CCR.F | ATGTGACGAAGCCAAGGGTAA (SEQ ID NO: 175) |
| | CCR.R | GTAGGAATTGGAAGGTGACCT (SEQ ID NO: 176) |
| | qCHS.F | CACCGCTGTCACGTTTCGT (SEQ ID NO: 177) |
| | qCHS.R | AGGGCTTGCCCAACTAAACTATC (SEQ ID NO: 178) |

TABLE 1-continued

Primer sequences

| Primer code | Primer name | Sequence (SEQ ID NO) |
|---|---|---|
| | qCHI.F | TGCAGAGAGTCAGGCCATTG (SEQ ID NO: 179) |
| | qCHI.R | CGGCGGGAAGGTTTCATT (SEQ ID NO: 180) |
| | qFLS.F | GCGAGAAGTTGCGGAGAAGA (SEQ ID NO: 181) |
| | qFLS.R | CATCATTTCATGGGCTTCTAACC (SEQ ID NO: 182) |
| | | Oligonucleotides used in electrophoretic mobility shift assays (EMSAs) |
| HS428 | AC1.F | CGGTACCAGTCCACCTACCGCCACCTACCGCCACCTACCGCTGTTCTCGA (SEQ ID NO: 183) |
| HS429 | AC1.R | TCGAGAACAGCGGTAGGTGGCGGTAGGTGGCGGTAGGTGGACTGGTACCG (SEQ ID NO: 184) |
| HS480 | AC2.F | CGGTACCAGTCCACCAACCGCCACCAACCGCCACCAACCGCTGTTCTCGA (SEQ ID NO: 185) |
| HS481 | AC2.R | TCGAGAACAGCGGTTGGTGGCGGTTGGTGGCGGTTGGTGGACTGGTACCG (SEQ ID NO: 186) |
| HS484 | AC3.F | CCAGTCCACCTAACTCTACCTAACTCTACCTAACGCTGTTC (SEQ ID NO: 187) |
| HS485 | AC3.R | GAACAGCGTTAGGTAGAGTTAGGTAGAGTTAGGTGGACTGG (SEQ ID NO: 188) |
| HS400 | AC4.F | CCAGTCCACCAAACTCTACCAAACTCTACCAAACGCTGTTC (SEQ ID NO: 189) |
| HS401 | AC4.R | GAACAGCGTTTGGTAGAGTTTGGTAGAGTTTGGTGGACTGG (SEQ ID NO: 190) |
| HS444 | AtGA20ox2.AC2.F | CTTAACTCTTAACTGGTCGAACCAACCATGAATGATTTGGGCATAAT (SEQ ID NO: 191) |
| HS445 | AtGA20ox2.AC2.R | ATTATGCCCAAATCATTCATGGTTGGTTCGACCAGTTAAGAGTTAAG (SEQ ID NO: 192) |
| HS440 | AtGA20ox2.AC4.F | ATTATAAGAAAGATTAAAAAACCAAACAAATGTACACTAACATGACT (SEQ ID NO: 19) |
| HS441 | AtGA20ox2.AC4.R | AGTCATGTTAGTGTACATTTGTTTGGTTTTTTAATCTTTCTTATAAT (SEQ ID NO: 23) |

Figures 14A, 14B, 14C, 14D, 14E, 14F:
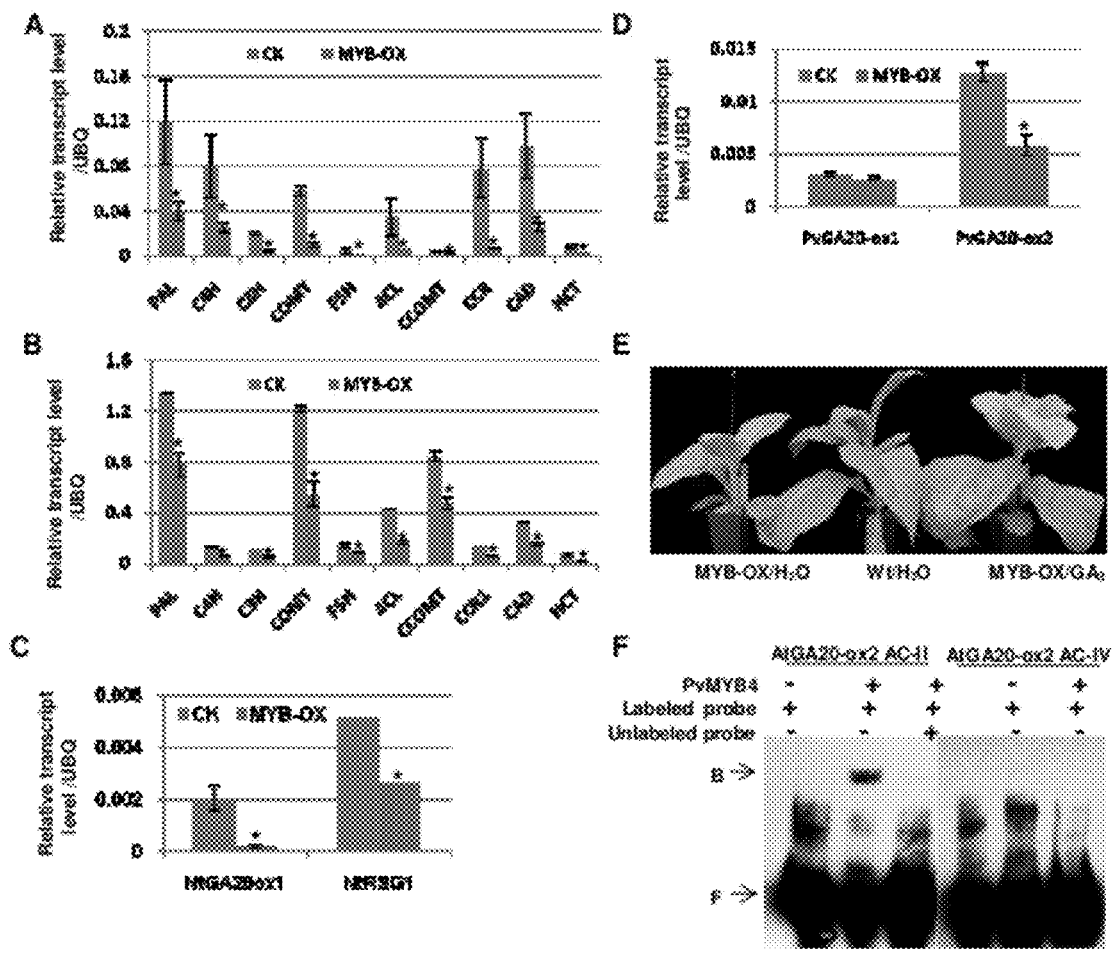
FIGS. 14A-14F identify genes down-regulated by PvMYB4 in tobacco and evidence for effects on gibberellin (GA) biosynthesis. (A) qRT-PCR analysis of the expression levels of lignin synthetic genes in PvMYB4-OX transgenic tobacco. (B) qRT-PCR analysis of the expression levels of lignin synthetic genes in PvMYB4-OX transgenic switchgrass. (C) qRT-PCR analysis of the expression levels of NtGA20-ox1 and NtRSG genes in PvMYB4-OX transgenic tobacco. (D) qRT-PCR analysis of the expression levels of PvGA20-ox1 and PvGA20-ox2 genes in PvMYB4-OX transgenic switchgrass. (E) Exogenous GA application restores growth to PvMYB4-OX transgenic tobacco. (F) PvMYB4 binds to the AC-II element of the AtGA20-ox2 promoter in EMSA assays. F, free probe; B, bound complex. Data are means±SE (n≥3).
Figures 15A, 15B:
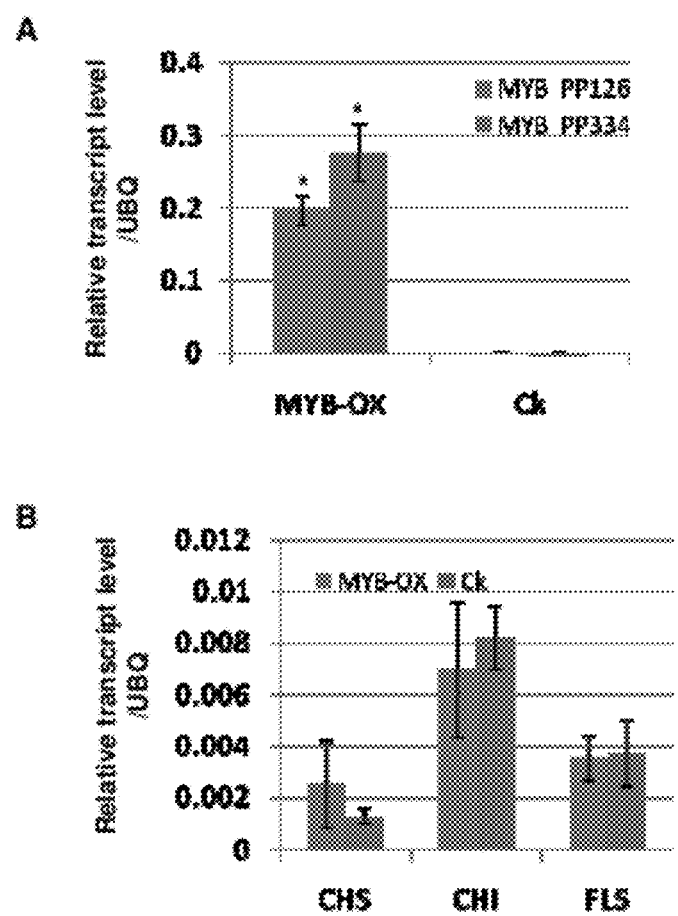
FIGS. 15A-15B are a qRT-PCR analysis of flavonoid biosynthetic gene transcripts in PvMYB4-OX transgenic tobacco. (A) qRT-PCR analysis showing the expression level of PvMYB4 in transgenic tobacco with two primer pairs. PP_126, primer pairs HS126+HS127; PP_334, primer pairs HS334+HS335. (B) qRT-PCR analysis showing the expression level of flavonoid biosynthetic genes in transgenic tobacco. CHS, chalcone synthase; CHI, chalcone isomerase; FLS, flavonol synthase. Data are mean±standard error (SE) (n=3).

In the transgenic control lines, F5H (ferulate 5-hydroxylase), CCoAOMT and HCT (hydroxycinnamoyl CoA: shikimate hydroxycinnamoyl transferase) genes showed overall lower transcript levels compared to other genes (FIGS. 14A, B). The transcript levels of PAL, C4H, C3'H (coumaroyl shikimate 3'-hydroxylase), 4CL (4-coumarate:CoA ligase), COMT (caffeic acid 3-O-methyltransferase), CCR (cinnamoyl CoA reductase) and CAD genes were reduced by at least 70% in the PvMYB4-OX tobacco lines (FIG. 14A) and 50% in the switchgrass lines (FIG. 14B). Because of potential cross-talk and/or spillover between lignin and flavonoid pathways in plants down-regulated in lignin biosynthesis (Besseau et al., 2007), genes involved in flavonoid biosynthesis (chalcone synthase, chalcone isomerase and flavonol synthase) were also analyzed, but none of these was affected by over-expression of PvMYB4 (FIG. 15).

A reduced-growth phenotype has been reported in transgenic plants of several species over-expressing different MYB subfamily 4 genes (Tamagnone et al., 1998; Jin et al., 2000; Formlé et al., 2006; Fornal et al., 2010), suggesting a common genetic regulatory mechanism. Many plant mutants with dwarf or reduced-growth phenotypes are defective in the biosynthesis or perception of hormones such as gibberellins (Hedden and Proebsting, 1999; Thomas and Sun, 2004) or brassinosteroids (Fujioka and Sakurai, 1997). Gibberellic acid ($GA_3$) was applied to the PvMYB4-OX tobacco lines. The application of exogenous $GA_3$ rescued the growth phenotype of the PvMYB4-OX lines, suggesting possible defects in GA synthesis in the transgenic tobacco plants (FIG. 14E).

To test if PvMYB4 is involved in genetic regulation of the gibberellin (GA) biosynthesis pathway, relative gene expression level changes using qRT-PCR analysis was assessed. GA20-ox is a key enzyme for synthesis of the bioactive form of GA, and the most highly expressed form in tobacco leaves is GA20-ox1 (Gallego-Giraldo et al., 2007). GA20-ox1 transcript levels were repressed by 98% in the leaf tissues of the PvMYB4-OX lines (FIG. 14C). At the same time, transcripts encoding a bZIP transcription factor, NtRSG, that activates GA biosynthesis pathway genes (Fukazawa et al., 2000), were also repressed, by about 40-50% (FIG. 14C). Expression of putative PvGA20-ox1 and PvGA20-ox2 transcripts in the PVMYB4-OX transgenic switchgrass lines was also assessed, and the expression of PvGA20-ox2 was repressed about 50% while PvGA20-ox1 was not affected (FIG. 14D).

C. PvMYB4 Binds Directly to an AC Element in the AtGA20-OX2 Promoter

The present and previous studies indicate that subfamily 4 MYB proteins directly bind the AC cis-elements in downstream monolignol biosynthesis gene promoters (Legay et al., 2007; Sonbol et al., 2009). The above demonstration of down-regulation of GA20-ox expression raised the question of whether PvMYB4 also binds to the promoter of this gene. Gel shift assays were performed to test for possible direct binding of PvMYB4 to different AtGA20-ox2 promoter regions in vitro. Analysis of the AtGA20-ox2 promoter 1500 bp upstream of the transcription start site identified an AC-II (−1200 bp) and an AC-IV (−150 bp) element. EMSA assays indicated that the PvMYB4 protein binds directly to the AC-II element but not to the AC-IV element (FIG. 14F). This is consistent with the direct binding of PvMYB4 to the synthetic AC-II elements (FIG. 4F). Binding of PvMYB4 to the AC elements in the GA20-ox promoter appears to inhibit expression of the gene.

Example 6

Materials and Methods

A. Plant Materials and Growth Conditions

Tobacco (*Nicotiana tabacum* cv. Xanthi N N) and switchgrass (*Panicum virgatum* L. cv. Alamo) were grown in the greenhouse under standard conditions [temperature range 25-29° C. with a 16-hour day from 6:00 to 22:00 hours facilitated by supplementary lighting (parabolic aluminized reflector, 125-55 $\mu mol \cdot m^{-2}$) and relative humidity 77-22%, average 51%]. Plants were watered two to three times per week, with fertilizer (Peters 20-10-20, 100 ppm) added in the last watering. For tissue-specific gene expression pattern analysis, roots, leaves, leaf sheaths, internodes, and flowers were collected at the reproduction (R1) developmental stage (Moore et al., 1991). Samples were immediately frozen in liquid nitrogen and kept at −80° C. for storage, or were ground to powder in a freezer mill (SPEX SamplePrep, Metuchen, N.J.) under liquid nitrogen for further RNA isolation and analysis of lignin and soluble and wall-bound phenolics.

For treatment with GA, 4-week old tobacco plants were transplanted into 4-L pots and grown in a chamber at 25° C. and 12-hour light (irradiance 180 $\mu mol \cdot m^{-2}$ from both fluorescent and incandescent bulbs) and 12-hour dark cycle. Plants were watered with tap water containing $10^{-6}$ mol/L $GA_3$ two times per week for 4 weeks.

B. Analysis of Lignin, Phenolic Compounds and Sugar Release Efficiency

Cell wall residues (CWR) were prepared by sequentially extracting tobacco stems and switchgrass whole tillers with chloroform/methanol (1:1), 100% methanol, 50% methanol, and water (three times each). Fifteen milligram of lyophilized sample was used for lignin analysis. The acetyl bromide method was employed to determine total lignin content, and thioacidolysis followed by gas chromatography-mass spectrometry was used to identify and quantify lignin-derived monomers. Soluble phenolics were extracted from 30.0 mg freeze-dried tissue powder with 1.5 mL 50% methanol plus 1.5% acetic acid for 12 hours at room temperature. One hundred milligrams of extractive-free CWR were used for analysis of esterified cell wall-bound phenolics using low-temperature alkaline hydrolysis. About 100 mg and 125 mg of CWR were used for determination of total sugar release and enzymatic saccharification without acid pre-treatment, respectively. Full details of all analytical methods have been described previously (Shen et al., 2009b).

C. RNA Isolation and qRT-PCR

Total RNA was isolated with an Rneasy Mini Kit (QIAGEN, Valencia, Calif.). RNA quality was analyzed with an Agilent 2100 Bioanalyzer. Two µg (tobacco) and 3 µg (switchgrass) of total RNA were treated with Dnase (Applied Biosystems, Ambion, Austin, Tex.) for 1 hour to remove genomic DNA contamination and then used for reverse transcription with a reverse transcript III kit (Invitrogen Corporation, Carlsbad, Calif.) according to the manufacturer's protocol. The cDNA samples were diluted 20-fold and 2 µl diluted cDNA samples were used as the qRT-PCR templates. qRT-PCR and data analysis were as described previously (Karlen et al., 2007; Shen et al., 2009b). Primer pairs used for qRT-PCR are listed in Table 1.

D. Transcriptional Repression and Domain Mapping in Yeast

The pYES2 (Invitrogen) and pGBT-9 (Clontech Laboratories, Mountain View, Calif.) vectors were used to construct the effector plasmids for transcriptional repression activity assay and the effector plasmids for motif mapping assays, respectively. The pLacZi based vectors (3AC-1 and 3AC-II) were a gift from Dr. Malcolm Campbell (University of Toronto) (Patzlaff et al., 2003). The reporter plasmids were first integrated into the genome of yeast strain YM4721 purchased from ATCC (American Type Culture Collection, Manassas, Va.) as described by yeast protocols handbook (Clontech) to make the reporter strains. About 1 µg of effector plasmid were transformed into the yeast reporter strains with the EZ-Yeast transformation kit (MP Biomedicals, Solon, Ohio). β-Galactosidase assays were preformed as described in the yeast protocols handbook (Clontech).

E. In Situ Hybridization

Primers spanning 757 bp of the PvMYB4 open reading frame were designed using PrimerQuest (worldwideweb.idtdna.com/Scitools/Applications/Primerquest/). After the cDNA template was obtained, separate reactions were performed for making the sense and antisense probes. The T7 promoter sequence was added in front of the reverse primer and the PCR reaction was conducted with the forward primers without T7 to make an antisense probe. In the same way, T7 promoter was added to the front of the forward primer in combination with the reverse primer without T7 to make the sense control probe. The specific primers used for PvMYB4 are listed in Table 1. The probe was synthesized by in vitro transcription with a MAXIscript Kit (AM1308-AM1326) with 0.4-0.6 µg of template DNA obtained as described above. Digoxigenin-11-uridine-5'-triphosphate (DIG-11-UTP, Roche Applied Science) was used for the labeling. The quality and quantity of the probes were checked with a Bioanalyzer.

The tissue preparation including fixation, dehydration, and paraffin embedding were as described previously (Jackson, 1991). After sectioning, the switchgrass stem sections were rehydrated with an ethanol to water series after the paraffin had been removed by two 10-minute incubations in Histoclear (National Diagnostics). After brief equilibration in 0.1 M triethanolamine, the tissue was acetylated with 0.25% acetic anhydride in 0.1 M triethanolamine for 10 minutes. Sections were then washed twice with 1×PBS buffer for 5 minutes before and after triethanolamine treatment. Prehybridization, in situ hybridization, and imaging methods were as described previously (Zhou et al., 2010).

F. Dual Luciferase Assay

*Arabidopsis* protoplasts were isolated according to a previously published protocol with minor modifications (Sheen, 2001; Asai et al., 2002). In brief, leaves from healthy 30-day-old *Arabidopsis* were cut into 0.5-1 mm strips with fresh razor blades. The leaf strips were put into an enzyme solution composed of cellulase and macroenzyme, vacuum infiltrated for 20 minutes, then digested for 3 hours without shaking in the dark. After filtration, the protoplasts were collected, and transformed by PEG transfection. To make the effector constructs, coding sequences of PvMYB4 were inserted after the 35S promoter of the Gateway over-expression vector P2GW7 (gateway.psb.ugent.be/). Reporter constructs were prepared as reported (Wang et al., 2010). Promoter activities were represented by Firefly LUC/Renilla LUC activities, and normalized to the value obtained from protoplasts transformed with empty vector.

G. Cell Imaging and Histochemical Staining

Switchgrass internode samples and tobacco leaf petioles were collected in the greenhouse and immediately frozen in liquid nitrogen. These samples were then cut with a Leica CM 1850 cryostat at −20° C. and prepared for microscopy as described previously (Nakashima et al., 2008). Phloroglucinol-HCl staining and Maule staining were carried out as described (Fu et al., 2011). Ultraviolet absorption microspectrophotometry was performed as described (Nakashima et al., 2008). Photographs were taken using a Nikon DXM 1200 color camera attached to a Nikon microphot-FX microscope system with ACT-1 software (Nikon, Japan). Tobacco leave infiltration was performed as described (Sparkes et al., 2006). Imaging of GFP fluorescence by confocal microscopy was performed as described (Wang et al., 2008).

H. Tissue Culture and Transformation

Tobacco (*Nicotiana tabacum* cv. Xanthi NN) was transformed by the leaf-disc method (Horsch et al., 1985). Leaf discs from a tobacco plant grown in a Magenta box were incubated with *Agrobacterium tumefaciens* (AGL1) harboring the MYB construct for 20 minutes. The leaf discs were then blotted dry on filter paper and plated on co-cultivation medium (MS basal medium, 4.3 g/L; Gamborg B5 vitamins 1,000× stock, 1 ml/L; sucrose, 30 g/L; $MgCl_2$, 10 mM; acetosyringone, 100 μM; MES, 0.6 g/L, pH 5.8) for co-cultivation for 4 days in the dark. Leaf discs were transferred to regeneration medium (MS basal medium, 4.3 g/L; Gamborg's B5 vitamins 1,000× stock, 1 ml/L; sucrose, 30 g/L; BAP, 1 mg/L; NAA, 0.1 mg/L; hygromycin, 25 μg/L; ticarcillin 250 μg/L; amoxicillin, 400 μg/L; MES, 0.6 g/L, pH 5.8) after co-cultivation. Leaf discs were sub-cultured every 2 weeks in regeneration medium until plant regeneration. Transgenic plants were maintained in the greenhouse for analysis.

*Agrobacterium*-mediated switchgrass transformation was performed based on a previously published protocol (Xi et al., 2009). The vector used for switchgrass transformation was as previously described (Burris et al., 2009). Briefly, the binary vector contained the attR1-CmR-ccdB-attR2 Gateway compatible cassette cloned downstream under the control of the ZmUbi1 promoter. The PvMYB4 coding sequence was cloned into the pCR8/GW/TOPO backbone, sequence verified, and recombined into the expression vector using Gateway® LR Clonase® II enzyme mix (Invitrogen). For selection, the OsAct1 promoter was cloned along with the hph gene to create a hygromycin-resistance cassette. Additionally, the GUSplus gene was PCR amplified from the pCAMBIA1305.1 backbone (worldwideweb.cambia.org/daisy/cambia/585.html) and fused to the rubi3 promoter (Sivamani and Qu, 2006) as an additional positive selection marker.

I. Electrophoretic Mobility Shift Assays

PvMYB4a was cloned into the pDEST17 expression vector by the Gateway cloning method (Invitrogen). After sequencing, the plasmid was transformed into BL21 DE3 *E. coli* competent cells. IPTG was added to induce expression of PvMYB4. The recombinant protein was purified with the MagneHis™ Protein Purification System (Promega Corporation, Madison, Wis.) then concentrated with an Amicon Ultra-15 Centrifugal Filter (Millipore Corporation, Billerica, Mass.). About 700-1000 ng of purified PvMYB4 protein was used for EMSA in each reaction. The probes were labeled by annealing biotin-labeled olignucleotides or PCR products, then purified with a gel extraction kit (QIAGEN). Oligonucleotides used for EMSA are listed in Table 1. Binding conditions were 12 mM Tris-HCl (pH 7.5), 20 mM NaCl, 50 mM KCl, 5 mM $MgCl_2$, 1 mM DTT, 0.2 mM EDTA, 2.5% glycerol, 1 mM β-ME, 0.05% NP-40 and 2 fmol biotin-labeled probes. The samples were loaded and run in a 6% DNA retardant gel (Invitrogen) in the cold room after the reactions had been incubated at 4° C. for 30 minutes. The DNA was transferred onto Nylon membranes and signal detected with a LightShift® Chemiluminescent EMSA Kit (Thermo Fisher Scientific Inc. Rockford, Ill.) using standard protocols.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or composition employed herein.

U.S. Pat. No. 3,990,944.; U.S. Pat. No. 4,461,648; U.S. Pat. No. 4,535,060; U.S. Pat. No. 4,535,060; U.S. Pat. No. 4,600,590; U.S. Pat. No. 5,000,000; U.S. Pat. No. 5,037,663; U.S. Pat. No. 5,302,523; U.S. Pat. No. 5,322,783; U.S. Pat. No. 5,384,253; U.S. Pat. No. 5,464,765; U.S. Pat. No. 5,538,877; U.S. Pat. No. 5,538,880; U.S. Pat. No. 5,538,880; U.S. Pat. No. 5,545,818; U.S. Pat. No. 5,550,318; U.S. Pat. No. 5,550,318; U.S. Pat. No. 5,563,055; U.S. Pat. No. 5,563,055; U.S. Pat. No. 5,563,055; U.S. Pat. No. 5,563,055; U.S. Pat. No. 5,591,616; U.S. Pat. No. 5,591,616; U.S. Pat. No. 5,610,042; U.S. Pat. No. 5,972,118

Asai et al., *Nature* 415:977-983, 2002.
Bates, *Mol. Biotechnol.*, 2(2):135-145, 1994.
Battraw et al., *Theor. App. Genet.*, 82(2):161-168, 1991.
Bell et al., *Func. Plant Biol.*, 31:235-245, 2004.
Besseau et al., *Plant Cell*, 19:148-162, 2007.
Bevan et al., *Nucleic Acids Research*, 11(2):369-385, 1983.
Bhattacharjee et al., *J. Plant Bioch. and Biotech.* 6, (2):69-73. 1997.
Biemelt et al., *Plant Physiol.*, 135:254-265, 2004.
Bomal et al., *J. Exp. Bot.*, 59:3925-3939, 2008.
Bouchez et al., *EMBO Journal*, 8(13):4197-4204, 1989.
Bouton, J. H., *Curr. Opin. Genet. Dev.*, 17:553-558, 2007.
Bower et al., *Plant Journal*, 2:409-416. 1992.
Buising et al., *Mol Gen Genet*, 243(1):71-81. 1994.
Burris et al., *BioEnerg. Res.*, 2:267-274, 2009.
Bylesjo et al., *J. Proteome Res.*, 8:199-210, 2008.
Callis et al., *Genes Dev.*, 1:1183-1200, 1987.
Casa et al., *Proc. Natl. Acad. Sci. USA*, 90(23):11212-11216, 1993.
Chandler et al., *The Plant Cell*, 1:1175-1183, 1989.
Chen et al., *Nat. Biotechnol.*, 25:759-761 (2007)
Chen et al., *Plant J.*, 48:113-124, 2006.
Chu et al., *Scientia Sinica*, 18:659-668, 1975.
Conkling et al., *Plant Physiol.*, 93:1203-1211, 1990.
Dellaporta et al., *Chromosome Structure and Function: Impact of New Concepts, 18th Stadler Genetics Symposium*, 11:263-282, 1988.
Deluc et al., *Plant Physiol.*, 140:499-511, 2006.

Dereeper et al., (Web Server issue):W465-W469, 2008.
Downward, *BMJ*, 328(7450):1245-1248, 2004.
Duff et al., *Bioresource Tech.*, 55:1-33, 1995.
Ebert et al., *Proc. Natl. Acad. Sci.*, 84:5745-5749, 1987.
Elkind et al., *Proc. Natl. Acad. Sci. USA*, 87:9057-61, 1990.
Ellis et al., *EMBO Journal*, 6(11):3203-3208, 1987.
Escamilla-Trevino et al., *New Phytol.*, 185:143-155, 2009.
European Patent Application 154204, 1985.
Fire et al., *Nature*, 391: 806-11, 1998.
Fornal et al., *Plant J.*, 64:633-644, 2010.
Fornalé et al., *Plant Mol. Biol.*, 62:809-823, 2006.
Fraley et al., *Bio/Technology*, 3:629-635, 1985.
Fromm et al., *Nature*, 319:791-793, 1986.
Fu et al., *Proc. Natl. Acad. Sci. USA*, 108, 3803-3808, 2011.
Fujioka et al., *Physiol. Plantarum*, 100:710-715, 1997.
Fukazawa et al., *Plant Cell*, 12:901-915, 2000.
Gális et al., *Plant J.*, 46:573-592, 2006.
Gallego Giraldo et al., *New Phytol.*, 190:627-639, 2011.
Gallego-Giraldo et al., *Plant Cell Physiol.*, 48:615-625, 2007.
Gallie et al., *The Plant Cell*, 1:301-311, 1989.
Goicoechea et al., *Plant J.*, 43:553-567, 2005.
Gong et al., *Adv. Biochem. Engng. Biotech.* 65: 207-241, 1999.
Guo et al., *Plant Cell*, 13:73-88, 2001.
Hagio et al., *Plant Cell Rep.*, 10(5):260-264, 1991.
Hamilton et al., *Proc. Natl. Acad. Sci. USA*, 93(18):9975-9979, 1996.
Haseloff et al., *Proc. Natl. Acad. Sci. USA*, 94(6):2122-2127, 1997.
Hatton et al., *Plant J.*, 7:859-876, 1995.
He et al., *Plant Cell Reports*, 14 (2-3):192-196, 1994.
Hedden et al., *Plant Physiol.*, 119:365-370, 1999.
Hensgens et al., *Plant Mol. Biol.*, 22(6):1101-1127, 1993.
Hiei et al., *Plant Mol. Biol.*, 35(1-2):205-218, 1997.
Hinchee et al., *Bio/Technol.*, 6:915-922, 1988.
Hisano et al., *In Vitro Cell. Dev-Plant.*, 45:306-313, 2009.
Horsch et al., *Science*, 227:1229-1231, 1985.
Hudspeth et al., *Plant Mol. Biol.*, 12:579-589, 1989.
Ikuta et al., *Bio/technol.*, 8:241-242, 1990.
Ishidia et al., *Nat. Biotechnol.*, 14(6):745-750, 1996.
Israelsson et al., *Plant Physiol.*, 135:221, 2004.
Jackson et al., *BioEnerg. Res.* 1:180-192, 2008.
Jackson, *In Molecular Plant Pathology: A Practical Approach*, 1:163-174, 1991.
Jin et al., *EMBO J.*, 19:6150-6161, 2000.
Jin et al., *Genesis*, 27:104-116, 2000.
Kaeppler et al., *Plant Cell Reports*, 9:415-418, 1990.
Karlen et al., *BMC Bioinformatics*, 8:131, 2007.
Karpinska et al., *Plant Mol. Biol.*, 56:255-270, 2004.
Katz et al., *J. Gen. Microbiol.*, 129:2703-2714, 1983.
Keshwani et al., *Bioresource Technol.*, 100:1515-1523, 2009.
Klee et al., *Bio-Technology*, 3(7):637-642, 1985.
Knittel et al., *Plant Cell Reports*, 14(2-3):81-86, 1994.
Korth et al., *Physiol. Plantarum*, 111:137-143, 2001.
Lawton et al., *Plant Mol. Biol.* 9:315-324, 1987.
Lazzeri, *Methods Mol. Biol.*, 49:95-106, 1995.
Lee et al., *Korean J. Genet.*, 11(2):65-72, 1989.
Legay et al, *Plant Sci.*, 173:542-549, 2007.
Lehner et al., *Brief Funct Genomic Proteomic*, 3(1):68-83, 2004.
Li et al., *Plant Cell*, 22:1620-1632, 2010.
Lo et al., *Plant Cell*, 20:2603, 2008.
McCabe et al., *Bio-Technology*, 11(5):596-598, 1993.
McCormac et al., *Mol. Biotechnol.*, 9:155-159, 1998.
McLaughlin et al., *Biomass Bioenerg.*, 28:515-535, 2005.
McLaughlin et al., *Environ. Sci. Technol.*, 36:2122-2129, 2002.
Mes-Hartree et al., *Appl. Microbiol. Biotechnol.*, 29:462-468, 1988.
Mitsuda et al., *Plant Cell*, 19:270-280, 2007.
Monsma et al., *J. Virol.*, 69:2583, 1995.
Moore et al., *Agron J.*, 83:1073-1077, 1991.
Morjanoff et al., *Biotechnol. Bioeng.* 29:733-741, 1987.
Murashige et al., *Physiol. Plant.*, 15:473-497, 1962.
Nakashima et al., *New Phytol.*, 179:738-750, 2008.
Odell et al., *Nature*, 313:810-812, 1985.
Ogawa et al., *Sci. Rep.*, 13:42-48, 1973.
Okada et al., *Genetics*, 185:745-760, 2010.
Olsen et al., *Trends Plant Sci.*, 10:79-87, 2005.
Olsson et al., *Enzyme and Microb. Technol.* 18:312-331, 1996.
Omirulleh et al., *Plant Mol. Biol.*, 21(3):415-428, 1993.
Ow et al., *Science*, 234:856-859, 1986.
Oyama et al., *Genes Dev.*, 11:2983, 1997.
Patzlaff et al., *Plant J.*, 36:743-754, 2003.
Potrykus et al., *Mol. Gen. Genet.*, 199:183-188, 1985.
Prasher et al., *Biochem. Biophys. Res. Commun.*, 126(3):1259-1268, 1985.
Preston et al., *Plant J.*, 40:979-995, 2004.
Raes et al., *Plant Physiol.*, 133:1051-1071, 2003.
Reichel et al., *Proc. Natl. Acad. Sci.*, 93:5888-5893, 1996.
Reynolds, *Nat. Biotechnol.* 22:326-330, 2004.
Ritala et al., *Plant Mol. Biol.*, 24(2):317-325, 1994.
Rogers et al., *Methods Enzymol.*, 153:253-277, 1987.
Romero et al., *Plant J.*, 14:273-284, 1998.
Ruden et al., *Nature*, 350:250-252, 1991.
Saathoff et al., *PloS ONE*, 6:e16416, 2011.
Sadowski et al., *Nature*, 335:563-564, 1988.
Sarath et al., *Bioresource Technol.*, 98:2985-2992, 2007.
Schmer et al., *Proc. Natl. Acad. Sci. USA*, 105:464-469, 2008.
Sheen et al., *Plant Journal*, 8(5):777-784, 1995.
Sheen, J., *Plant Physiol.*, 127:1466-1475, 2001.
Shen et al., *BioEnerg. Res.*, 2:217-232, 2009a.
Shen et al., *BioEnerg. Res.*, 2:233-245, 2009b.
Singsit et al., *Transgenic Res.*, 6(2):169-176, 1997.
Sivamani et al., *Plant Mol. Biol.*, 60:225-239, 2006.
Somleva et al., *Crop Science*, 42:2080-2087, 2002.
Somleva et al., *Plant Biotechnol. J.*, 6:663-678, 2008.
Sonbol et al., *Plant Mol. Biol.*, 70:283-296, 2009.
Sparkes et al., *Nat. Protoc.*, 1:2019-2025, 2006.
Springer et al., *Genome Res.*, 17:264, 2007.
Stalker et al., *Science*, 242:419-422, 1988.
Stracke et al., *Curr. Opin. Plant Biol.*, 4:447-456, 2001.
Sullivan et al., *Mol. Gen. Genet.*, 215(3):431-440, 1989.
Sun et al., *Bioresource Technol.* 83:1-11, 2002.
Sutcliffe, *Proc. Natl. Acad. Sci. USA*, 75:3737-3741, 1978.
Tamagnone et al., *Plant Cell*, 10:135-154, 1998.
Thillet et al., *J. Biol. Chem.*, 263:12500-12508, 1988.
Thomas et al., *Plant Physiol.*, 135:668, 2004.
Thomas et al., *Plant Sci.* 69:189-198, 1990.
Tian, *Plant Cell Rep.*, 16:267-271, 1997.
Tingay et al., *The Plant Journal*, 11(6):1369-1376. 1997.
Tobias et al., *Plant Genome*, 1:111-124, 2008.
Tobias et al., *Theor. Appl. Genet.*, 111:956-964, 2005.
Tomes et al., *Plant. Mol. Biol.*, 14(2):261-268, 1990.
Torbet et al., *Crop Science*, 38(1):226-231, 1998.
Torbet et al., *Plant Cell Reports*, 14(10):635-640, 1995.
Tsukada et al., *Plant Cell Physiol.*, 30(4):599-604, 1989.
Twell et al., *Plant Physiol.*, 91:1270-1274, 1989.
Van Eck et al., *Plant Cell Reports*, 14(5):299-304, 1995
Vasil et al., *Plant Physiol.*, 91:1575-1579, 1989.
Walker et al., *Proc. Natl. Acad. Sci. USA*, 84:6624-6628, 1987.

Wang et al., *Molecular and Cellular Biology*, 12(8):3399-3406, 1992.
Wang et al., *New Phytol.*, 177:525-536, 2008.
Wang et al., *Plant Physiol.*, 146:1759-1772, 2008.
Wang et al., *Proc. Natl. Acad. Sci. USA*, 107:22338-22343, 2010.
Williams et al., *Environ. Sci. Technol.*, 43:4763-4775, 2009.
WO 9217598
WO 94/09699
WO 95/06128
WO 97/4103
WO 97/41228
WO 97/41228
Wullschleger et al., *Agron. J.*, 102:1158-1168, 2010.
Wyman, *Annu. Rev. Energy Environ.* 24:189-226, 1999.
Xi et al., *Methods Mol. Biol.*, 581:53-59, 2009.
Yang et al., *Proc. Natl. Acad. Sci. USA*, 87:4144-4148, 1990.
Zhang et al., *Science* 267:240-243, 1995.
Zhao et al., *J. Zhejiang Univ. Sci.*, B 11: 471-481, 2010.
Zhao et al., *Plant Cell*, 19:3805-3818, 2007.
Zhao et al., *Trends Plant Sci.*, 16:227-233. 2011.
Zhong et al., *Trends Plant Sci.*, 15: 625-632, 2010.
Zhou et al., *Proc. Natl. Acad. Sci. USA*, 107: 17803-17808, 2010.
Zukowsky et al., *Proc. Natl. Acad. Sci.*, 80:1101-1105, 1983.

What is claimed is:

1. A DNA construct comprising a nucleic acid sequence selected from the group consisting of:
   (a) a nucleic acid comprising the sequence of SEQ ID NO: 1; SEQ ID NO:7; SEQ ID NO:9; SEQ ID NO:11; or SEQ ID NO:13;
   (b) a nucleic acid sequence exhibiting at least 90% sequence identity to the nucleic acid sequence of SEQ ID NO:1; SEQ ID NO:7; SEQ ID NO:9; SEQ ID NO:11; or SEQ ID NO:13;
   (c) a nucleic acid sequence that encodes a polypeptide at least 90% identical to the polypeptide sequence of SEQ ID NO:2; SEQ ID NO:8; SEQ ID NO:10; SEQ ID NO:12; or SEQ ID NO:14; and
   (d) a nucleic acid sequence comprising the full complement of (a)-(c), wherein the nucleic acid sequence is operably linked to a heterologous promoter sequence, wherein the nucleic acid sequence encodes a protein comprising a R2-R3 domain, and wherein introduction of the nucleic acid sequence in a transgenic plant reduces the lignin content of the plant.

2. The DNA construct of claim 1, wherein the heterologous promoter sequence is a developmentally-regulated, organelle-specific, inducible, tissue-specific, constitutive, cell-specific, seed specific, or germination-specific promoter.

3. A transgenic plant or plant part thereof comprising the DNA construct of claim 1.

4. A transgenic plant cell comprising the DNA construct of claim 1.

5. The transgenic plant of claim 3, wherein the plant is forage plant, a biofuel crop, or a cereal crop.

6. The transgenic plant of claim 5, wherein the biofuel crop is switchgrass (*Panicum virgatum*), giant reed (*Arundo donax*), reed canarygrass (*Phalaris arundinacea*), Miscanthus×giganteus, Miscanthus sp., sericea lespedeza (*Lespedeza cuneata*), corn, sugarcane, sorghum, millet, ryegrass, timothy, Kochia (*Kochia scoparia*), soybean, alfalfa, clover, sunn hemp, kenaf, bahiagrass, bermudagrass, dallisgrass, pangolagrass, big bluestem, indiangrass, fescue (*Festuca* sp.), *Eremochloa ophiuroides* (centipede grass), *Dactylis* sp., *Brachypodium distachyon*, smooth bromegrass, orchardgrass, Kentucky bluegrass, poplar, rice, cotton, *Salvia miltiorrhiza* (red sage), apple, *Vitis vinifera* (common grape), *Ricinus communis* (castor oil plant), *Humulus lupulus* (hops), Dahlia, Dendrobium (orchid), Brassica rapa (mustard), kudzu (*Pueraria lobata*) or wheat.

7. The transgenic plant of claim 6, wherein the biofuel crop is switchgrass (*Panicum virgatum*).

8. The transgenic plant of claim 3, further defined as an R0 transgenic plant.

9. The transgenic plant of claim 3, further defined as a progeny plant of any generation of an R0 transgenic plant, wherein the transgenic plant has inherited the DNA construct.

10. The transgenic plant of claim 3, further comprising at least a second nucleic acid sequence that down-regulates lignin biosynthesis.

11. The transgenic plant of claim 10, wherein the second nucleic acid DNA sequence down-regulates coumarate 3-hydroxylase (C3H), phenylalanine ammonia-lyase (PAL), cinnamate 4-hydroxylase (C4H), hydroxycinnamoyl coenzyme A: shikimate hydroxycinnamoyltransferase (HCT), caffeic acid O-methyltransferase (COMT), caffeoyl CoA 3-O-methyltransferase (CCoAOMT), ferulate 5-hydroxylase (F5H), cinnamyl alcohol dehydrogenase (CAD), cinnamoyl CoA-reductase (CCR), or 4-coumarate-CoA ligase (4CL).

12. The transgenic plant of claim 10, wherein the second nucleic acid sequence comprises an antisense or RNAi construct.

13. A method of modifying the lignin content of a plant comprising introducing in the plant a MYB4 transcription factor that functions to suppress lignin biosynthesis, wherein the MYB4 transcription factor is selected from the group consisting of:
   (a) a nucleic acid comprising the sequence of SEQ ID NO: 1; SEQ ID NO:7; SEQ ID NO:9; SEQ ID NO:11; or SEQ ID NO:13;
   (b) a nucleic acid sequence exhibiting at least 90% sequence identity to the nucleic acid sequence of SEQ ID NO:1; SEQ ID NO:7; SEQ ID NO:9; SEQ ID NO:11; or SEQ ID NO:13;
   (c) a nucleic acid sequence that encodes a polypeptide at least 90% identical to the polypeptide sequence of SEQ ID NO:2; SEQ ID NO:8; SEQ ID NO:10; SEQ ID NO:12; or SEQ ID NO:14; and
   (d) a nucleic acid sequence comprising the full complement of (a)-(c), wherein the nucleic acid sequence is operably linked to a heterologous promoter sequence, wherein the nucleic acid sequence encodes a protein comprising a R2-R3 domain, and wherein introduction of the nucleic acid sequence in a transgenic plant reduces the lignin content of the plant,
   wherein the plant is switchgrass (*Panicum virgatum*).

14. The method of claim 13, comprising over-expressing in the plant the MYB4 transcription factor, wherein lignin content is decreased in the plant.

15. A method of decreasing a lignin content of a plant, comprising expressing in the plant the DNA construct of claim 1, wherein the lignin content is decreased in the plant.

16. The method of claim 14, wherein the content of fermentable carbohydrates is increased in the plant.

17. A method for producing biomass or feedstock comprising obtaining the transgenic plant or part thereof according to claim 3 and harvesting feedstock or biomass therefrom.

18. The method of claim 17, further comprising producing a biofuel from said biomass or feedstock.

19. A method of modifying the lignin content of a plant comprising down-regulating in the plant a MYB4 transcription factor that functions to increase lignin biosynthesis, wherein the plant is switchgrass (*Panicum virgatum*).

20. The method of claim 19, wherein down-regulating MYB4 transcription factor comprises introducing in the plant a RNAi or antisense construct comprising all or a part of the nucleic acid sequence of SEQ ID NO: 1; SEQ ID NO:7; SEQ ID NO:9; SEQ ID NO:11; SEQ ID NO:13; wherein the expression of the RNAi or antisense construct down-regulates said MYB4 transcription factor.

* * * * *